(12) United States Patent
Mosrin et al.

(10) Patent No.: US 11,089,783 B2
(45) Date of Patent: *Aug. 17, 2021

(54) 2-(HET)ARYL-SUBSTITUTED FUSED HETEROCYCLE DERIVATIVES AS PESTICIDES

(71) Applicant: Bayer Aktiengesellschaft, Leverkusen (DE)

(72) Inventors: Marc Mosrin, Cologne (DE); Ruediger Fischer, Pulheim (DE); Dominik Hager, Monheim (DE); Laura Hoffmeister, Duesseldorf (DE); Nina Kausch-Busies, Bergisch Gladbach (DE); David Wilcke, Duesseldorf (DE); Matthieu Willot, Duesseldorf (DE); Kerstin Ilg, Cologne (DE); Ulrich Goergens, Ratingen (DE); Daniela Portz, Vettweiss (DE); Sascha Eilmus, Leichlingen (DE); Andreas Turberg, Haan (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/609,631

(22) PCT Filed: Apr. 25, 2018

(86) PCT No.: PCT/EP2018/060568
§ 371 (c)(1),
(2) Date: Oct. 30, 2019

(87) PCT Pub. No.: WO2018/202494
PCT Pub. Date: Nov. 8, 2018

(65) Prior Publication Data
US 2020/0146293 A1     May 14, 2020

(30) Foreign Application Priority Data

May 2, 2017  (EP) .................................. 17168922

(51) Int. Cl.
*A01N 43/90*   (2006.01)
*C07D 487/04*  (2006.01)

(52) U.S. Cl.
CPC ........... *A01N 43/90* (2013.01); *C07D 487/04* (2013.01)

(58) Field of Classification Search
CPC .............................. A01N 43/90; C07D 487/04
USPC ...................................................... 514/248
See application file for complete search history.

(56) References Cited

U.S. PATENT DOCUMENTS

| 10,364,243 B2   | 7/2019 | Ruediger et al. |
| 2017/0073342 A1 | 3/2017 | Ruediger et al. |
| 2018/0271099 A1 | 9/2018 | Ruediger et al. |
| 2019/0241564 A1 | 8/2019 | Ruediger et al. |

FOREIGN PATENT DOCUMENTS

| EP | 2975039 A1    | 1/2016  |
| WO | 2010/125985 A1 | 11/2010 |
| WO | 2014/142292 A1 | 9/2014  |
| WO | 2014148451 A1 | 9/2014  |
| WO | 2015/121136 A1 | 8/2015  |
| WO | 2016/023954 A2 | 2/2016  |
| WO | 2016/039441 A1 | 3/2016  |
| WO | 2016/046071 A1 | 3/2016  |
| WO | 2016059145 A1 | 4/2016  |
| WO | 2016104746 A1 | 6/2016  |
| WO | 2016116338 A1 | 7/2016  |
| WO | 2017025419 A2 | 2/2017  |

OTHER PUBLICATIONS

International Search Report of International Patent Application No. PCT/EP2018/060588, dated Aug. 6, 2018.
Extended European Search Report issued in application No. EP 17 16 8921, dated Sep. 28, 2017.

*Primary Examiner* — Kahsay Habte
(74) *Attorney, Agent, or Firm* — Mcbee Moore & Vanik IP, LLC

(57) ABSTRACT

The invention relates to novel compounds of the formula (I)

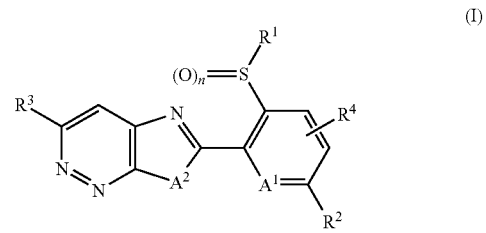

in which $R^1$, $R^2$, $R^3$, $R^4$, $A^1$, $A^2$ and n have the definitions given above,
to agrochemical formulations comprising the compounds of formula (I) and to their use as acaricides and/or insecticides for controlling animal pests, particularly arthropods and especially insects and arachnids.

13 Claims, No Drawings

2-(HET)ARYL-SUBSTITUTED FUSED HETEROCYCLE DERIVATIVES AS PESTICIDES

CROSS-REFERENCE TO RELATED APPLICATIONS

This application is the National Stage entry of International Application No. PCT/EP2018/060568, filed 25 Apr. 2018, which claims priority to European Patent Application No. 17168922.7, filed 2 May 2017.

BACKGROUND

Field

The present invention relates to novel 2-(het)aryl-substituted fused heterocycle derivatives of the formula (I), to their use as acaricides and/or insecticides for controlling animal pests, particularly arthropods and especially insects and arachnids.

Description of Related Art

Fused heterocycle derivatives having insecticidal properties have already been described in the literature, for example in WO 2010/125985, WO 2014/142292, WO 2014/148451, WO 2016/023954, WO 2016/039441, WO 2016/046071, WO 2016/059145, WO 2016/104746, WO 2016/116338, WO 2015/121136 and WO 2017/025419.

Modern insecticides and acaricides have to meet many demands, for example in relation to extent, persistence and spectrum of their action and possible use. Questions of toxicity, sparing of beneficial species and pollinators, environmental properties, application rates, combinability with other active ingredients or formulation auxiliaries play a role, as does the question of the complexity involved in the synthesis of an active ingredient, and resistances can also occur, to mention just a few parameters. For all these reasons alone, the search for novel crop protection compositions cannot be considered complete, and there is a constant need for novel compounds having improved properties compared to the known compounds, at least in relation to individual aspects.

SUMMARY

It was an object of the present invention to provide compounds for use for controlling animal pests, by which the spectrum of the pesticides is widened in various aspects.

Novel fused bicyclic heterocycle derivatives have now been found, these having advantages over the compounds already known, examples of which include better biological or environmental properties, a wider range of application methods, better insecticidal or acaricidal action, and good compatibility with crop plants. The fused bicyclic heterocycle derivatives can be used in combination with further agents for improving efficacy, especially against insects that are difficult to control.

This object, and further objects which are not stated explicitly but can be discerned or derived from the connections discussed herein, are therefore achieved by novel compounds of the formula (I)

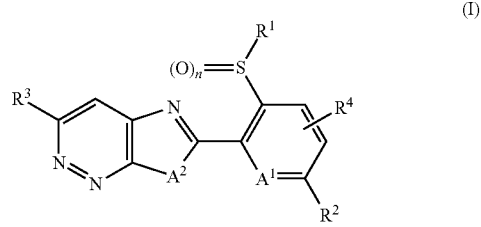

in which (configuration 1)
$A^1$ is nitrogen, $=N^+(O^-)-$ or $=C(R^5)-$,
$A^2$ is $-N(R^6)-$, oxygen or sulfur,
$R^1$ is $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-haloalkoxy-$(C_1-C_6)$-alkyl, $(C_2-C_6)$-alkenyl, $(C_2-C_6)$-alkenyloxy-$(C_1-C_6)$-alkyl, $(C_2-C_6)$-haloalkenyloxy-$(C_1-C_6)$-alkyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_6)$-alkyl, $(C_2-C_6)$-haloalkynyloxy-$(C_1-C_6)$-alkyl, $(C_2-C_6)$-haloalkynyl, $(C_2-C_6)$-cyanoalkynyl, $(C_3-C_8)$-cycloalkyl, $(C_3-C_6)$-halocycloalkyl, $(C_3-C_6)$-cyanocycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, amino, $(C_1-C_6)$-alkylamino, di-$(C_1-C_6)$-alkyl-amino, $(C_3-C_8)$-cycloalkylamino, $(C_1-C_6)$-alkylcarbonylamino, $(C_1-C_6)$-alkylthio-$(C_1-C_6)$-alkyl, $(C_1-C_6)$-haloalkylthio-$(C_1-C_6)$-alkyl, $(C_1-C_6)$-alkylsulfinyl-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-alkyl, $(C_1-C_6)$-haloalkylsulfonyl-$(C_1-C_6)$-alkyl, $(C_1-C_6)$-alkoxy-$(C_1-C_6)$-alkylthio-$(C_1-C_6)$-alkyl, $(C_1-C_6)$-alkoxy-$(C_1-C_6)$-alkylsulfinyl-$(C_1-C_6)$-alkyl, $(C_1-C_6)$-alkoxy-$(C_1-C_6)$-alkylsulfonyl-$(C_1-C_6)$-alkyl, $(C_1-C_6)$-alkylcarbonyl-$(C_1-C_6)$-alkyl, $(C_1-C_6)$-haloalkylcarbonyl-$(C_1-C_6)$-alkyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkylsulfonylamino, aminosulfonyl-$(C_1-C_6)$-alkyl, $(C_1-C_6)$-alkylaminosulfonyl-$(C_1-C_6)$-alkyl, di-$(C_1-C_6)$-alkylaminosulfonyl-$(C_1-C_6)$-alkyl, or is in each case optionally identically or differently mono- or poly-aryl-, -hetaryl- or -heterocyclyl-substituted $(C_1-C_6)$-alkyl, $(C_1-C_6)$-alkoxy, $(C_2-C_6)$-alkenyl, $(C_2-C_6)$-alkynyl, $(C_3-C_8)$-cycloalkyl, where aryl, hetaryl or heterocyclyl may each optionally be mono- or polysubstituted identically or differently by halogen, cyano, nitro, hydroxyl, amino, carboxyl, carbamoyl, aminosulfonyl, $(C_1-C_6)$-alkyl, $(C_3-C_8)$-cycloalkyl, $(C_1-C_6)$-alkoxy, $(C_1-C_6)$-haloalkyl, $(C_1-C_6)$-haloalkoxy, $(C_1-C_6)$-alkylthio, $(C_1-C_6)$-alkylsulfinyl, $(C_1-C_6)$-alkylsulfonyl, $(C_1-C_6)$-alkylsulfimino, $(C_1-C_6)$-alkylsulfimino-$(C_1-C_6)$-alkyl, $(C_1-C_6)$-alkylsulfimino-$(C_2-C_6)$-alkylcarbonyl, $(C_1-C_6)$-alkylsulfoximino, $(C_1-C_6)$-alkylsulfoximino-$(C_1-C_6)$-alkyl, $(C_1-C_6)$-alkylsulfoximino-$(C_2-C_6)$-alkylcarbonyl, $(C_1-C_6)$-alkoxycarbonyl, $(C_1-C_6)$-alkylcarbonyl, $(C_3-C_6)$-trialkylsilyl or benzyl, $R^2$ is a group selected from $-C(=O)-NR^{11}R^{12}$, $-C(=S)-NR^{11}R^{12}$, $-NR^{11}R^{12}$, $-NR^{11}-C(=O)-R^8$ and $-NR^{11}-C(=S)-R^8$, $R^3$ is $C_2$-haloalkyl, $R^4$ is hydrogen, cyano, halogen, nitro, acetyl, hydroxyl, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, cyano$(C_3-C_8)$-cycloalkyl, $(C_1-C_6)$-alkyl, $(C_1-C_6)$-haloalkyl, $(C_1-$ $C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), is in each case optionally singly or multiply, identically or differently substituted aryl or hetaryl, where (in the case of hetaryl) at least one carbonyl group may optionally be present and where possible substituents in each case are as follows: cyano, carboxyl, halogen, nitro, acetyl, hydroxyl, amino, SCN, tri-($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)-haloalkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxy imino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloaoalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di-($C_1$-$C_6$)alkylaminocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulfonylamino, ($C_1$-$C_6$)alkylamino, di-($C_1$-$C_6$)alkylamino, aminosulfonyl, ($C_1$-$C_6$)alkylaminosulfonyl, di-($C_1$-$C_6$)alkylaminosulfonyl, ($C_1$-$C_6$)alkylsulfoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, ($C_1$-$C_6$)alkylcarbonylamino, $R^5$ is hydrogen, cyano, halogen, nitro, acetyl, hydroxyl, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxy imino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkyl carbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkyl-aminocarbonyl, di-($C_1$-$C_6$)-alkyl-aminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkyl-aminothiocarbonyl, ($C_3$-$C_8$)-cycloalkylamino or —NHCO—($C_1$-$C_6$)-alkyl (($C_1$-$C_6$)-alkylcarbonylamino), $R^6$ is ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)haloalkoxy-($C_1$-$C_6$)alkyl, ($C_2$-$C_6$)alkenyl, ($C_2$-$C_6$)alkenyloxy-($C_1$-$C_6$)alkyl, ($C_2$-$C_6$)haloalkenyloxy-($C_1$-$C_6$)alkyl, ($C_2$-$C_6$)haloalkenyl, ($C_2$-$C_6$)cyanoalkenyl, ($C_2$-$C_6$) alkynyl, ($C_2$-$C_6$)alkynyloxy-($C_1$-$C_6$)alkyl, ($C_2$-$C_6$) haloalkynyloxy-($C_1$-$C_6$)alkyl, ($C_2$-$C_6$)haloalkynyl, ($C_2$-$C_6$)cyanoalkynyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo ($C_3$-$C_8$)cycloalkyl, ($C_1$-$C_6$)alkylthio-($C_1$-$C_6$)alkyl, ($C_1$-$C_6$)haloalkylthio-($C_1$-$C_6$)alkyl, ($C_1$-$C_6$)alkylsulfinyl-($C_1$-$C_6$)alkyl, ($C_1$-$C_6$)haloalkylsulfinyl-($C_1$-$C_6$)alkyl, ($C_1$-$C_6$) alkylsulfonyl-($C_1$-$C_6$)alkyl, ($C_1$-$C_6$)haloalkylsulfonyl-($C_1$-$C_6$)alkyl, ($C_1$-$C_6$)alkoxy-($C_1$-$C_6$)alkylthio-($C_1$-$C_6$)alkyl, ($C_1$-$C_6$)alkoxy-($C_1$-$C_6$)alkylsulfinyl-($C_1$-$C_6$)alkyl, ($C_1$-$C_6$)alkoxy-($C_1$-$C_6$)alkylsulfonyl-($C_1$-$C_6$)alkyl, ($C_1$-$C_6$)alkylcarbonyl-($C_1$-$C_6$)alkyl, ($C_1$-$C_6$)haloalkylcarbonyl-($C_1$-$C_6$)alkyl, ($C_1$-$C_6$)alkoxycarbonyl-($C_1$-$C_6$)alkyl, ($C_1$-$C_6$)haloalkoxycarbonyl-($C_1$-$C_6$)alkyl, aminocarbonyl-($C_1$-$C_6$)alkyl, ($C_1$-$C_6$)alkylamino-($C_1$-$C_6$)alkyl, di-($C_1$-$C_6$)alkylamino-($C_1$-$C_6$)alkyl or ($C_3$-$C_8$)cycloalkylamino-($C_1$-$C_6$)alkyl, $R^8$ is amino or in each case optionally singly or multiply, identically or differently substituted $C_1$-$C_4$-alkylamino, di-($C_1$-$C_4$)-alkylamino, $C_2$-$C_6$-alkenylamino, $C_2$-$C_6$-alkynylamino, $C_3$-$C_{12}$-cycloalkylamino, $C_3$-$C_{12}$-cycloalkyl-($C_1$-$C_6$)-alkylamino, $C_4$-$C_{12}$-bicycloalkylamino or hydrazino, where the substituents may independently be selected from halogen, cyano, nitro, hydroxyl, (C=O)OH, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_2$-$C_6$-alkoxycarbonyl, $C_2$-$C_6$-alkylcarbonyl, $C_1$-$C_6$-alkylthiocarbonyl, $C_1$-$C_6$-haloalkylcarbonyl, $C_1$-$C_6$-haloalkylthiocarbonyl, $C_1$-$C_6$-alkylcarbonylamino, aminocarbonyl, $C_1$-$C_6$-alkylaminocarbonyl, di-($C_1$-$C_6$)-alkylaminocarbonyl, aminothiocarbonyl, $C_1$-$C_6$-alkylaminothiocarbonyl, di-($C_1$-$C_6$)-alkylaminothiocarbonyl, $C_3$-$C_6$-trialkylsilyl, amino, $C_1$-$C_4$-alkylamino, di-($C_1$-$C_4$-alkyl)amino, $C_3$-$C_6$-cycloalkylamino, aminosulfonyl, $C_1$-$C_6$-alkylaminosulfonyl, di-($C_1$-$C_6$)-alkylaminosulfonyl, sulfonylamino, $C_1$-$C_6$-alkylsulfonylamino and di-($C_1$-$C_6$)-alkylsulfonylamino, $R^{11}$, $R^{12}$ are independently hydrogen or in each case optionally singly or multiply, identically or differently substituted $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or $C_4$-$C_{12}$-bicycloalkyl, where the substituents may independently be selected from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_1$-$C_4$-alkylsulfimino-$C_1$-$C_4$-alkyl, $C_1$-$C_4$-alkylsulfimino-$C_2$-$C_5$-alkylcarbonyl, $C_1$-$C_4$-alkylsulfoximino, $C_1$-$C_4$-alkylsulfoximino-$C_1$-$C_4$-alkyl, $C_1$-$C_4$-alkylsulfoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di-($C_1$-$C_4$-alkyl)amino, $C_3$-$C_6$-cycloalkylamino, a phenyl ring and a 3- or 6-membered aromatic partly saturated or saturated heterocycle, where the phenyl ring or heterocycle may in each case optionally be mono- or polysubstituted identically or differently, and where the substituents may independently be selected from $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl, ($C_1$-$C_4$-alkyl)($C_1$-$C_4$-alkoxy)imino or $R^{11}$, $R^{12}$ are independently a phenyl ring or a 3- to 6-membered aromatic partly saturated or saturated heterocycle, where the heteroatoms are selected from the group of N, S and O, where the phenyl ring or heterocycle may in each case optionally be mono- or polysubstituted identically or differently, and where the substituents may independently be selected from $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl and ($C_1$-$C_4$-alkyl)($C_1$-$C_4$-alkoxy)imino, and n is 0, 1 or 2.

DETAILED DESCRIPTION OF A PREFERRED EMBODIMENT

It has additionally been found that the compounds of the formula (I) have very good efficacy as pesticides, preferably as insecticides and/or acaricides, and additionally generally have very good plant compatibility, in particular with respect to crop plants.

The compounds according to the invention are defined in general terms by the formula (I). Preferred substituents or ranges of the radicals given in the formulae mentioned above and below are illustrated hereinafter:

Configuration 2:

$A^1$ is preferably nitrogen, $=N^+(O^-)$— or $=C(R^5)$—, $A^2$ is preferably —$N(R^6)$— or oxygen, $R^1$ is preferably ($C_1$-$C_4$)alkyl, ($C_1$-$C_4$)hydroxyalkyl, ($C_1$-$C_4$)haloalkyl, ($C_1$-$C_4$)cyanoalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyloxy-($C_1$-$C_4$)alkyl, ($C_2$-$C_4$)haloalkynyl, ($C_2$-$C_4$)cyanoalkynyl, ($C_3$-$C_8$)cycloalkyl, ($C_3$-$C_6$)-halocycloalkyl, ($C_3$-$C_6$)-cyanocycloalkyl, ($C_3$-$C_6$)cycloalkyl($C_3$-$C_6$)cycloalkyl, ($C_3$-$C_6$)alkyl-($C_3$-$C_6$)cycloalkyl, halo($C_3$-$C_6$)cycloalkyl, ($C_1$-$C_4$)alkylamino, di-($C_1$-$C_4$)alkyl-amino, ($C_3$-$C_6$)cycloalkylamino, ($C_1$-$C_4$)alkylcarbonylamino, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulfinyl-($C_1$-$C_4$)alkyl, ($C_1$-$C_4$)haloalkylsulfinyl-($C_1$-$C_4$)alkyl, ($C_1$-$C_4$)alkylsulfonyl-($C_1$-$C_4$)alkyl, ($C_1$-$C_4$)alkylcarbonyl-($C_1$-$C_4$)alkyl, ($C_1$-$C_4$)haloalkylcarbonyl-($C_1$-$C_4$)alkyl, ($C_1$-$C_4$)alkylsulfonylamino, or is in each case optionally identically or differently mono- or di-aryl-, -hetaryl- or -heterocyclyl-substituted ($C_1$-$C_4$)alkyl, ($C_1$-$C_4$)alkoxy, ($C_2$-$C_4$)alkenyl, ($C_2$-$C_4$)alkynyl, ($C_3$-$C_6$)cycloalkyl, where aryl, hetaryl or heterocyclyl may each optionally identically or differently be mono- or disubstituted by halogen, cyano, carbamoyl, aminosulfonyl, ($C_1$-$C_4$)alkyl, ($C_3$-$C_4$)cycloalkyl, ($C_1$-$C_4$)alkoxy, ($C_1$-$C_4$)haloalkyl, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)alkylsulfimino, or $R^2$ is preferably —C(=O)—$NR^{11}R^{12}$, —C(=S)—$NR^{11}R^{12}$, —$NR^{11}R^{12}$, —$NR^{11}$—C(=O)—$R^8$ or —$NR^{11}$—C(=S)—$R^8$, $R^3$ is preferably $C_2$-haloalkyl, $R^4$ is preferably hydrogen, cyano, halogen, nitro, acetyl, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, cyano ($C_3$-$C_8$)-cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, aminothiocarbonyl, $(C_1$-$C_4)$alkylaminocarbonyl, di-$(C_1$-$C_4)$alkylaminocarbonyl, $(C_1$-$C_4)$alkylsulfonylamino, $(C_1$-$C_4)$alkylamino, di-$(C_1$-$C_4)$alkylamino, aminosulfonyl, $(C_1$-$C_4)$alkylaminosulfonyl, di-$(C_1$-$C_4)$alkylaminosulfonyl, aminothiocarbonyl, NHCO—$(C_1$-$C_4)$alkyl ($(C_1$-$C_4)$alkylcarbonylamino), and also preferably is phenyl or hetaryl, each of which is optionally mono- or disubstituted identically or differently, where (in the case of hetaryl) at least one carbonyl group may optionally be present and where possible substituents are in each case as follows: cyano, halogen, nitro, acetyl, amino, $(C_3$-$C_6)$cycloalkyl, $(C_3$-$C_6)$cycloalkyl-$(C_3$-$C_6)$cycloalkyl, $(C_1$-$C_4)$alkyl-$(C_3$-$C_6)$cycloalkyl, halo$(C_3$-$C_6)$cycloalkyl, $(C_1$-$C_4)$alkyl, $(C_1$-$C_4)$haloalkyl, $(C_1$-$C_4)$cyanoalkyl, $(C_1$-$C_4)$hydroxyalkyl, $(C_1$-$C_4)$alkoxy-$(C_1$-$C_4)$alkyl, $(C_2$-$C_4)$alkenyl, $(C_2$-$C_4)$haloalkenyl, $(C_2$-$C_4)$cyanoalkenyl, $(C_2$-$C_4)$alkynyl, $(C_2$-$C_4)$haloalkynyl, $(C_2$-$C_4)$cyanoalkynyl, $(C_1$-$C_4)$alkoxy, $(C_1$-$C_4)$haloalkoxy, $(C_1$-$C_4)$cyanoalkoxy, $(C_1$-$C_4)$alkoxy-$(C_1$-$C_4)$alkoxy, $(C_1$-$C_4)$alkylhydroxyimino, $(C_1$-$C_4)$alkoxyimino, $(C_1$-$C_4)$alkyl-$(C_1$-$C_4)$alkoxyimino, $(C_1$-$C_4)$haloalkyl-$(C_1$-$C_4)$alkoxyimino, $(C_1$-$C_4)$alkylthio, $(C_1$-$C_4)$haloalkylthio, $(C_1$-$C_4)$alkylthio-$(C_1$-$C_4)$alkyl, $(C_1$-$C_4)$alkylsulfinyl, $(C_1$-$C_4)$haloalkylsulfinyl, $(C_1$-$C_4)$alkylsulfinyl-$(C_1$-$C_4)$alkyl, $(C_1$-$C_4)$alkylsulfonyl, $(C_1$-$C_4)$haloalkylsulfonyl, $(C_1$-$C_4)$alkylsulfonyl-$(C_1$-$C_4)$alkyl, $(C_1$-$C_4)$alkylsulfonyloxy, $(C_1$-$C_4)$alkylcarbonyl, $(C_1$-$C_4)$haloalkylcarbonyl, aminocarbonyl, $(C_1$-$C_4)$alkylaminocarbonyl, di-$(C_1$-$C_4)$alkylaminocarbonyl, $(C_1$-$C_4)$alkylsulfonylamino, $(C_1$-$C_4)$alkylamino, di-$(C_1$-$C_4)$alkylamino, aminosulfonyl, $(C_1$-$C_4)$alkylaminosulfonyl, di-$(C_1$-$C_4)$alkylaminosulfonyl, NHCO—$(C_1$-$C_4)$alkyl ($(C_1$-$C_4)$alkylcarbonylamino), $R^5$ is preferably hydrogen, cyano, halogen, nitro, acetyl, hydroxyl, amino, SCN, tri-$(C_1$-$C_4)$alkylsilyl, $(C_3$-$C_6)$cycloalkyl, $(C_3$-$C_6)$cycloalkyl-$(C_3$-$C_6)$cycloalkyl, $(C_1$-$C_4)$alkyl-$(C_3$-$C_6)$cycloalkyl, halo$(C_3$-$C_6)$cycloalkyl, $(C_1$-$C_4)$alkyl, $(C_1$-$C_4)$haloalkyl, $(C_1$-$C_4)$cyanoalkyl, $(C_1$-$C_4)$hydroxyalkyl, $(C_1$-$C_4)$alkoxy-$(C_1$-$C_4)$alkyl, $(C_2$-$C_4)$alkenyl, $(C_2$-$C_4)$haloalkenyl, $(C_2$-$C_4)$cyanoalkenyl, $(C_2$-$C_4)$alkynyl, $(C_2$-$C_4)$haloalkynyl, $(C_2$-$C_4)$cyanoalkynyl, $(C_1$-$C_4)$alkoxy, $(C_1$-$C_4)$haloalkoxy, $(C_1$-$C_4)$cyanoalkoxy, $(C_1$-$C_4)$alkoxy-$(C_1$-$C_4)$alkoxy, $(C_1$-$C_4)$alkylhydroxyimino, $(C_1$-$C_4)$alkoxyimino, $(C_1$-$C_4)$alkyl-$(C_1$-$C_4)$alkoxyimino, $(C_1$-$C_4)$haloalkyl-$(C_1$-$C_4)$alkoxyimino, $(C_1$-$C_4)$alkylthio, $(C_1$-$C_4)$haloalkylthio, $(C_1$-$C_4)$alkylthio-$(C_1$-$C_4)$alkyl, $(C_1$-$C_4)$alkylsulfinyl, $(C_1$-$C_4)$haloalkylsulfinyl, $(C_1$-$C_4)$alkylsulfinyl-$(C_1$-$C_4)$alkyl, $(C_1$-$C_4)$alkylsulfonyl, $(C_1$-$C_4)$haloalkylsulfonyl, $(C_1$-$C_4)$alkylsulfonyl-$(C_1$-$C_4)$alkyl, $(C_1$-$C_4)$alkylsulfonyloxy, $(C_1$-$C_4)$alkylcarbonyl, $(C_1$-$C_4)$haloalkylcarbonyl, aminocarbonyl, aminothiocarbonyl, $(C_1$-$C_4)$alkylaminocarbonyl, di-$(C_1$-$C_4)$alkylaminocarbonyl, $(C_1$-$C_4)$alkylsulfonylamino, $(C_1$-$C_4)$alkylamino, di-$(C_1$-$C_4)$alkylamino, aminosulfonyl, $(C_1$-$C_4)$alkylaminosulfonyl, di-$(C_1$-$C_4)$alkylaminosulfonyl, aminothiocarbonyl, NHCO—$(C_1$-$C_4)$alkyl ($(C_1$-$C_4)$alkylcarbonylamino), $R^6$ is preferably $(C_1$-$C_4)$alkyl, $(C_1$-$C_4)$haloalkyl, $(C_1$-$C_4)$cyanoalkyl, $(C_1$-$C_4)$hydroxyalkyl, $(C_1$-$C_4)$alkoxy-$(C_1$-$C_4)$alkyl, $(C_1$-$C_4)$haloalkoxy-$(C_1$-$C_4)$alkyl, $(C_2$-$C_4)$alkenyl, $(C_2$-$C_4)$alkenyloxy-$(C_1$-$C_4)$alkyl, $(C_2$-$C_4)$haloalkenyloxy-$(C_1$-$C_4)$alkyl, $(C_2$-$C_4)$haloalkenyl, $(C_2$-$C_4)$cyanoalkenyl, $(C_2$-$C_4)$alkynyl, $(C_2$-$C_4)$alkynyloxy-$(C_1$-$C_4)$alkyl, $(C_2$-$C_4)$haloalkynyl, $(C_3$-$C_6)$cycloalkyl, $(C_3$-$C_6)$cycloalkyl-$(C_3$-$C_6)$cycloalkyl, $(C_1$-$C_4)$alkyl-$(C_3$-$C_6)$cycloalkyl, halo$(C_3$-$C_6)$cycloalkyl, $(C_1$-$C_4)$alkylthio-$(C_1$-$C_4)$alkyl, $(C_1$-$C_4)$haloalkylthio-$(C_1$-$C_4)$alkyl, $(C_1$-$C_4)$alkylsulfinyl-$(C_1$-$C_4)$alkyl, $(C_1$-$C_4)$haloalkylsulfinyl-$(C_1$-$C_4)$alkyl, $(C_1$-$C_4)$alkylsulfonyl-$(C_1$-$C_4)$alkyl, $(C_1$-$C_4)$haloalkylsulfonyl-$(C_1$-$C_4)$alkyl, $(C_1$-$C_4)$alkoxy-$(C_1$-$C_4)$alkylthio-$(C_1$-$C_4)$alkyl or $(C_1$-$C_4)$alkylcarbonyl-$(C_1$-$C_4)$alkyl, $R^8$ is preferably amino, in each case optionally singly or multiply, identically or differently substituted $C_1$-$C_4$-alkylamino, di-$(C_1$-$C_4)$-alkylamino, $C_2$-$C_6$-alkenylamino, $C_2$-$C_6$-alkynylamino, $C_3$-$C_{12}$-cycloalkylamino, $C_3$-$C_{12}$-cycloalkyl-$(C_1$-$C_6)$-alkylamino, $C_4$-$C_{12}$-bicycloalkylamino or hydrazino, where the substituents may independently be selected from halogen, cyano, amino, $C_1$-$C_6$-alkyl, $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, a phenyl ring and a 3- to 6-membered aromatic partly saturated or saturated heterocycle, where the phenyl ring or heterocycle may in each case optionally be mono- or polysubstituted identically or differently, and where the substituents may independently be selected from $C_1$-$C_4$-alkyl, $C_1$-$C_4$-haloalkyl, halogen, cyano, $NO_2$, $C_1$-$C_4$-alkoxy or $C_1$-$C_4$-haloalkoxy, or $R^{11}$, $R^{12}$ are preferably independently hydrogen, in each case optionally singly or multiply, identically or differently substituted $C_1$-$C_4$-alkyl or $C_3$-$C_6$-cycloalkyl, where the substituents may independently be selected from halogen, cyano, a phenyl ring and a 3- to 6-membered aromatic partly saturated or saturated heterocycle, where the phenyl ring or heterocycle may in each case optionally be mono- or polysubstituted identically or differently, and where the substituents may independently be selected from $C_1$-$C_4$-alkyl, $C_1$-$C_4$-haloalkyl, halogen, cyano, $NO_2$, $C_1$-$C_4$-alkoxy or $C_1$-$C_4$-haloalkoxy, or $R^{11}$, $R^{12}$ are preferably independently a phenyl ring or a 3- to 6-membered aromatic partly saturated or saturated heterocycle, where the heteroatoms are selected from the group of N, S, O, where the phenyl ring or heterocycle may in each case optionally be mono- or polysubstituted identically or differently, and where the substituents may independently be selected from $C_1$-$C_4$-alkyl, $C_1$-$C_4$-haloalkyl, halogen or cyano, and n is preferably 0, 1 or 2.

Configuration 3:

$A^1$ is more preferably nitrogen or =C($R^5$)—, $A^2$ is more preferably —N($R^6$)—, $R^1$ is more preferably $(C_1$-$C_4)$alkyl, $(C_1$-$C_4)$hydroxyalkyl, $(C_1$-$C_4)$haloalkyl, $(C_2$-$C_4)$alkenyl, $(C_2$-$C_4)$haloalkenyl, $(C_2$-$C_4)$alkynyl, $(C_2$-$C_4)$haloalkynyl, $(C_3$-$C_6)$cycloalkyl, $(C_1$-$C_4)$alkylthio-$(C_1$-$C_4)$alkyl, $(C_1$-$C_4)$alkylsulfinyl-$(C_1$-$C_4)$alkyl or $(C_1$-$C_4)$alkylsulfonyl-$(C_1$-$C_4)$alkyl, $R^2$ is more preferably —C(=O)—$NR^{11}R^{12}$, —C(=S)—$NR^{11}R^{12}$, —$NR^{11}R^{12}$, —$NR^{11}$—C(=O)—$R^8$ or —$NR^{11}$—C(=S)—$R^8$, $R^3$ is more preferably $C_2$-haloalkyl, $R^4$ is more preferably hydrogen, cyano, halogen, nitro, hydroxyl, amino, $(C_3$-$C_6)$cycloalkyl, cyano$(C_3$-$C_8)$-cycloalkyl, $(C_3$-$C_6)$cycloalkyl-$(C_3$-$C_6)$cycloalkyl, $(C_1$-$C_4)$alkyl-$(C_3$-$C_6)$cycloalkyl, halo$(C_3$-$C_6)$cycloalkyl, $(C_1$-$C_4)$alkyl, $(C_1$-$C_4)$haloalkyl, $(C_1$-$C_4)$cyanoalkyl, $(C_1$-$C_4)$alkoxy-$(C_1$-$C_4)$alkyl, $(C_2$-$C_4)$alkenyl, $(C_2$-$C_4)$haloalkenyl, $(C_2$-$C_4)$cyanoalkenyl, $(C_2$-$C_4)$alkynyl, $(C_2$-$C_4)$haloalkynyl, $(C_2$-$C_4)$cyanoalkynyl, $(C_1$-$C_4)$alkoxy, $(C_1$-$C_4)$haloalkoxy, $(C_1$-$C_4)$cyanoalkoxy, $(C_1$-$C_4)$alkylthio, $(C_1$-$C_4)$haloalkylthio, $(C_1$-$C_4)$alkylsulfinyl, $(C_1$-$C_4)$haloalkylsulfinyl, $(C_1$-$C_4)$alkylsulfonyl, $(C_1$-$C_4)$haloalkylsulfonyl, $R^5$ $R^5$ is more preferably hydrogen, halogen, cyano or $(C_1-C_4)$alkyl, $R^6$ is more preferably $(C_1-C_4)$alkyl or $(C_1-C_4)$alkoxy-$(C_1-C_4)$alkyl, $R^8$ is more preferably amino, in each case optionally mono-halogen-, -cyano-, —$C_1$-$C_4$-alkoxy-, —$C_1$-$C_4$-alkylthio-, —$C_1$-$C_4$-alkylsulfinyl-, —$C_1$-$C_4$-alkylsulfonyl-, -phenyl- or -pyridyl-substituted $(C_1-C_4)$alkylamino, di-$(C_1-C_4)$-alkylamino, $(C_2-C_6)$-alkenylamino, $(C_2-C_4)$-alkynylamino, $(C_3-C_6)$-cycloalkylamino, hydrazino, $R^{11}$, $R^{12}$ are more preferably independently hydrogen, in each case optionally mono-halogen-, -cyano-, -phenyl- or -pyridyl-substituted $(C_1-C_4)$alkyl or $(C_3-C_6)$cycloalkyl, and n is more preferably 0, 1 or 2.

Configuration 4:

$A^1$ is even more preferably nitrogen or =C($R^5$)—, $A^2$ is even more preferably —N($R^6$)—, $R^1$ is even more preferably $(C_1-C_4)$alkyl, $(C_1-C_4)$haloalkyl or $(C_3-C_6)$cycloalkyl, $R^2$ is even more preferably —C(=O)—N$R^{11}R^{12}$ where $R^{11}$, $R^{12}$ are even more preferably each independently hydrogen, $(C_1-C_4)$alkyl or $(C_3-C_6)$cycloalkyl or $R^2$ is even more preferably —N$R^{11}$—C(=O)—$R^8$ where $R^8$ is even more preferably $(C_2-C_6)$-alkenylamino, $(C_2-C_4)$-alkynylamino, $(C_3-C_6)$-cycloalkylamino, $(C_1-C_4)$-alkylamino or hydrazino and $R^{11}$ is even more preferably hydrogen, $(C_3-C_6)$cycloalkyl or $(C_1-C_4)$alkyl, $R^3$ is even more preferably fluoroethyl, difluoroethyl, trifluoroethyl, tetrafluoroethyl or pentafluoroethyl, $R^4$ is even more preferably hydrogen, cyano, halogen, $(C_1-C_4)$alkyl, $(C_1-C_4)$haloalkyl, $(C_1-C_4)$haloalkoxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl, $(C_1-C_4)$haloalkylsulfonyl or $(C_1-C_4)$alkylcarbonylamino, $R^5$ is even more preferably hydrogen, fluorine, chlorine, bromine or cyano, $R^6$ is even more preferably methyl, ethyl, i-propyl, methoxymethyl or methoxyethyl and n is even more preferably 0, 1 or 2.

Configuration 5:

$A^1$ is particularly nitrogen, $A^2$ is particularly —NMe, $R^1$ is particularly methyl, ethyl, n-propyl, i-propyl or cyclopropyl, $R^2$ is particularly —C(=O)—N$R^{11}R^{12}$ where $R^{11}$ is particularly hydrogen or $(C_1-C_4)$alkyl and $R^{12}$ is particularly hydrogen, $(C_1-C_4)$alkyl or $(C_3-C_6)$cycloalkyl, or $R^2$ is particularly —N$R^{11}$—C(=O)—$R^8$ where $R^8$ is particularly $(C_1-C_4)$alkylamino or di-$(C_1-C_4)$alkylamino and $R^{11}$ is particularly hydrogen or $(C_1-C_4)$alkyl and $R^3$ is particularly pentafluoroethyl or tetrafluoroethyl (—$CF_2CF_2H$ or $CFHCF_3$), $R^4$ is particularly hydrogen and n is particularly 0 or 2.

Configuration 6:

$A^1$ is especially nitrogen, $A^2$ is especially —NMe, $R^1$ is especially ethyl or methyl, $R^2$ is especially —C(=O)—N$R^{11}R^{12}$ where $R^{11}$ is especially hydrogen or methyl and $R^2$ is especially hydrogen, methyl, cyclopropyl or ethyl or $R^2$ is especially —N$R^{11}$—C(=O)—$R^8$ where $R^8$ is especially methylamino (—NHMe), ethylamino (—NHEt) or dimethylamino (—N(Me)$_2$) and $R^{11}$ is especially hydrogen or methyl and $R^3$ is especially pentafluoroethyl, $R^4$ is especially hydrogen and n is especially 2.

Preference is given to compounds of the formula (I-1)

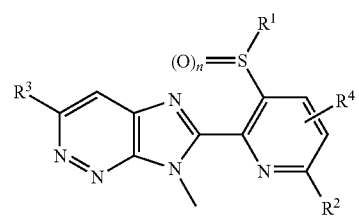

I-1 where $R^1$, $R^2$, $R^3$, $R^4$ and n are as defined in configuration 1, configuration 2, configuration 3, configuration 4, configuration 5 or configuration 6.

Particular preference is given to compounds of the formula (I-2)

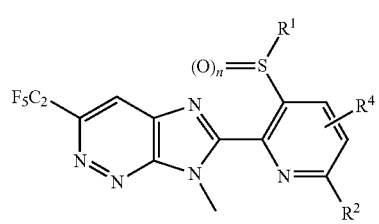

I-2 where $R^1$, $R^2$, $R^4$ and n are as defined in configuration 1, configuration 2, configuration 3, configuration 4, configuration 5 or configuration 6.

The remarks which follow hereinafter relating to the compounds of the formula (I) do of course also apply to the compounds of the formulae (I-1) and (I-2) that are encompassed by formula (I).

Emphasis is given to compounds of the formula (I) in which $R^1$ is $(C_1-C_4)$alkyl, $(C_1-C_4)$haloalkyl or $(C_3-C_6)$cycloalkyl and $A^1$, $A^2$, $R^2$, $R^3$, $R^4$, $R^5$, $R^6$, $R^8$, $R^{11}$, $R^{12}$ and n are as defined in configuration 1, configuration 2, configuration 3, configuration 5 or configuration 6.

Emphasis is further given to compounds of the formula (I) in which $R^1$ is $(C_1-C_4)$alkyl and $A^1$, $A^2$, $R^2$, $R^3$, $R^4$, $R^5$, $R^6$, $R^8$, $R^{11}$, $R^{12}$ and n are as defined in configuration 1, configuration 2, configuration 3, configuration 4 or configuration 6.

Emphasis is further given to compounds of the formula (I) in which $R^1$ is methyl or ethyl and $A^1$, $A^2$, $R^2$, $R^3$, $R^4$, $R^5$, $R^6$, $R^8$, $R^{11}$, $R^{12}$ and n are as defined in configuration 1, configuration 2, configuration 3, configuration 4 or configuration 5.

Emphasis is further given to compounds of the formula (I) in which
$R^1$ is methyl
and $A^1$, $A^2$, $R^2$, $R^3$, $R^4$, $R^5$, $R^6$, $R^8$, $R^{11}$, $R^{12}$ and n are as defined in configuration 1, configuration 2, configuration 3, configuration 4, configuration 5 or configuration 6.

Emphasis is further given to compounds of the formula (I) in which
$R^1$ is ethyl
and $A^1$, $A^2$, $R^2$, $R^3$, $R^4$, $R^5$, $R^6$, $R^8$, $R^{11}$, $R^{12}$ and n are as defined in configuration 1, configuration 2, configuration 3, configuration 4, configuration 5 or configuration 6.

Emphasis is further given to compounds of the formula (I) in which
$R^2$ is —C(=O)—$NR^{11}R^{12}$ where
$R^{11}$, $R^{12}$ are in each case independently hydrogen, $(C_1-C_4)$alkyl or $(C_3-C_6)$cycloalkyl
or
$R^2$ is —$NR^{11}$—C(=O)—$R^8$ where
$R^8$ is $(C_2-C_6)$-alkenylamino, $(C_2-C_4)$-alkynylamino, $(C_3-C_6)$-cycloalkylamino, $(C_1-C_4)$-alkylamino or hydrazino
and
$R^{11}$ is hydrogen, $(C_3-C_6)$cycloalkyl or $(C_1-C_4)$alkyl,
and $A^1$, $A^2$, $R^1$, $R^3$, $R^4$, $R^5$, $R^6$ and n are as defined in configuration 1, configuration 2, configuration 3, configuration 5 or configuration 6.

Emphasis is further given to compounds of the formula (I) in which
$R^2$ is —C(=O)—$NR^{11}R^{12}$
and $A^1$, $A^2$, $R^1$, $R^3$, $R^4$, $R^5$, $R^6$, $R^{11}$, $R^{12}$ and n are as defined in configuration 1, configuration 2, configuration 3, configuration 4, configuration 5 or configuration 6.

Emphasis is further given to compounds of the formula (I) in which
$R^2$ is —$NR^{11}$—C(=O)—$R^8$
and $A^1$, $A^2$, $R^1$, $R^3$, $R^4$, $R^5$, $R^6$, $R^{11}$, $R^{12}$ and n are as defined in configuration 1, configuration 2, configuration 3, configuration 4, configuration 5 or configuration 6.

Emphasis is further given to compounds of the formula (I) in which
$A^2$ is —NMe
and $A^1$, $R^1$, $R^2$, $R^3$, $R^4$, $R^5$, $R^8$, $R^{11}$, $R^{12}$ and n are as defined in configuration 1, configuration 2, configuration 3 or configuration 4.

Emphasis is further given to compounds of the formula (I) in which
$A^1$ is nitrogen
and $A^2$, $R^1$, $R^2$, $R^3$, $R^4$, $R^6$, $R^8$, $R^{11}$, $R^{12}$ and n are as defined in configuration 1, configuration 2, configuration 3 or configuration 4.

Emphasis is further given to compounds of the formula (I) in which
$R^4$ is hydrogen, cyano, halogen, $(C_1-C_4)$alkyl, $(C_1-C_4)$haloalkyl, $(C_1-C_4)$haloalkoxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl, $(C_1-C_4)$haloalkylsulfonyl or $(C_1-C_4)$alkylcarbonylamino
and $A^1$, $A^2$, $R^1$, $R^2$, $R^3$, $R^5$, $R^6$, $R^{11}$, $R^{12}$, $R^8$ and n are as defined in configuration 1, configuration 2, configuration 3, configuration 5 or configuration 6.

Emphasis is further given to compounds of the formula (I) in which
$R^4$ is hydrogen
and $A^1$, $A^2$, $R^1$, $R^2$, $R^3$, $R^5$, $R^6$, $R^{11}$, $R^{12}$, $R^8$ and n are as defined in configuration 1, configuration 2, configuration 3 or configuration 4.

Emphasis is especially given to compounds of the formula (I) in which
$R^3$ is pentafluoroethyl or tetrafluoroethyl (—$CF_2CF_2H$ or $CFHCF_3$)
and $A^1$, $A^2$, $R^1$, $R^2$, $R^4$, $R^5$, $R^6$, $R^{11}$, $R^{12}$, $R^8$ and n are as defined in configuration 1, configuration 2, configuration 3, configuration 4 or configuration 6.

Emphasis is especially further given to compounds of the formula (I) in which
$R^3$ is pentafluoroethyl
and $A^1$, $A^2$, $R^1$, $R^2$, $R^4$, $R^5$, $R^6$, $R^{11}$, $R^{12}$, $R^8$ and n are as defined in configuration 1, configuration 2, configuration 3, configuration 4 or configuration 5.

Especially preferred are the compounds of the formulae (I-a) to (I-o).

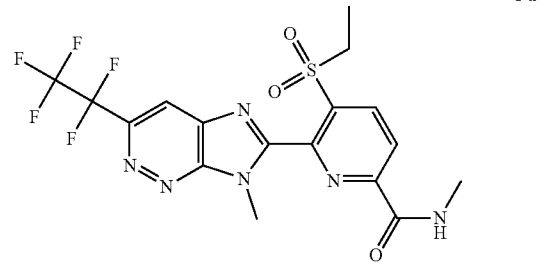

I-a

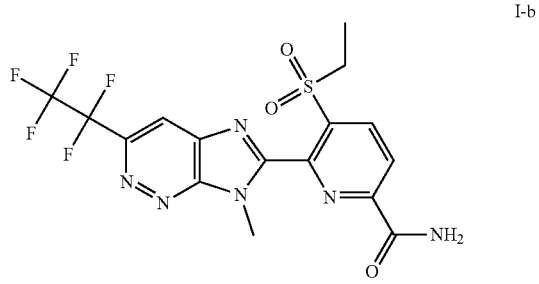

I-b

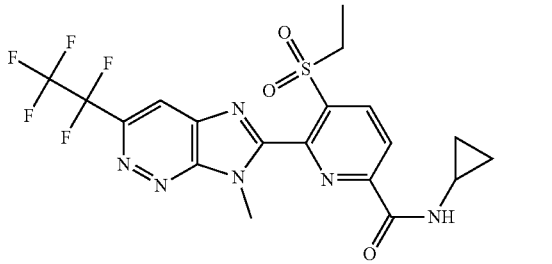

I-c

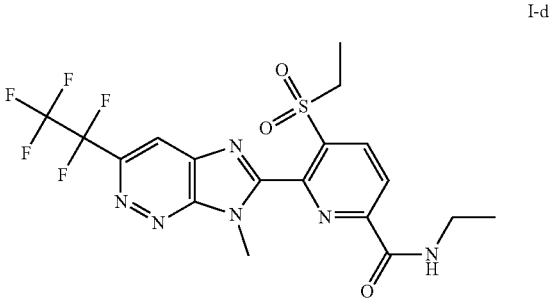

I-d

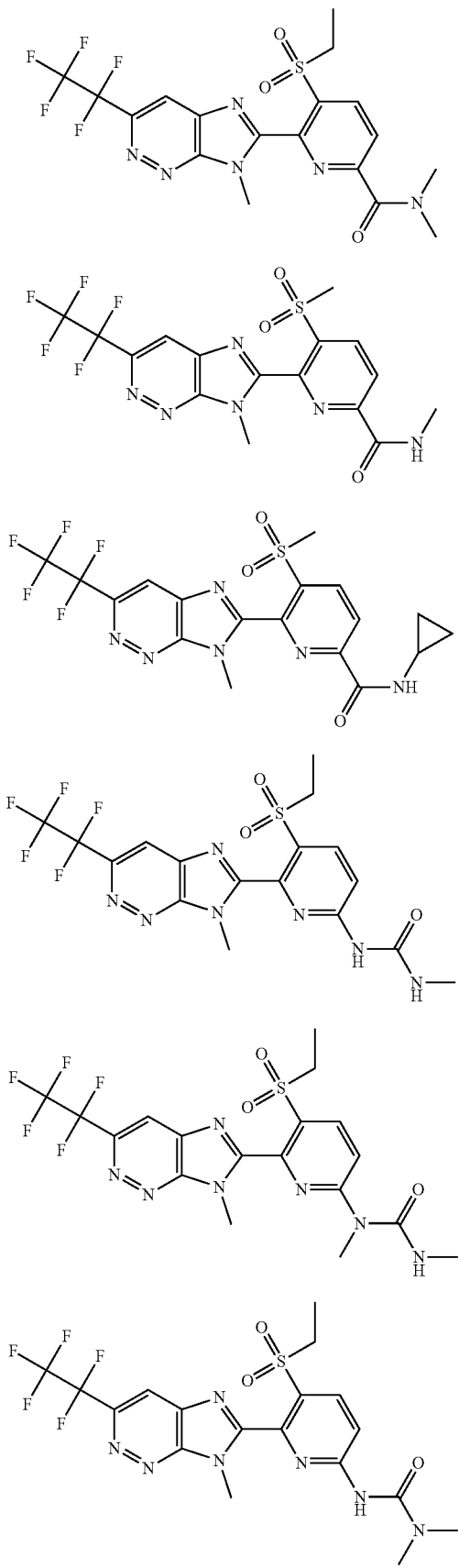
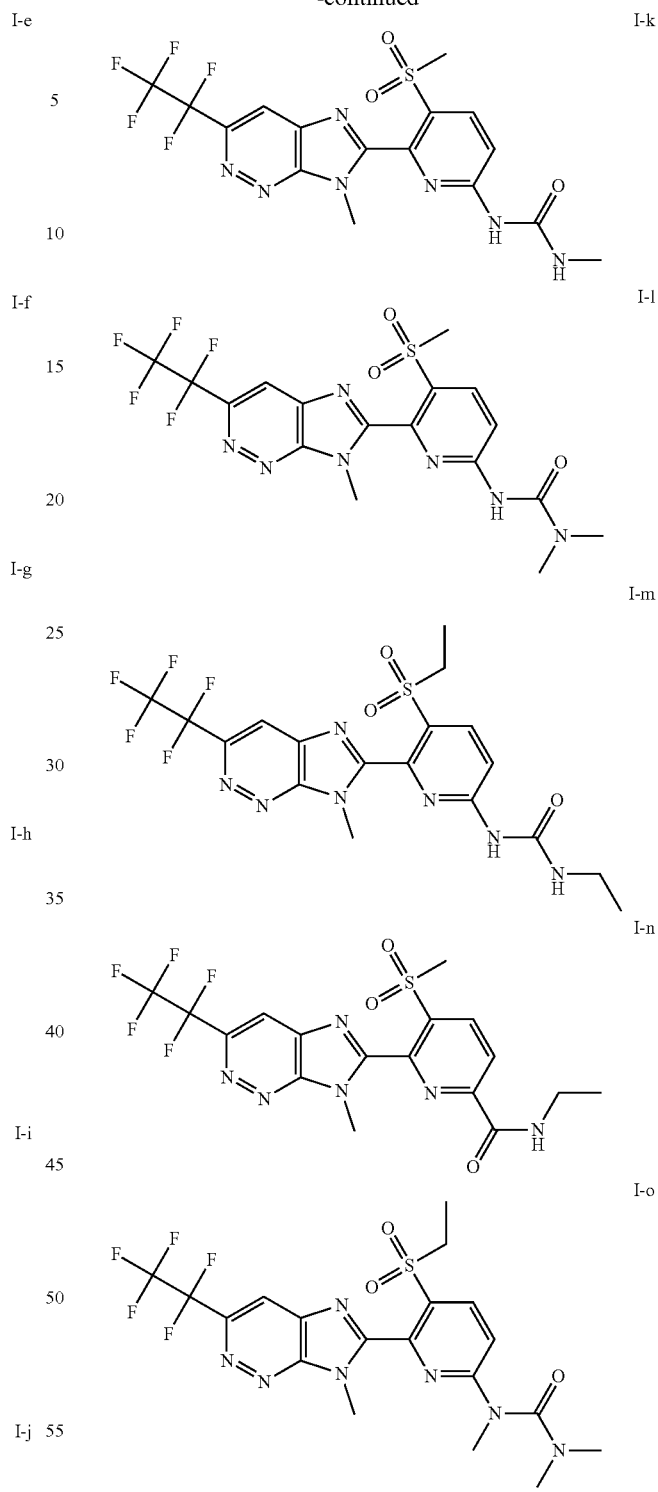

The remarks hereinafter relating to the compounds of the formula (I) do of course also apply to the compounds of the formulae (I-1), (I-2) and (I-a) to (I-o) that are encompassed by formula (I).

In accordance with the definitions, unless stated otherwise, halogen is selected from the group of fluorine, chlorine, bromine and iodine, preferably in turn from the group of fluorine, chlorine and bromine, more preferably of fluorine or chlorine.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. According to the invention, unless defined differently elsewhere, the term "alkynyl", either on its own or else in combination with further terms, is understood to mean a straight-chain or branched $C_2$-$C_{12}$-alkyl radical which has at least one triple bond, for example ethynyl, I-propynyl and propargyl. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl.

The term "alkoxy", either on its own or else in combination with further terms, for example haloalkoxy, is understood in the present case to mean an O-alkyl radical, where the term "alkyl" is as defined above.

Halogen-substituted radicals, especially $C_2$-haloalkyl, are mono- or polyhalogenated, up to the maximum number of possible substituents. In the case of polyhalogenation, the halogen atoms may be identical or different. The halogens (Hal) are selected from the group of fluorine, chlorine, bromine and iodine, preferably in turn from the group of fluorine, chlorine and bromine, more preferably from fluorine and chlorine, and the halogen is especially preferably fluorine.

Preferably, the $C_2$-haloalkyl radical is tri-, tetra- or pentahalogenated, more preferably tetra- or pentahalogenated and most preferably pentahalogenated.

$C_2$-Haloalkyl preferably includes —$CHal_2$-$CHal_3$, —$CHal_2$-$CHal_2H$, —$CHalH$—$CHal_3$, —$CHal_2$-$CH_2Hal$, —$CH_2$—$CHal_3$, —$CHalH$—$CHHal_2$, more preferably —$CHal_2$-$CHal_3$, —$CHal_2$-$CHal_2H$, —$CHalH$-$CHal_3$ and most preferably —$CHal_2$-$CHal_3$.

Emphasis is given here to —$CF_2$—$CF_3$, —$CF_2$—$CF_2H$, —$CFH$—$CF_3$ and most preferably to —$CF_2$—$CF_3$.

According to the invention, unless defined differently elsewhere, the term "aryl" is understood to mean an aromatic radical having 6 to 14 carbon atoms, preferably phenyl, naphthyl, anthryl or phenanthrenyl, more preferably phenyl.

Unless defined differently elsewhere, the term "arylalkyl" is understood to mean a combination of the radicals "aryl" and "alkyl" defined in accordance with the invention, where the radical is generally bonded via the alkyl group; examples of these are benzyl, phenylethyl or α-methylbenzyl, particular preference being given to benzyl.

Unless defined differently elsewhere, "hetaryl" denotes a mono-, bi- or tricyclic heterocyclic group composed of carbon atoms and at least one heteroatom, where at least one ring is aromatic. Preferably, the hetaryl group contains 3, 4, 5, 6, 7 or 8 carbon atoms and is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl, imidazopyridinyl and indolizinyl.

Unless stated otherwise, optionally substituted radicals may be mono- or polysubstituted, where the substituents in the case of poly substitutions may be the same or different.

Depending on the nature of the substituents, the compounds of the formula (I) may take the form of geometric and/or optically active isomers or corresponding isomer mixtures in different compositions. These stereoisomers are, for example, enantiomers, diastereomers, atropisomers or geometric isomers. The invention therefore encompasses pure stereoisomers and any desired mixtures of these isomers.

The compounds of the formula (I) may also be in the form of salts, especially acid addition salts and metal salt complexes. The compounds of the formula (I) and the acid addition salts and metal complexes thereof have good efficacy, especially for control of animal pests.

Suitable salts of the compounds of the general formula (I) include customary nontoxic salts, i.e. salts with appropriate bases and salts with added acids. Preference is given to salts with inorganic bases, such as alkali metal salts, for example sodium, potassium or caesium salts, alkaline earth metal salts, for example calcium or magnesium salts, ammonium salts, salts with organic bases and with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulfates, trihydrosulfates, or phosphates, salts with organic carboxylic acids or organic sulfonic acids, for example formates, acetates, trifluoroacetates, maleates, tartrates, methanesulfonates, benzenesulfonates or para-toluenesulfonates, salts with basic amino acids, for example arginates, aspartates or glutamates, and the like.

The radical definitions or illustrations given in general terms or listed within ranges of preference apply correspondingly to end products and to starting materials and intermediates. These radical definitions can be combined with one another as desired, i.e. including combinations between the respective ranges of preference.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the definitions listed above as being very particularly preferred.

Most preference according to the invention is given to using compounds of the formula (I) which contain a combination of the meanings listed above as being most preferable.

Especially used according to the invention are compounds of the formula (I) which contain a combination of the meanings listed above as being especially emphasized.

Processes:

The inventive compounds of the formula (I) can be obtained by the processes shown in the following schemes:

Process A

The compounds of the formula (I) can be prepared by known methods, for example analogously to the processes described in WO2017/025419.

The radicals $A^1$, $R^3$, $R^4$, $R^8$ and $R^{11}$ have the definitions described above. $X^1$ and $X^2$ are halogen.

Step a)

The compounds of the formula (I) can be prepared in analogy to the process described in U.S. Pat. No. 5,374,646 or Bioorganic and Medicinal Chemistry Letters 2003, 13, 1093-1096 by reacting compounds of the formula (II) with an ammonia source in the presence of a condensing agent. The preparation of compounds of the formula (IV) where $R^6$=H and $R^5$=trifluoromethyl is described in WO 2016/039441.

Carboxylic acids of the formula (II) are either commercially available or can be prepared by known methods, for example analogously to the processes described in US 2010/234604, WO 2012/061926 or Bioorganic and Medicinal Chemistry Letters, 18 (2008), 5023-5026.

The reaction of the compounds of the formula (I) with the ammonia source is preferably carried out in a solvent

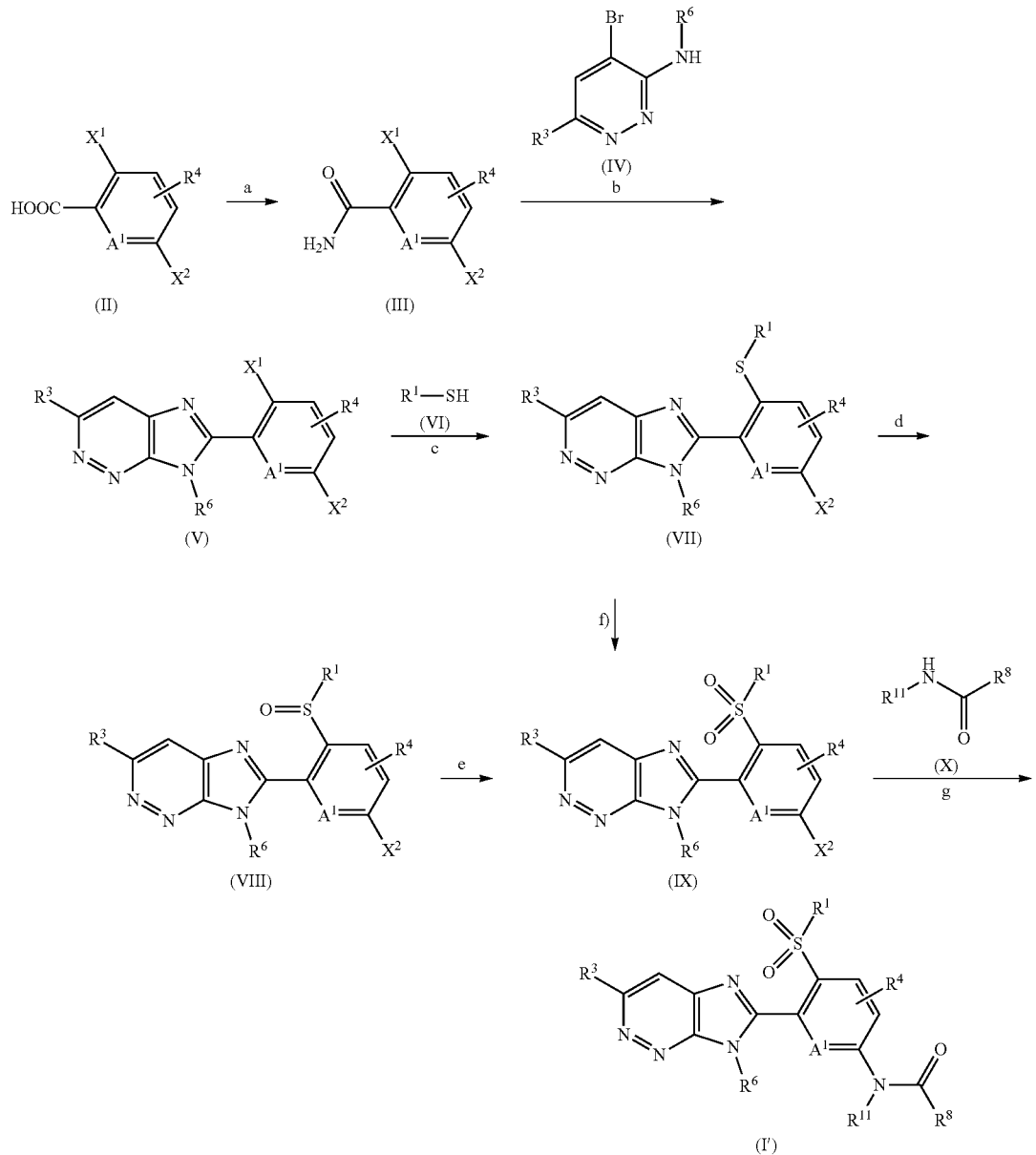

selected from customary solvents which are inert under the prevailing reaction conditions. Preference is given to ethers, for example dioxane or tetrahydrofuran.

A suitable condensing agent is, for example, carbonyldiimidazole.

The reaction can be carried out under reduced pressure, at atmospheric pressure or under elevated pressure. Preferably, the reaction is carried out at atmospheric pressure and temperatures from 20 to 70° C.

Step b)

The compounds of the formula (V) can be prepared in analogy to the process described in WO 2017/025419 and WO 2014/142292 by reacting compounds of the formula (III) with compounds of the formula (IV) in the presence of a palladium catalyst in basic media.

Compounds of the formula (IV) can be prepared, for example, analogously to the processes described in WO 2014/142292. A palladium catalyst used may, for example, be [1,1'-bis-(diphenylphosphino)ferrocene]dichloropalladium(II). Frequently, the bases used are inorganic bases such as potassium tert-butoxide.

The reaction is carried out in a solvent. Frequently, toluene is used.

The reaction can be carried out under reduced pressure, at atmospheric pressure or under elevated pressure. Preferably, the reaction is carried out at atmospheric pressure and temperatures from 20 to 110° C.

Step c)

The compounds of the formula (VII) can be prepared by reacting the compounds of the formula (V) with the compounds of the formula (VI) in the presence of a base.

Mercaptan derivatives of the formula (VI), for example methyl mercaptan, ethyl mercaptan or isopropyl mercaptan, are either commercially available or can be prepared by known methods, for example analogously to the processes described in US 2006/0025633, US 2006/111591, U.S. Pat. No. 2,820,062, Chemical Communications, 13 (2000), 1163-1164 or Journal of the American Chemical Society, 44 (1922), p. 1329.

The conversion to compounds of the formula (VII) can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulfoxide.

Examples of suitable bases are inorganic bases from the group consisting of acetates, phosphates and carbonates of alkali metals or alkaline earth metals. Preference is given here to caesium carbonate, sodium carbonate and potassium carbonate. Further suitable bases are alkali metal hydrides, for example sodium hydride.

The reaction can be conducted under reduced pressure, standard pressure or under elevated pressure, and at temperatures of 0° C. to 200° C.

Step d)

The compounds of the formula (VIII) can be prepared by oxidizing the compounds of the formula (VII). The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be conducted under reduced pressure, at standard pressure or under elevated pressure, and at temperatures of −20° C. to 120° C.

Step e)

The compounds of the formula (IX) can be prepared by oxidizing the compounds of the formula (VIII). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Step f)

The compounds of the formula (IX) can also be prepared in a one-step process by oxidizing the compounds of the formula (VII). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Step g)

The compounds of the formula (I') can be prepared in a one-stage process by reacting the compounds of the formula (IX) with compounds of the formula (X) in analogy to the processes described in Synthesis, (2005), 915-924 or Organic Letters, 11 (2009), 947-950.

Compounds of the formula (X) are either commercially available or can be prepared by known methods, for example analogously to the processes described in Houben-Weyl Methoden der Organischen Chemie volume XVI/2, $4^{th}$ edition.

The conversion to compounds of the formula (I') is generally conducted in a solvent in the presence of a base. Preferred solvents are ethers, for example dioxane or ethylene glycol dimethyl ether; preferred bases are, for example, caesium carbonate, potassium phosphate or sodium tert-butoxide.

The conversion to compounds of the formula (I') is generally conducted in the presence of a catalyst and a ligand. Catalysts used may be palladium complexes, for example tris(dibenzylideneacetone)dipalladium(0) or palladium acetate, and ligands used are generally organophosphine compounds, for example bis(diphenylphosphine)-9,9-dimethylxanthene (Xantphos).

Process B

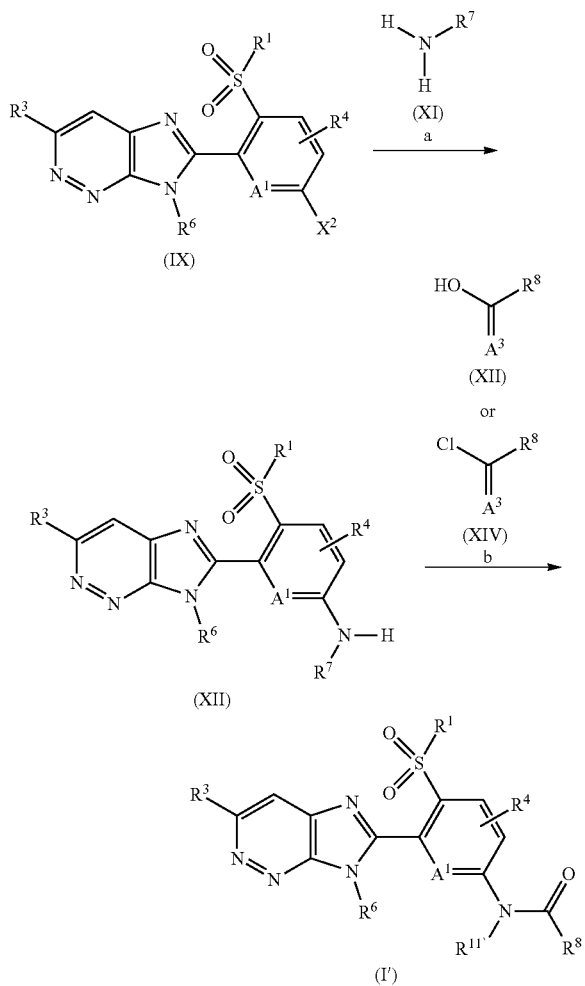

Step a)

The compounds of the formula (XII) can be prepared by reacting the compounds of the formula (IX) with compounds of the formula (XI).

Compounds of the formula (XI) are either commercially available or can be prepared by known methods.

The conversion to compounds of the formula (XII) is generally effected in a solvent. Preference is given to ethers, for example tetrahydrofuran, methyl tert-butyl ether, dioxane, ethylene glycol dimethyl ether, aliphatic hydrocarbons such as hexane, heptane, aromatic hydrocarbons such as toluene, xylene, halogenated hydrocarbons, for example dichloromethane, chloroform, carbon tetrachloride, 1,2-dichloroethane or chlorobenzene, aprotic polar solvents, for example N,N-dimethylformamide, N-methylpyrrolidone, dimethyl sulfoxide, esters, for example ethyl acetate, or nitriles such as acetonitrile.

The reaction can be conducted in the presence of a base. Examples of suitable bases are nitrogen-containing heterocycles such as pyridine, picoline, 2,6-lutidine, 1,8-diazabicyclo[5.4.0]-7-undecene (DBU); tertiary amines such as triethylamine and N,N-diisopropylethylamine, or inorganic bases such as potassium phosphate, potassium carbonate and sodium hydride.

Step b)

The compounds of the formula (I') can be prepared by reacting the compounds of the formula (XIII) with compounds of the formula (XII).

Compounds of the formula (XIII) are either commercially available or can be prepared by known methods.

The conversion to compounds of the formula (I') is generally effected in a solvent. Preference is given to ethers, for example tetrahydrofuran, methyl tert-butyl ether, dioxane, ethylene glycol dimethyl ether, halogenated hydrocarbons, for example dichloromethane, chloroform, carbon tetrachloride, 1,2-dichloroethane or chlorobenzene, aromatic hydrocarbons such as toluene, xylene, esters, for example ethyl acetate, nitriles such as acetonitrile, aprotic polar solvents, for example N,N-dimethylformamide, N-methylpyrrolidone, dimethyl sulfoxide, or nitrogen-containing heterocycles such as pyridine or quinoline.

The reaction can be conducted in the presence of a condensing agent. Examples of suitable condensing agents are carbodiimides such as 1-(3-dimethylaminopropyl)-3-ethylcarbodiimide hydrochloride (EDCI) or 1,3-dicyclohexylcarbodiimide.

The reaction can be conducted in the presence of a suitable catalyst. An example of a suitable catalyst is 1-hydroxybenzotriazole.

The compounds of the formula (I') can also be prepared by reacting the compounds of the formula (XIV) with compounds of the formula (XII).

Compounds of the formula (XIV) are either commercially available or can be prepared by known methods.

The conversion to compounds of the formula (I') is generally effected in a solvent. Preference is given to ethers, for example tetrahydrofuran, methyl tert-butyl ether, dioxane, ethylene glycol dimethyl ether, aliphatic hydrocarbons such as hexane, heptane, aromatic hydrocarbons such as toluene, xylene, halogenated hydrocarbons, for example dichloromethane, chloroform, carbon tetrachloride, 1,2-dichloroethane or chlorobenzene, aprotic polar solvents, for example N,N-dimethylformamide, N-methylpyrrolidone, dimethyl sulfoxide, esters, for example ethyl acetate, or nitriles such as acetonitrile.

The reaction can be conducted in the presence of a base. Examples of suitable bases are nitrogen-containing heterocycles such as pyridine, dimethylaminopyridine, picoline, 2,6-lutidine, 1,8-diazabicyclo[5.4.0]-7-undecene (DBU); tertiary amines such as triethylamine and N,N-diisopropylethylamine, or inorganic bases such as potassium carbonate and sodium hydride.

The reaction according to steps a) and b) can also proceed from compounds of the formula (VII) or of the formula (VIII).

Process C

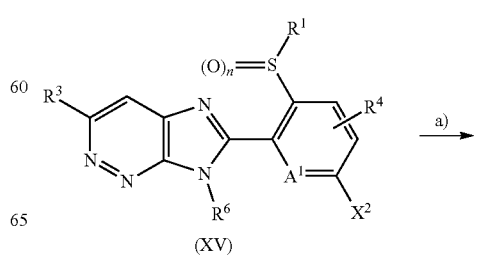

-continued

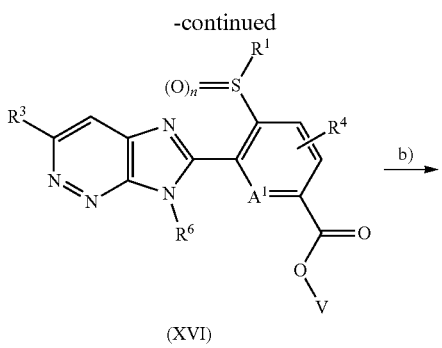

(XVI)

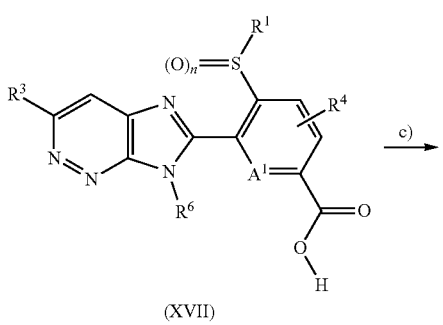

(XVII)

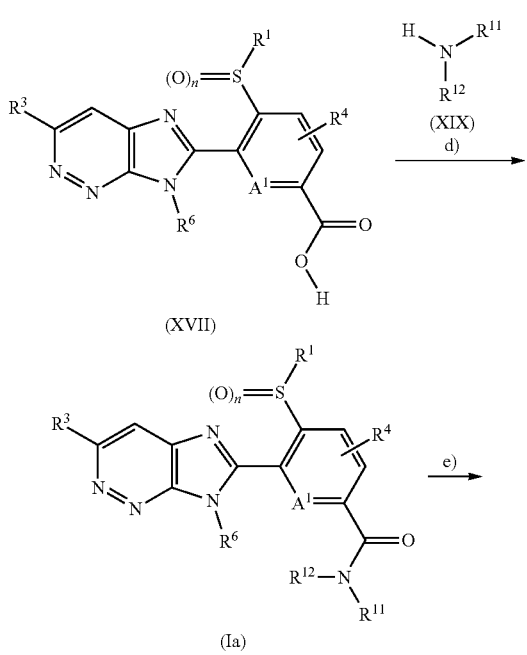

(Ia)

-continued

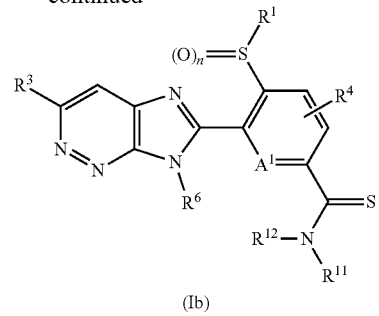

(Ib)

The radicals R¹, R³, R⁴, R⁶, R¹¹, R¹², A¹ and n have the definitions described above; V is $(C_1-C_4)$alkyl.

Step a)

Compounds of the formula (Ia or Ib) for which $R^2$ is a C-bonded carbonamide or thioamide can be prepared, for example, by carbonylation of the compounds of the formula (XV) analogously to S. A. Vinogradov, D. F. Wilson, Tetrahedron Letters, 39 (1998), 8935-8938. The V radical is preferably methyl, ethyl, n-propyl or n-butyl. Catalysts that can be used for the reaction are palladium-phosphine complexes, for example a catalyst composed of palladium chloride, triphenylphosphine and DPPP (1,3-bis(diphenylphosphino)propane) (1:1:1). Preferred bases are, for example, Hünig's base (diisopropylethylamine) or DBU (1,8-diazabicyclo(5.4.0)undec-7-ene).

Step b, c, d)

The ester of the formula (XVI) can initially be converted to the acid of the formula (XV) using standard methods (cf. DE 2221647), for example with an alkali metal hydroxide such as sodium hydroxide or lithium hydroxide as base, in an alcohol as solvent, for example ethanol or a mixture of tetrahydrofuran and water.

Subsequently, the acid of the formula (XVII) is converted by standard methods to the acid chloride of the formula (XVIII), for example with a chlorinating reagent such as thionyl chloride or oxalyl chloride.

The further reaction with the amine of the formula (XIX), in a diluent such as dichloromethane or tetrahydrofuran, for example, and in the presence of a base such as triethylamine or diisopropylethylamine, for example, leads to inventive compounds of the formula (Ia).

Compounds of the formula (XIX) are either commercially available or can be prepared by known methods.

Step e)

Thioamides of the formula (Ib) can be prepared from the carbonamides of the formula (Ia), by reaction with a thionating reagent, for example Lawesson's reagent or $P_4S_{10}$.

Process D

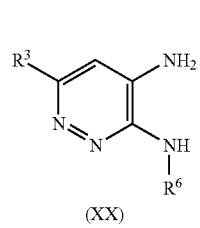

(XX)

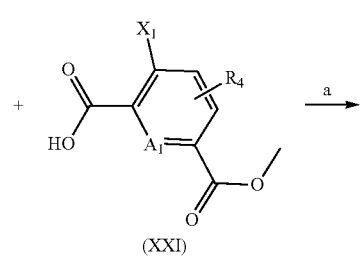

(XXI)

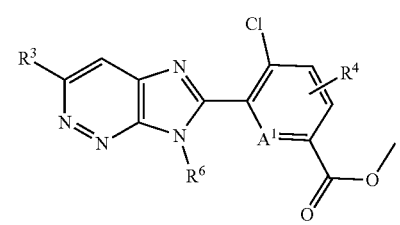

(XXII)

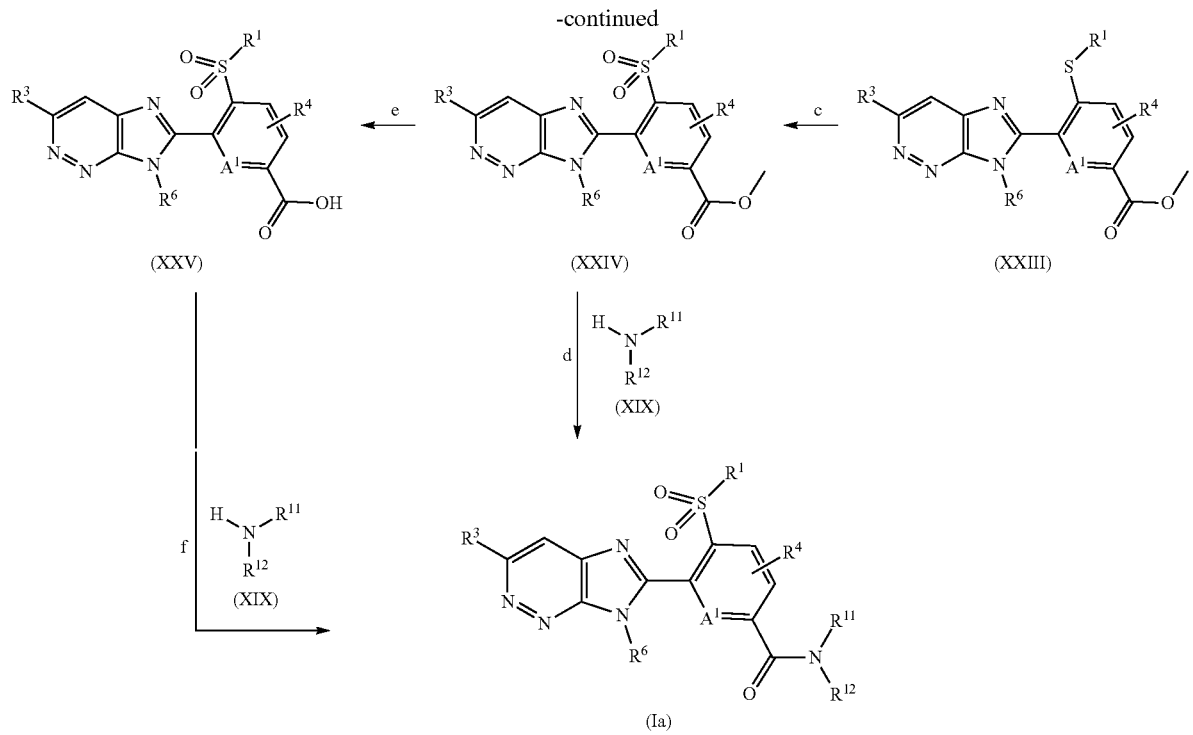

(XXV) (XXIV) (XXIII) (Ia)

The radicals $R^1$, $R^3$, $R^6$, $R^{11}$, $R^{12}$, $A^1$ have the definitions described above.

Step a)

Analogously to process A step a) and b), proceeding from compounds of the formula (XXI) rather than of the formula (III), it is possible to form compounds of the formula (XXII).

Compounds of the formula (XXI) are either commercially available or can be prepared by known methods; see, for example, European Journal of Medicinal Chemistry, 90 (2015), 170.

Step b)

Compounds of the formula (XXII) can be converted to the sulfide of the formula (XXIII) analogously to process A, step c).

Step c)

Compounds of the formula (XXIII) can be oxidized to the sulfone of the formula (XXIV) analogously to process A step f).

Step d)

In the case that $R^{11}$=H and $R^{12}$=alkyl (preferably methyl) or cycloalkyl or H, it is possible to convert compounds of the formula (XXIV) directly to compounds of the formula (Ia) by reaction with an appropriate amine of the formula (XIX) in a suitable solvent and optionally in the presence of a catalyst, for example $MgCl_2$. In this regard see, for example, WO 2004/037789, US 2003/144278 or US 2013/0035492.

Step e)

As an alternative to step d), compounds of the formula (XXIV) can be hydrolysed to the acid (compounds of the formula (XXV)) by methods that are common knowledge.

Step f)

For the conversion to the amide of the formula (Ia) proceeding from compounds of the formula (XXV), a multitude of methods are available. Reference is made by way of example to generally standard methods for preparing amides from acids in the presence of a condensing agent, for example of a carbodiimide such as 1-(3-dimethylaminopropyl)-3-ethylcarbodiimide hydrochloride (EDCI) or 1,3-dicyclohexylcarbodiimide (CDI), and of a base, for example N,N-dimethylpyridine-4-amine (DMAP).

Process E

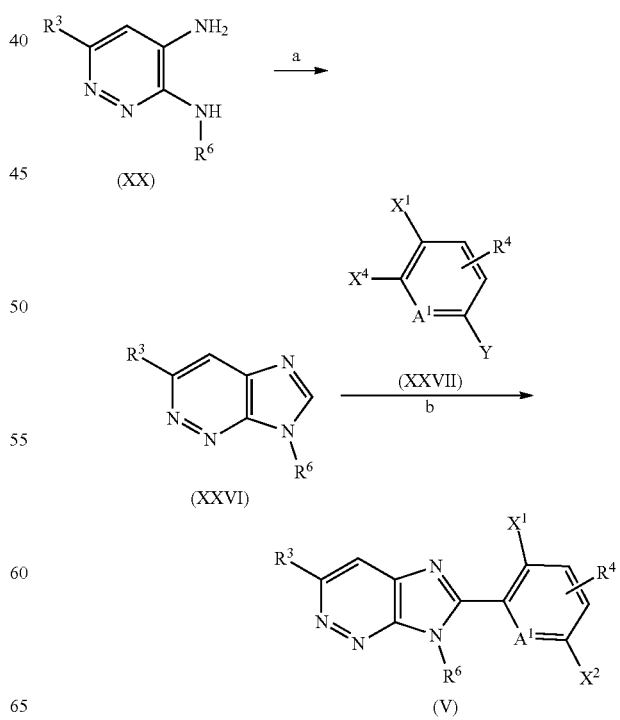

(XX) (XXVI) (V)

The radicals $R^3$, $R^4$ and $R^6$ have the definitions described above. $X^1$ is halogen. Y is halogen or C(=O)OMe.

Step a)

The compounds of the formula (XXVI) can be prepared by reacting the compounds of the formula (XX) with formic acid, for example in analogy to Tetrahedron Letters, 53 (2012), 1036-1041.

Compounds of the formula (XX) can be prepared by known methods as, for example, in WO 2016/039441 and WO 2016/039444.

The conversion to compounds of the formula (XXVI) is generally effected in formic acid as solvent, as described, for example, in Tetrahedron Letters, 53 (2012), 1036-1041 and WO 2010/027500, or in triethyl orthoformate as described in WO 2014/091368.

The reaction can be conducted under reduced pressure, at standard pressure or under elevated pressure and at temperatures of 0° C. to 200° C.

Step b)

The compounds of the formula (V) can be prepared by reacting the compounds of the formula (XXVI) with compounds of the formula (XXVII) in analogy to Organic Letters, 11 (2009), 1837-1840.

Compounds of the formula (XXVII) and their analogues can be prepared by known methods in analogy to Organic Letters, 18 (2016), 5118-5121.

The conversion to compounds of the formula (V) is generally effected in a solvent. Preference is given to ethers, for example tetrahydrofuran, methyl tert-butyl ether, dioxane, ethylene glycol dimethyl ether, aliphatic hydrocarbons such as hexane, heptane, aromatic hydrocarbons such as toluene, xylene, halogenated hydrocarbons, for example dichloromethane, chloroform, carbon tetrachloride, 1,2-dichloroethane or chlorobenzene, aprotic polar solvents, for example N,N-dimethylformamide, N-methylpyrrolidone, dimethyl sulfoxide, esters, for example ethyl acetate, or nitriles such as acetonitrile.

The reaction can be conducted in the presence of a base. Examples of suitable bases are commercially available organozinc bases such as TMPZnCl.LiCl, as described in Organic Letters, 11 (2009), 1837-1840.

The reaction is also effected in the presence of a palladium compound or a nickel compound catalyst such as tetrakis(triphenylphosphine)palladium(0), abbreviated to Pd(PPh$_3$)$_4$.

The reaction can be conducted under reduced pressure, at standard pressure or under elevated pressure and at temperatures of 0° C. to 200° C.

Process F

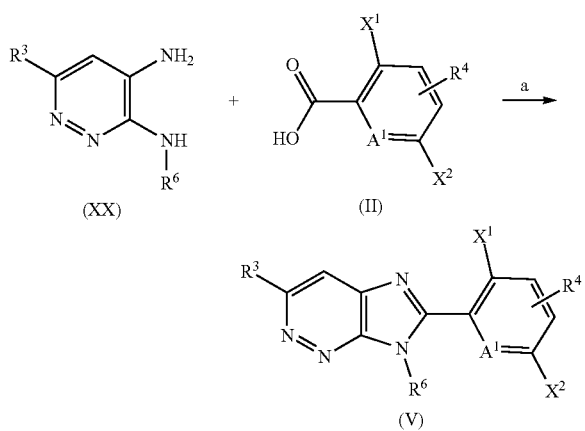

The radicals $R^3$, $R^4$, $R^6$, $A^1$, $X^1$ and $X^2$ have the definitions described above.

Step a)

The compounds of the formula (XX) can be prepared as described in WO 2016/039441.

Carboxylic acids of the formula (II) are either commercially available or can be prepared by known methods, for example analogously to the processes described in US 2010/234604, WO 2012/061926 or Bioorganic and Medicinal Chemistry Letters, 18 (2008), 5023-5026.

The reaction of the compounds of the formula (II) with (XX) is effected in analogy to WO 2016/039441.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection compositions.

In the context of the present application, the term "pesticide" in each case also always encompasses the term "crop protection composition".

The compounds of the formula (I), given good plant tolerance, favourable endotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are carried out on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) can preferably be used as pesticides. They are active against normally sensitive and resistant species and also against all or specific stages of development. The abovementioned pests include:

pests from the phylum of the Arthropoda, especially from the class of the Arachnida, for example *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, e.g. *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agrilus* spp., for example *Agrilus planipennis, Agrilus coxalis, Agrilus bilineatus, Agrilus anxius, Agriotes* spp., for example *Agriotes linneatus, Agriotes mancus, Alphitobius diaperinus, Amphimallon solstitialis, Anobium punctatum, Anoplophora* spp., for example *Anoplophora glabripennis, Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealundica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus fumissi, Dendroctonus* spp., for example *Dendroctonus ponderosae, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Limonius ectypus, Lissorhoptrus oryzophilus, Listronotus* (=*Hyperodes*) spp., *Lixus* spp., *Luperodes* spp., *Luperomorpha xanthodera, Lyctus* spp., *Megacyllene* spp., for example *Megacyllene robiniae, Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., for example *Scolytus multistriatus, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Stemechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda;* from the order of the Hemiptera, for example *Acizzia acaciaebaileyanae, Acizzia dodonaeae, Acizzia uncatoides, Acrida turrita, Acyrthosipon* spp., e.g. *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., e.g. *Amrasca bigutulla, Amrasca devastans, Anuraphis cardui, Aonidiella* spp., e.g. *Aonidiella aurantii, Aonidiella citrina, Aonidiella inornata, Aphanostigma piri, Aphis* spp., e.g. *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., e.g. *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., e.g. *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., e.g. *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., e.g. *Dysaphis apiifolia, Dysaphis plantaginea, Dysaphis tulipae, Dysmicoccus* spp., *Empoasca* spp., e.g. *Empoasca abrupta, Empoasca fabae, Empoasca maligna, Empoasca solana, Empoasca stevensi, Eriosoma* spp., e.g. *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., e.g. *Icerya purchasi, Idiocerus* spp., *Idioscopus* spp., *Laodelphax striatellus, Lecanium* spp., e.g. *Lecanium corni* (=*Parthenolecanium corni*), *Lepidosaphes* spp., e.g. *Lepidosaphes ulmi, Lipaphis erysimi, Lopholeucaspis japonica, Lycorma delicatula, Macrosiphum* spp., e.g. *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., e.g. *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., e.g. *Nephotettix cincticeps, Nephotettix nigropictus, Nettigonicilla spectra, Nilaparvata lugens, Oncometopia* spp., *Orthezia praelonga, Oxya chinensis, Pachypsylla* spp., *Parabemisia myricae, Paratrioza* spp., e.g. *Paratrioza cockerelli, Parlatoria* spp., *Pemphigus* spp., e.g. *Pemphigus bursarius, Pemphigus populivenae, Peregrinus maidis, Perkinsiella* spp., *Phenacoccus* spp., e.g. *Phenacoccus madeirensis, Phloeomyzus passerinii, Phorodon humuli, Phylloxera* spp., e.g. *Phylloxera devastatrix, Phylloxera notabilis, Pinnaspis aspidistrae, Planococcus* spp., e.g. *Planococcus citri, Prosopidopsylla flava, Protopulvinaria pyriformis, Pseudaulacaspis pentagona, Pseudococcus* spp., e.g. *Pseudococcus calceolariae, Pseudococcus comstocki, Pseudococcus longispinus, Pseudococcus maritimus, Pseudococcus viburni, Psyllopsis* spp., *Psylla* spp., e.g. *Psylla buxi, Psylla mali, Psylla pyri, Pteromalus* spp., *Pulvinaria* spp., *Pyrilla* spp., *Quadraspidiotus* spp., e.g. *Quadraspidiotus juglansregiae, Quadraspidiotus ostreaeformis, Quadraspidiotus perniciosus, Quesada gigas, Rastrococcus* spp., *Rhopalosiphum* spp., e.g. *Rhopalosiphum maidis, Rhopalosiphum oxyacanthae, Rhopalosiphum padi, Rhopalosiphum rufiabdominale, Saissetia* spp., e.g. *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., e.g. *Toxoptera aurantii, Toxoptera citricidus, Trialeurodes vaporariorum, Trioza* spp., e.g. *Trioza diospyri, Typhlocyba* spp., *Unaspis* spp., *Viteus vitifolii, Zygina* spp.; from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., e.g. *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., e.g. *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., e.g. *Lygocoris pabulinus, Lygus* spp., e.g. *Lygus elisus, Lygus*

*hesperus, Lygus lineolaris, Macropes excavatus, Megacopta cribraria, Miridae, Monalonion atratum, Nezara* spp., e.g. *Nezara viridula, Nysius* spp., *Oebalus* spp., *Pentomidae, Piesma quadrata, Piezodorus* spp., e.g. *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., e.g. *Athalia rosae, Atta* spp., *Camponotus* spp., *Dolichovespula* spp., *Diprion* spp., e.g. *Diprion similis, Hoplocampa* spp., e.g. *Hoplocampa cookei, Hoplocampa testudinea, Lasius* spp., *Linepithema (Iridiomyrmex) humile, Monomorium pharaonis, Paratrechina* spp., *Paravespula* spp., *Plagiolepis* spp., *Sirex* spp., e.g. *Sirex noctilio, Solenopsis invicta, Tapinoma* spp., *Technomyrmex albipes, Urocerus* spp., *Vespa* spp., e.g. *Vespa crabro, Wasmannia auropunctata, Xeris* spp.;

from the order of the Isopoda, for example *Armadillidium vulgare, Oniscus asellus, Porcellio scaber;* from the order of the Isoptera, for example *Coptotermes* spp., e.g. *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., e.g. *Reticulitermes flavipes, Reticulitermes hesperus;* from the order of the Lepidoptera, for example *Achroia grisella, Acronicta major, Adoxophyes* spp., e.g. *Adoxophyes orana, Aedia leucomelas, Agrotis* spp., e.g. *Agrotis segetum, Agrotis ipsilon, Alabama* spp., e.g. *Alabama argillacea, Amyelois transitella, Anarsia* spp., *Anticarsia* spp., e.g. *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., e.g. *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., e.g. *Cydia nigricana, Cydia pomonella, Dalaca noctuides, Diaphania* spp., *Diparopsis* spp., *Diatraea saccharalis, Dioryctria* spp., e.g. *Dioryctria zimmermani, Earias* spp., *Ecdytolopha aurantium, Elasmopalpus lignosellus, Eldana saccharina, Ephestia* spp., e.g. *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., e.g. *Euproctis chrysorrhoea, Euxoa* spp., *Feltia* spp., *Galleria mellonella, Gracillaria* spp., *Grapholitha* spp., e.g. *Grapholita molesta, Grapholita prunivora, Hedylepta* spp., *Helicoverpa* spp., e.g. *Helicoverpa armigera, Helicoverpa zea, Heliothis* spp., e.g. *Heliothis virescens, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., e.g. *Leucoptera coffeella, Lithocolletis* spp., e.g. *Lithocolletis blancardella, Lithophane antennata, Lobesia* spp., e.g. *Lobesia botrana, Loxagrotis albicosta, Lymantria* spp., e.g. *Lymantria dispar, Lyonetia* spp., e.g. *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., e.g. *Ostrinia nubilalis, Panolis flammea, Parnara* spp., *Pectinophora* spp., e.g. *Pectinophora gossypiella, Perileucoptera* spp., *Phthorimaea* spp., e.g. *Phthorimaea operculella, Phyllocnistis citrella, Phyllonorycter* spp., e.g. *Phyllonorycter blancardella, Phyllonorycter crataegella, Pieris* spp., e.g. *Pieris rapae, Platynota stultana, Plodia interpunctella, Plusia* spp., *Plutella xylostella (=Plutella maculipennis), Podesia* spp., e.g. *Podesia syringae, Prays* spp., *Prodenia* spp., *Protoparce* spp., *Pseudaletia* spp., e.g. *Pseudaletia unipuncta, Pseudoplusia includens, Pyrausta nubilalis, Rachiplusia nu, Schoenobius* spp., e.g. *Schoenobius bipunctifer, Scirpophaga* spp., e.g. *Scirpophaga innotata, Scotia segetum, Sesamia* spp., e.g. *Sesamia inferens, Sparganothis* spp., *Spodoptera* spp., e.g. *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or *Saltatoria*, for example *Acheta domesticus, Dichroplus* spp., *Gryllotalpa* spp., e.g. *Gryllotalpa gryllotalpa, Hieroglyphus* spp., *Locusta* spp., e.g. *Locusta migratoria, Melanoplus* spp., e.g. *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., e.g. *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., e.g. *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., e.g. *Thrips palmi, Thrips tabaci;* from the order of the Zygentoma (=*Thysanura*), for example *Ctenolepisma* spp., *Lepisma saccharina, Lepismodes inquilinus, Thermobia domestica;* from the class of the Symphyla, for example *Scutigerella* spp., e.g. *Scutigerella immaculata;* pests from the phylum of the Mollusca, for example from the class of the Bivalvia, e.g. *Dreissena* spp.; and also from the class of the Gastropoda, for example *Arion* spp., e.g. *Arion ater rufus, Biomphalaria* spp., *Bulinus* spp., *Deroceras* spp., e.g. *Deroceras laeve, Galba* spp., *Lymnaea* spp., *Oncomelania* spp., *Pomacea* spp., *Succinea* spp.;

plant pests from the phylum of the Nematoda, i.e. plant-parasitic nematodes, in particular *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella*

*rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hirschmaniella* spp., *Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Paratylenchus* spp., *Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema index.*

The compounds of the formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). They can, as the case may be, also be used as intermediates or precursors for the synthesis of other active ingredients.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further active agrochemical ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulfoxide, and water.

In principle, it is possible to use all suitable carriers. Suitable carriers include more particularly the following: e.g. ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and hence to increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active ingredients specified here with their common names are known and are described for example in "The Pesticide Manual", 16th ed., British Crop Protection Council 2012, or can be searched for on the Internet (e.g. http:// www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, for example spinosyns, e.g. spinetoram and spinosad.

(6) Glutamate-gated chloride channel (GluCl) allosteric modulators, for example avermectins/milbemycins, e.g. abamectin, emamectin benzoate, lepimectin and milbemectin.

(7) Juvenile hormone mimetics, for example juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulfuryl fluoride or borax or tartar emetic or methyl isocyanate generator, e.g. diazomet and metam.

(9) Chordotonal organ modulators, e.g. pymetrozine or flonicamide.

(10) Mite growth inhibitors, for example clofentezine, hexythiazox and diflovidazin or etoxazole.

(11) Microbial disruptors of the insect midgut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis* and B.t. plant proteins: Cry1Ab, Cry1Ac, Cry1Fa, Cry1A.105, Cry2Ab, Vip3A, mCry3A, Cry3Ab, Cry3Bb, Cry34 Ab1/35Ab1.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists, for example chromafenozide, halofenozide, methoxyfenozide and tebufenozide.

(19) Octopamine receptor agonists, for example amitraz.

(20) Mitochondrial complex III electron transport inhibitors, for example hydramethylnon or acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spirodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilides, for example pyflubumide.

(28) Ryanodine receptor modulators, for example diamides, e.g. chlorantraniliprole, cyantraniliprole and flubendiamide, further active ingredients, for example afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyrifluquinazon, pyriminostrobin, spirobudiclofen, tetramethylfluthrin, tetraniliprole, tetrachlorantraniliprole, tioxazafen, thiofluoximate, triflumezopyrim and iodomethane; additionally preparations based on *Bacillus firmus* (I-1582, BioNeem, Votivo), and the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO 2006/043635) (CAS 885026-50-6), {1'-[(2E)-3-(4-chlorophenyl)prop-2-en-1-yl]-5-fluorospiro[indole-3,4'-piperidine]-1(2H)-yl}(2-chloropyridin-4-yl)methanone (known from WO 2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO 2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO 2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO 2012/029672) (CAS 1363400-41-2), (3E)-3-[1-[(6-chloro-3-pyridyl)methyl]-2-pyridylidene]-1,1,1-trifluoropropan-2-one (known from WO 2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO 2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl) benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]propanamide, (+)-N-[3-chloro-1-(3-pyridinyl)-1H-pyrazol-4-yl]-N-ethyl-3-[(3,3,3-trifluoropropyl)sulfinyl]propanamide and (−)-N-[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl) pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxy carbonyl) [4-[(trifluoromethyl)thio]phenyl]amino]carbonyl]indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy)phenyl]-1H-1,2,4-triazole-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 93-3798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7).

Fungicides

The active ingredients specified herein by their common name are known and described, for example, in "Pesticide Manual" (16th Ed. British Crop Protection Council) or searchable on the internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) Ergosterol biosynthesis inhibitors, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl] (pyridin-3-yl)methanol, (1.035) (S)-[3-(4-chloro-2-fluorophenyl)-5-(2,4-difluorophenyl)-1,2-oxazol-4-yl]

(pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) mefentrifluconazole, (1.082) ipfentrifluconazole.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5- methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain in complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3 S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tertbutylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), *Bacillus thuringiensis*, especially *B. thuringiensis* subspecies *israelensis* (serotype H-14), strain AM65-52 (Accession No. ATCC1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KV01, *Metarhizium anisopliae*, in particular strain F52 (DSM3884/ATCC90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC20874), *Paecilomyces lilacinus*, in particular *P. lilacinus* strain 251 (AGAL 89/030550), *Talaromyces flavus*, in particular strain V117b,

*Trichoderma atroviride*, in particular strain SC1 (Accession Number CBS 122089), *Trichoderma harzianum*, in particular *T. harzianum rifai* T39 (Accession Number CNCM I-952).

Examples of viruses which are used or can be used as biological pesticides are:

*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., insbesondere *Burkholderia cepacia* (ehemals bekannt als *Pseudomonas cepacia*), *Gigaspora* spp., oder *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., insbesondere *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), pyrethrum/pyrethrins, *Quassia amara*, *Quercus*, *Quillaja*, *Regalia*, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, Viscum album, Brassicaceae extract, especially oilseed rape powder or mustard powder.

Safener as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The inventive treatment of the plants and parts of plants with the compounds of the formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants to phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal compounds, for example imidazolinones, sulfonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, meaning that the compounds of the formula (I) are applied to the foliage, in which case the treatment frequency and the application rate should be adjusted according to the level of infestation with the pest in question.

In the case of systemically active ingredients, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) according to the invention are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention also relates to the use of the compounds of the formula (I) for the treatment of seed for protecting the seed and the resulting plant from animal pests.

The invention further relates to seed which has been treated with a compound of the formula (I) according to the invention for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when a compound of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, rhizobia, mycorrhizae and/or 0 bacteria or fungi, and/or to optimized nitrogen fixation.

The compounds of the formula (I) are suitable for protection of seed of any plant variety which is used in agriculture, in the greenhouse, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical ingredients. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of active agrochemical ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of active agrochemical ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions.

Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of the formula (I) are administered to mammals.

In another specific embodiment, the compounds of the formula (I) are administered to birds, namely caged birds or particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" in the present context means that the compounds of the formula (I) are effective in reducing the incidence of the particular parasite in an animal infected with such parasites to an innocuous degree. More specifically, "controlling" in the present context means that the compounds of the formula (I) kill the respective parasite, inhibit its growth, or inhibit its proliferation.

The arthropods include, for example, but are not limited to, from the order of Anoplurida, for example, *Haematopinus* spp., *Linognathus* spp., *Pediculus* spp., *Phtirus* spp. and *Solenopotes* spp.;

from the order of Mallophagida and the suborders Amblycerina and Ischnocerina, for example, *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp;

from the order of Diptera and the suborders Nematocerina and Brachycerina, for example, *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example, *Ceratophyllus* spp., *Ctenocephalides* spp., *Pulex* spp., *Tunga* spp., *Xenopsylla* spp.;

from the order of heteropterida, for example, *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the subclass of Acari (*Acarina*) and the order of Metastigmata, for example from the family of Argasidae such as *Argas* spp., *Ornithodorus* spp., *Otobius* spp., from the family of Ixodidae such as *Amblyomma* spp., *Dermacentor* spp., *Haemaphysalis* spp., *Hyalomma* spp., *Ixodes* spp., *Rhipicephalus* (*Boophilus*) spp., *Rhipicephalus* spp. (the original genus of multi-host ticks); from the order of Mesostigmata such as *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (*Prostigmata*), for example, *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and *from the order of the Acaridida (Astigmata), for example, Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (Flagellata), such as:

Metamonada: from the order of Diplomonadida, for example, *Giardia* spp., *Spironucleus* spp.

Parabasala: from the order of Trichomonadida, for example, *Histomonas* spp., *Pentatrichomonas* spp., *Tetratrichomonas* spp., *Trichomonas* spp., *Tritrichomonas* spp.

Euglenozoa: from the order of Trypanosomatida, for example, *Leishmania* spp., *Trypanosoma* spp.

Sarcomastigophora (Rhizopoda) such as Entamoebidae, for example, *Entamoeba* spp., *Centramoebidae*, for example *Acanthamoeba* sp., *Euamoebidae*, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, *Acanthocephala*, nematodes, *Pentastoma* and Platyhelminthes (e.g. Monogenea, cestodes and trematodes).

Illustrative helminths include, but are not limited to:

Monogenea: e.g. *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogo-*

*noporus* spp., *Ichthyobothrium* spp., *Ligula* spp., *Schistocephalus* spp., *Spirometra* spp.

From the order of cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

*Acanthocephala*: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

*Pentastoma*: from the order of Porocephalida, for example, Linguatula spp.

In the veterinary field and in animal husbandry, the compounds of the formula (I) are administered by methods generally known in the art, such as via the enteral, parenteral, dermal or nasal route in the form of suitable preparations. Administration may be prophylactic, metaphylactic or therapeutic.

Thus, one embodiment of the present invention relates to the compounds of the formula (I) for use as a medicament.

A further aspect relates to the compounds of the formula (I) for use as an antiendoparasitic agent.

A further specific aspect of the invention relates to the compounds of the formula (I) for use as an antithelminthic agent, especially for use as a nematicide, platyhelminthicide, acanthocephalicide or pentastomicide.

A further specific aspect of the invention relates to the compounds of the formula (I) for use as an antiprotozoic agent.

A further aspect relates to the compounds of the formula (I) for use as an antiectoparasitic agent, especially an arthropodicide, very particularly an insecticide or an acaricide.

Further aspects of the invention are veterinary medicine formulations comprising an effective amount of at least one compound of the formula (I) and at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) with other active ingredients, especially with endo- and ectoparasiticides, are provided for the field of veterinary medicine.

In the field of animal health, "mixture" means not just that two (or more) different active ingredients are formulated in a common formulation and are correspondingly employed together, but also relates to products comprising formulations separated for each active ingredient. Accordingly, when more than two active ingredients are to be employed, all active ingredients can be formulated in a common formulation or all active ingredients can be formulated in separate formulations; likewise conceivable are mixed forms in which some of the active ingredients are formulated together and some of the active ingredients are formulated separately. Separate formulations allow the separate or successive application of the active ingredients in question.

The active ingredients specified here by their "common names" are known and are described, for example, in the "Pesticide Manual" (see above) or can be searched for on the Internet (e.g.: www.alanwood.net/pesticides).

Illustrative active ingredients from the group of the ectoparasiticides as mixing components include, without any intention that this should constitute a restriction, the insecticides and acaricides listed in detail above. Further usable active ingredients are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators; active ingredients having unknown or non-specific mechanisms of action, e.g. fentrifanil, fenoxacrim, cyclopene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz beehive *varroa* acaricides, for example organic acids, e.g. formic acid, oxalic acid.

Illustrative active ingredients from the group of the endoparasiticides, as mixing components, include, but are not limited to, active anthelmintic ingredients and active antiprotozoic ingredients.

The active anthelmintic ingredients include but are not limited to the following active nematicidal, trematicidal and/or cestocidal compounds:

from the class of the macrocyclic lactones, for example: eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;

from the class of the depsipeptides, preferably cyclic depsipeptides, especially 24-membered cyclic depsipeptides, for example: emodepside, PF1022A;

from the class of the tetrahydropyrimidines, for example: morantel, pyrantel, oxantel;

from the class of the imidazothiazoles, for example: butamisole, levamisole, tetramisole;

from the class of the aminophenylamidines, for example: amidantel, deacylated amidantel (dAMD), tribendimidine;

from the class of the aminoacetonitriles, for example: monepantel;

from the class of the paraherquamides, for example: paraherquamide, derquantel;

from the class of the salicylanilides, for example: tribromsalan, bromoxanide, brotianide, clioxanide, closantel, niclosamide, oxyclozanide, rafoxanide;

from the class of the substituted phenols, for example: nitroxynil, bithionol, disophenol, hexachlorophene, niclofolan, meniclopholan;

from the class of the organophosphates, for example: trichlorfon, naphthalofos, dichlorvos/DDVP, crufomate, coumaphos, haloxon;

from the class of the piperazinones/quinolines, for example: praziquantel, epsiprantel;

from the class of the piperazines, for example: piperazine, hydroxyzine;

from the class of the tetracyclines, for example: tetracycline, chlorotetracycline, doxycycline, oxytetracycline, rolitetracycline;

from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Active antiprotozoic ingredients include, but are not limited to, the following active ingredients:

from the class of the triazines, for example: diclazuril, ponazuril, letrazuril, toltrazuril;

from the class of polyether ionophores, for example: monensin, salinomycin, maduramicin, narasin;

from the class of the macrocyclic lactones, for example: milbemycin, erythromycin;

from the class of the quinolones, for example: enrofloxacin, pradofloxacin;

from the class of the quinines, for example: chloroquine;

from the class of the pyrimidines, for example: pyrimethamine;

from the class of the sulfonamides, for example: sulfaquinoxaline, trimethoprim, sulfaclozin;

from the class of the thiamines, for example: amprolium;

from the class of the lincosamides, for example: clindamycin;

from the class of the carbanilides, for example: imidocarb;

from the class of the nitrofurans, for example: nifurtimox;

from the class of the quinazolinone alkaloids, for example: halofuginone;

from various other classes, for example: oxamniquin, paromomycin;

from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) onto a host or after injection into a host (for example malaria parasites by mosquitoes).

Examples of vectors and the diseases or pathogens they transmit are:

1) Mosquitoes
    *Anopheles*: malaria, filariasis;
    *Culex*: Japanese encephalitis, filariasis, other viral diseases, transmission of other worms;
    *Aedes*: yellow fever, dengue fever, further viral disorders, filariasis;
    Simuliidae: transmission of worms, especially *Onchocerca volvulus;*
    Psychodidae: transmission of leishmaniasis
2) Lice: skin infections, epidemic typhus;
3) Fleas: plague, endemic typhus, tapeworms;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia bungdorferi* sensu lato, *Borrelia duttoni*, tick-borne encephalitis, Q fever (*Coxiella burnetii*), babesioses (*Babesia canis canis*), ehrlichiosis.

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, Psychodidae such as *Phlebotomus, Lutzomyia*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) take the form of a ready-to-use pesticide, meaning that they can be applied to the material in question without further modifications. Useful further insecticides or fungicides especially include those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

Synthesis of 7-methyl-3-(pentafluoroethyl)-7H-imidazo[4,5-c]pyridazine

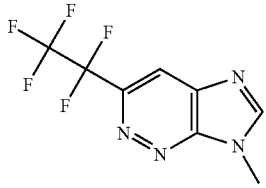 [SMILES: Cn1cnc2cc(C(F)(F)C(F)(F)F)nnc21]

A dry, argon-filled flask equipped with a magnetic stirrer bar and a septum was initially charged with 4-bromo-N-methyl-6-(pentafluoroethyl)pyridazin-3-amine (46 g, 0.15 mol) in anhydrous toluene (1300 ml). 1,1-Diphenylmethanimine (34 g, 0.19 mol), sodium tert-butoxide (20.2 g, 0.21 mol) and [1,1'-bis(diphenylphosphino)ferrocene]dichloropalladium(II), complex with dichloromethane (5.5 g, 7.5 mmol) were then added. After the addition of each reagent, a degassing operation was conducted. The mixture was stirred at 90° C. for 66 h and then at 105° C. for 30 h. Further additions of reagents were conducted, the first comprising 1,1-diphenylmethanimine (9 g, 0.05 mol), sodium tert-butoxide (5 g, 0.053 mol), and [1,1'-bis(diphenylphosphino)ferrocene]dichloropalladium(II), complex with dichloromethane (1.5 g, 2 mmol) and the second comprising 1,1-diphenylmethanimine (5.1 g, 28 mmol), sodium tert-butoxide (3 g, 31 mmol), and [1,1'-bis(diphenylphosphino)ferrocene]dichloro-palladium(II), complex with dichloromethane (0.8 g, 1.1 mmol) after 2 hours at 105° C. After the addition of each reagent, a degassing operation was conducted. The reaction mixture was then stirred at 105° C. for a further 15 h and then concentrated. Water (500 ml) and concentrated hydrochloric acid (500 ml) were then added and the mixture was stirred at reflux for a further 6 hours, and concentrated ethyl acetate (500 ml) and water (300 ml) were added and the phases were separated. The organic phase was extracted with 10% hydrochloric acid (2×50 ml). The aqueous phases were washed with ethyl acetate and neutralized using sodium carbonate in solid form at 0° C. The crude product was extracted with ethyl acetate (3×100 ml) and dried over anhydrous sodium sulfate. After filtration, the solvent was removed under reduced pressure and the residue was extracted by dissolution in triethyl orthoformate (300 ml). The mixture was stirred at 120° C. for 1.5 h and concentrated. The crude product was purified by chromatography, which gave 7-methyl-3-(pentafluoroethyl)-7H-imidazo[4,5-c]pyridazine (10 g, 26%) as a yellow solid.

Synthesis of Methyl 5-fluoro-6-[7-methyl-3-(pentafluoroethyl)-7H-imidazo[4,5-c]pyridazin-6-yl]-pyridine-2-carboxylate

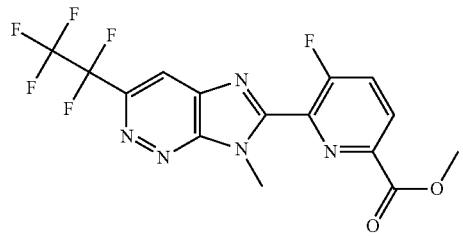 [SMILES: COC(=O)c1ccc(F)c(-c2nc3cc(C(F)(F)C(F)(F)F)nnc3n2C)n1]

To 7-methyl-3-(pentafluoroethyl)-7H-imidazo[4,5-c]pyridazine (500 mg, 1.98 mmol), dissolved in THF (4 ml), was added TMPZnCl.LiCl (1.31 M in THF, 1.67 ml, 2.18 mmol) at 25° C. under argon; this reaction solution was stirred for 10 min. Subsequently, methyl 5-fluoro-6-iodopyridine-2-carboxylate (1.12 g, 3.96 mmol) in THF (4 ml) and tetrakis(triphenylphosphine)palladium(0) (230 mg, 0.19 mmol) were added at 25° C. and stirring of the solution was continued at 80° C. for 3 hours. After standard workup by addition of saturated ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), methyl 5-fluoro-6-[7-methyl-3-(pentafluoroethyl)-7H-imidazo[4,5-c]pyridazin-6-yl]pyridine-2-carboxylate (310 mg, 39%) was obtained in the form of a white solid.

$MH^+$: 406.1; $^1H$ NMR ($d_6$-DMSO): 8.83 (s, 1H), 8.43 (dd, 1H), 8.28 (t, 1H), 4.32 (s, 3H), 3.96 (s, 3H).

Synthesis of 6-(6-bromo-3-fluoropyridin-2-yl)-7-methyl-3-(pentafluoroethyl)-7H-imidazo[4,5-c]-pyridazine

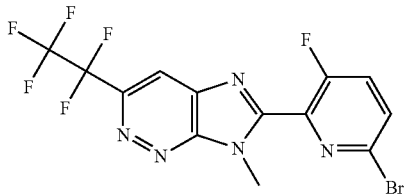 [SMILES: Cn1c(-c2nc(Br)ccc2F)nc2cc(C(F)(F)C(F)(F)F)nnc21]

To 7-methyl-3-(pentafluoroethyl)-7H-imidazo[4,5-c]pyridazine (800 mg, 3.17 mmol), dissolved in THF (4 ml), was added TMPZnCl.LiCl (1.31 M in THF, 2.67 ml, 3.49 mmol) at 25° C. under argon; this reaction solution was stirred for 10 min. Subsequently, 6-bromo-3-fluoro-2-iodopyridine (1.916 g, 6.34 mmol) in THF (4 ml) and tetrakis(triphenylphosphine)palladium(0) (367 mg, 0.31 mmol) were added at 25° C. and stirring of the solution was continued at 80° C. for 4 hours. After standard workup by addition of saturated ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), 6-(6-bromo-3-fluoropyridin-2-yl)-7-methyl-3-(pentafluoroethyl)-7H-imidazo[4,5-c]pyridazin (617 mg, 46%) was obtained in the form of a white solid.

$MH^+$: 427.9; $^1H$ NMR ($d_6$-DMSO): δ 8.81 (s, 1H), 8.11 (m, 2H), 4.25 (s, 3H).

Synthesis of Methyl 5-(ethylsulfanyl)-6-[7-methyl-3-(pentafluoroethyl)-7H-imidazo[4,5-c]-pyridazin-6-yl]pyridine-2-carboxylate

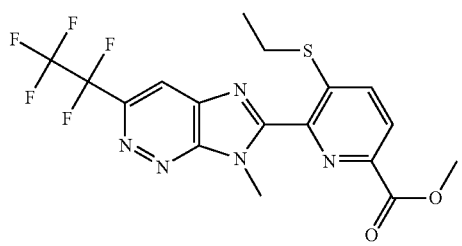 [SMILES: CCSc1ccc(C(=O)OC)nc1-c1nc2cc(C(F)(F)C(F)(F)F)nnc2n1C]

A dry, argon-filled Schlenk flask equipped with a magnetic stirrer bar and a septum was initially charged with methyl 5-fluoro-6-[7-methyl-3-(pentafluoroethyl)-7H-imidazo[4,5-c]pyridazin-6-yl]pyridine-2-carboxylate (150 mg, 0.37 mmol) in anhydrous THF (4 ml). Sodium hydride (15.1 mg, 0.37 mmol) was added at −20° C., and ethanethiol (26 mg, 0.40 mmol) dissolved in 4 ml of THF was added dropwise thereto at −20° C. to max. −10° C. The mixture was stirred at 20° C. for 1.5 h. Saturated aqueous ammonium chloride solution (25 ml) was added to the reaction mixture, which was extracted with ethyl acetate (3×50 ml) and dried over anhydrous sodium sulfate. After filtration, the solvent was removed under reduced pressure. The crude product was purified by chromatography, which gave methyl 5-(ethylsulfanyl)-6-[7-methyl-3-(pentafluoroethyl)-7H-imidazo[4,5-c]pyridazin-6-yl]pyridine-2-carboxylate (104 mg, 63%) in the form of a white solid.

$MH^+$: 448.1; $^1H$ NMR (400 MHz, $d_6$-DMSO) δ ppm: 8.80 (s, 1H), 8.24 (d, 1H), 8.21 (d, 1H), 4.23 (s, 3H), 3.93 (s, 3H), 3.13 (q, 2H), 1.29 (t, 3H).

Synthesis of Methyl 5-(ethylsulfonyl)-6-[7-methyl-3-(pentafluoroethyl)-7H-imidazo[4,5-c]-pyridazin-6-yl]pyridine-2-carboxylate

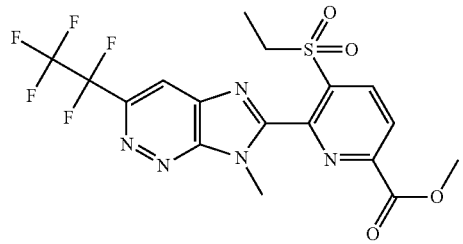 [SMILES: CCS(=O)(=O)c1ccc(C(=O)OC)nc1-c1nc2cc(C(F)(F)C(F)(F)F)nnc2n1C]

A dry, argon-filled Schlenk flask equipped with a magnetic stirrer bar and a septum was initially charged with methyl 5-(ethylsulfanyl)-6-[7-methyl-3-(pentafluoroethyl)-7H-imidazo[4,5-c]pyridazin-6-yl]-pyridine-2-carboxylate (781 mg, 1.74 mmol) in dichloromethane (2 ml). Formic acid (402 mg, 8.72 mmol) and hydrogen peroxide (35%; 1.19 g, 12.2 mmol) were added successively at 20° C. The mixture was stirred at 20° C. for 4 h. A sodium bisulfite, sodium bicarbonate and saturated aqueous ammonium chloride solution were added to the reaction mixture at 0° C., which was extracted with dichloromethane and dried over anhydrous sodium sulfate. After filtration, the solvent was removed under reduced pressure. The crude product was purified by chromatography, which gave methyl 5-(ethylsulfonyl)-6-[7-methyl-3-(pentafluoroethyl)-7H-imidazo[4,5-c]pyridazin-6-yl]pyridine-2-carboxylate (603 mg, 73%) in the form of a white solid.

$MH^+$: 480.1; $^1H$ NMR (400 MHz, $d_6$-DMSO) δ ppm: 8.85 (s, 1H), 8.79 (d, 1H), 8.58 (d, 1H), 3.98 (s, 3H), 3.97 (s, 3H), 3.78 (q, 2H), 1.21 (t, 3H).

Synthesis of N-ethyl-5-(ethylsulfonyl)-6-[7-methyl-3-(pentafluoroethyl)-7H-imidazo[4,5-c]-pyridazin-6-yl]pyridine-2-carboxamide

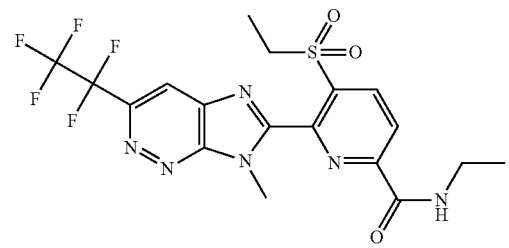 [SMILES: CCNC(=O)c1ccc(S(=O)(=O)CC)c(-c2nc3cc(C(F)(F)C(F)(F)F)nnc3n2C)n1]

A dry, argon-filled Schlenk flask equipped with a magnetic stirrer bar and a septum was initially charged with methyl 5-(ethylsulfonyl)-6-[7-methyl-3-(pentafluoroethyl)-7H-imidazo[4,5-c]pyridazin-6-yl]-pyridine-2-carboxylate (100 mg, 0.20 mmol) in methanol (2 ml). Ethylamine (94.1 mg, 2.08 mmol) was added at 20° C. and the mixture was stirred at 20° C. for 1 h. Saturated aqueous ammonium chloride solution (25 ml) was added to the reaction mixture, which was extracted with ethyl acetate (3×50 ml) and dried over anhydrous sodium sulfate. After filtration, the solvent was removed under reduced pressure. The crude product was purified by chromatography, which gave N-ethyl-5-(ethylsulfonyl)-6-[7-methyl-3-(pentafluoroethyl)-7H-imidazo[4,5-c]pyridazin-6-yl]pyridine-2-carboxamide (65 mg, 63%) in the form of a white solid.

MH⁺: 493.1; ¹H NMR (400 MHz, d₆-DMSO) δ ppm: 9.04 (t, 1H), 8.87 (s, 1H), 8.75 (d, 1H), 8.53 (d, 1H), 4.01 (s, 3H), 3.79 (q, 2H), 3.34 (q, 2H), 1.21 (t, 3H), 1.12 (t, 3H).

Synthesis of 1-{5-(ethylsulfonyl)-6-[7-methyl-3-(pentafluoroethyl)-7H-imidazo[4,5-c]pyridazin-6-yl]pyridin-2-yl}-3-methylurea

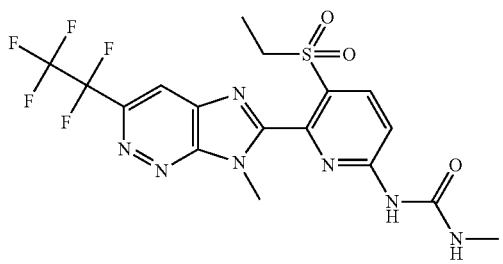 [SMILES: CCS(=O)(=O)c1ccc(NC(=O)NC)nc1-c1nc2cc(C(F)(F)C(F)(F)F)nnc2n1C]

A dry, argon-filled Schlenk flask equipped with a magnetic stirrer bar and a septum was initially charged with 6-[6-bromo-3-(ethylsulfonyl)pyridin-2-yl]-7-methyl-3-(pentafluoroethyl)-7H-imidazo[4,5-c]-pyridazine (100 mg, 0.20 mmol) in anhydrous dioxane (2 ml). Methylurea (18 mg, 0.24 mmol), caesium carbonate (98 mg, 0.30 mmol), 9,9-dimethyl-4,5-bis(diphenylphosphino)xanthene (12 mg, 0.02 mmol) and bis(dibenzylideneacetone)palladium(0) (6 mg, 0.02 mmol) were then added, and the mixture was stirred at 80° C. for 1 h. Saturated aqueous sodium chloride solution (25 ml) was added to the reaction mixture, which was extracted with ethyl acetate (3×50 ml) and dried over anhydrous sodium sulfate. After filtration, the solvent was removed under reduced pressure. The crude product was purified by chromatography, which gave 1-{5-(ethylsulfonyl)-6-[7-methyl-3-(pentafluoroethyl)-7H-imidazo[4,5-c]pyridazin-6-yl]pyridin-2-yl}-3-methylurea (82 mg, 83%) in the form of a white solid.

MH⁺: 494.0; ¹H NMR (400 MHz, d₆-DMSO) δ ppm: 10.13 (s, 1H), 8.81 (s, 1H), 8.37 (d, 1H), 8.07 (d, 1H), 7.13 (bs, 1H), 3.94 (s, 3H), 3.59 (q, 2H), 2.71 (d, 3H), 1.18 (t, 3H).

The compounds were separated according to EEC Directive 79/831 Annex V.A8 by HPLC (high-performance liquid chromatography) on a reversed-phase column (C 18). Temperature: 55° C.

The LC-MS determination of the M⁺ in the acidic range was effected at pH 2.7 with 0.1% aqueous formic acid and acetonitrile (containing 0.1% formic acid) as eluents; linear gradient from 10% acetonitrile to 95% acetonitrile, instrument: Agilent 1100 LC system, Agilent MSD system, HTS PAL.

The LC-MS determination of the M⁺ in the neutral range was effected at pH 7.8 with 0.001 molar aqueous ammonium hydrogencarbonate solution and acetonitrile as eluents; linear gradient from 10% acetonitrile to 95% acetonitrile.

The NMR data of selected examples are listed either in conventional form (δ values, multiplet splitting, number of hydrogen atoms) or as NMR peak lists.

In each case, the solvent in which the NMR spectrum was recorded is stated.

In analogy to the examples and by the preparation processes described above, it is possible to obtain the compounds of the formula (I) shown in Table 1:

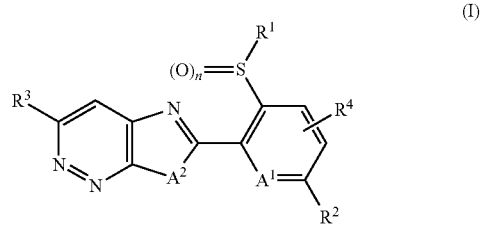

TABLE 1

| Ex. No. | Structure |
|---------|-----------|
| I-01 | 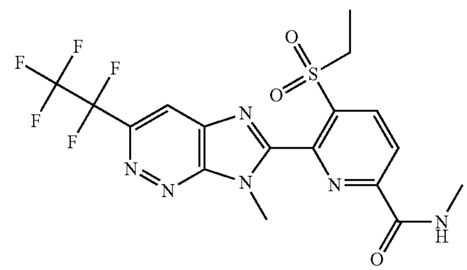 [SMILES: CCS(=O)(=O)c1ccc(C(=O)NC)nc1-c1nc2cc(C(F)(F)C(F)(F)F)nnc2n1C] |
| I-02 | 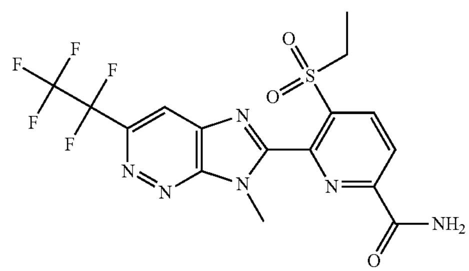 [SMILES: CCS(=O)(=O)c1ccc(C(N)=O)nc1-c1nc2cc(C(F)(F)C(F)(F)F)nnc2n1C] |
| I-03 | 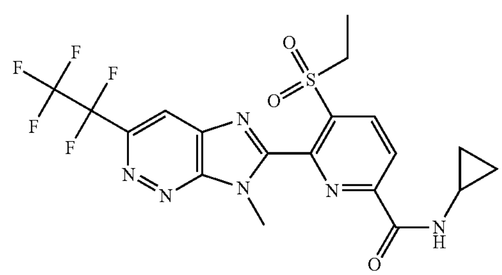 [SMILES: CCS(=O)(=O)c1ccc(C(=O)NC2CC2)nc1-c1nc2cc(C(F)(F)C(F)(F)F)nnc2n1C] |
| I-04 | 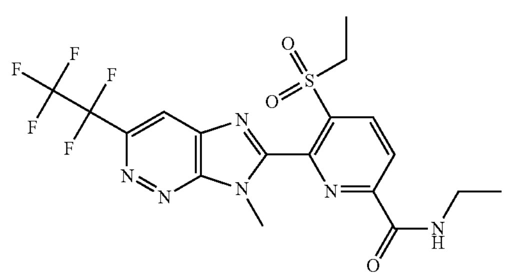 [SMILES: CCNC(=O)c1ccc(S(=O)(=O)CC)c(-c2nc3cc(C(F)(F)C(F)(F)F)nnc3n2C)n1] |

TABLE 1-continued
| Ex. No. | Structure |
|---|---|
| I-05 | 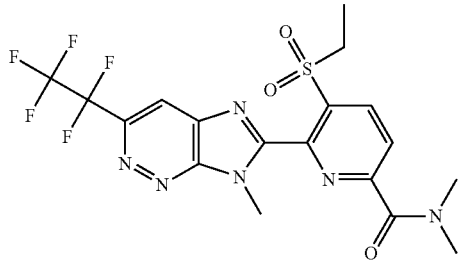 [SMILES: CCS(=O)(=O)c1ccc(C(=O)N(C)C)nc1-c1nc2cc(C(F)(F)C(F)(F)F)nnc2n1C] |
| I-06 | 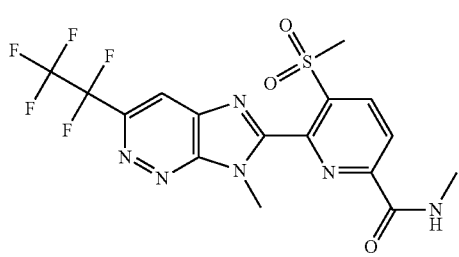 [SMILES: CNC(=O)c1ccc(S(C)(=O)=O)c(-c2nc3cc(C(F)(F)C(F)(F)F)nnc3n2C)n1] |
| I-07 | 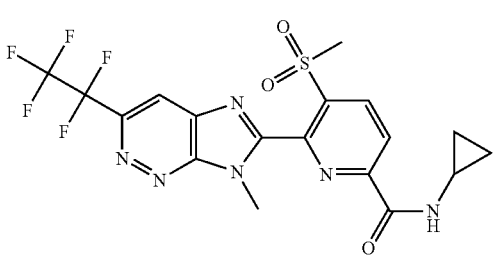 [SMILES: Cn1c(-c2nc(C(=O)NC3CC3)ccc2S(C)(=O)=O)nc2cc(C(F)(F)C(F)(F)F)nnc21] |
| I-08 | 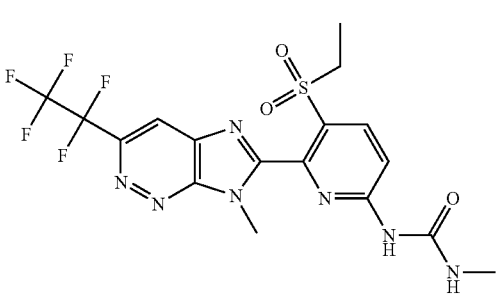 [SMILES: CCS(=O)(=O)c1ccc(NC(=O)NC)nc1-c1nc2cc(C(F)(F)C(F)(F)F)nnc2n1C] |
| I-09 | 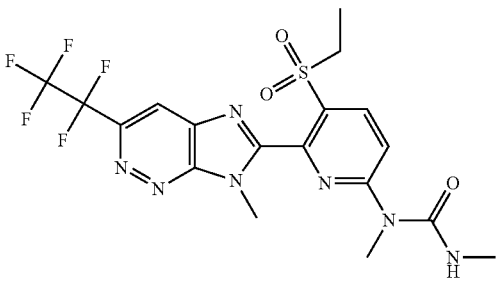 [SMILES: CCS(=O)(=O)c1ccc(N(C)C(=O)NC)nc1-c1nc2cc(C(F)(F)C(F)(F)F)nnc2n1C] |
| Ex. No. | Structure |
|---|---|
| I-10 | 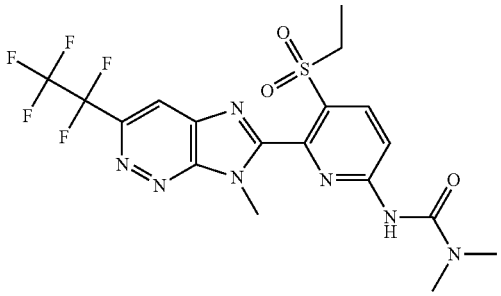 [SMILES: CCS(=O)(=O)c1ccc(NC(=O)N(C)C)nc1-c1nc2cc(C(F)(F)C(F)(F)F)nnc2n1C] |
| I-11 | 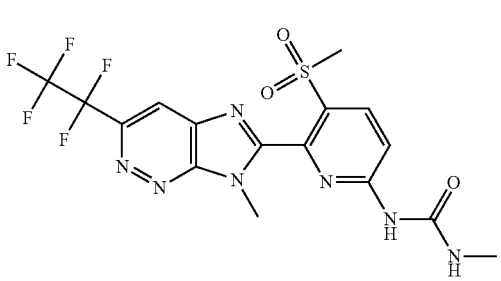 [SMILES: CNC(=O)Nc1ccc(S(C)(=O)=O)c(-c2nc3cc(C(F)(F)C(F)(F)F)nnc3n2C)n1] |
| I-12 | 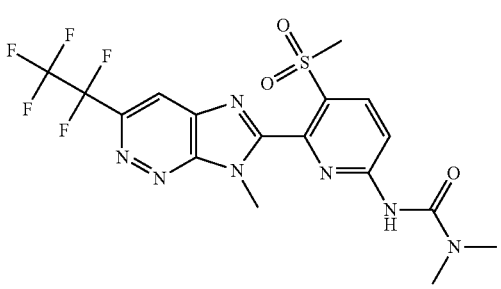 [SMILES: CN(C)C(=O)Nc1ccc(S(C)(=O)=O)c(-c2nc3cc(C(F)(F)C(F)(F)F)nnc3n2C)n1] |
| I-13 | 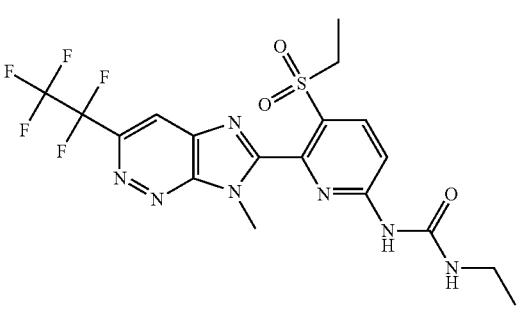 [SMILES: CCNC(=O)Nc1ccc(S(=O)(=O)CC)c(-c2nc3cc(C(F)(F)C(F)(F)F)nnc3n2C)n1] |
| I-14 | 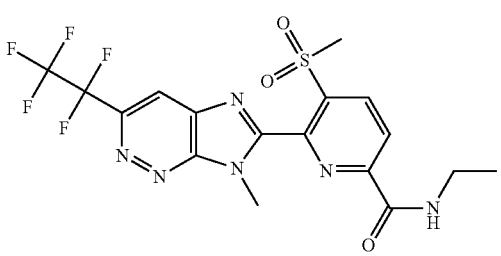 [SMILES: CCNC(=O)c1ccc(S(C)(=O)=O)c(-c2nc3cc(C(F)(F)C(F)(F)F)nnc3n2C)n1] |

TABLE 1-continued

| Ex. No. | Structure |
|---|---|
| I-15 | 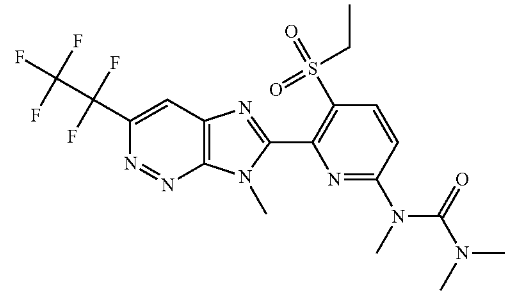 [SMILES: CCS(=O)(=O)c1ccc(N(C)C(=O)N(C)C)nc1-c1nc2cc(C(F)(F)C(F)(F)F)nnc2n1C] |

NMR Data of Selected Examples

NMR Peak List Method

The 1H-NMR data of selected examples are noted in the form of 1H-NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore takes the form of:

$\delta_1$ (intensity$_1$); $\delta_2$ (intensity$_2$); ... ; $\delta_i$ (intensity$_i$); ... ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in $d_6$-DMSO and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

TABLE 2

NMR data of selected compounds

| Ex. | |
|---|---|
| I-01 | I-01: $^1$H NMR(400.0 MHz, $d_6$-DMSO):<br>δ = 8.9984(1.2); 8.9865(1.2); 8.8717(6.1); 8.7711(3.0); 8.7504(3.6); 8.5433(3.6); 8.5226(3.0); 5.7545 (2.0); 4.0383(1.0); 4.0226(16.0); 4.0029(0.4); 3.8261(1.0); 3.8076(3.5); 3.7891(3.5); 3.7709(1.1); 3.3212 (73.6); 2.8484(7.4); 2.8363(7.3); 2.6713(0.6); 2.5064(76.1); 2.5022(94.6); 2.4980(70.2); 2.3289(0.6); 1.9888(3.0); 1.2593(0.3); 1.2413(3.9); 1.2228(8.2); 1.2043(3.7); 1.1932(0.9); 1.1753(1.6); 1.1575(0.8); −0.0002(3.7) |
| I-02 | I-02: $^1$H NMR(400.0 MHz, $d_6$-DMSO):<br>δ = 8.8631(6.5); 8.7664(3.1); 8.7457(3.8); 8.5461(3.8); 8.5254(3.2); 8.3901(1.6); 8.3146(0.5); 8.0405 (1.6); 5.7549(2.1); 4.0312(16.0); 3.8457(1.0); 3.8272(3.4); 3.8087(3.4); 3.7903(1.2); 3.3670(0.6); 3.3203 (78.4); 2.6710(1.3); 2.6660(1.0); 2.5061(175.0); 2.5017(226.3); 2.4973(162.7); 2.3331(1.0); 2.3283 (1.3); 2.3239(1.0); 1.2471(3.7); 1.2286(8.3); 1.2101(3.6); 0.0078(1.6); −0.0002(44.1); −0.0083(1.7) |
| I-03 | I-03: $^1$H NMR(400.0 MHz, $d_6$-DMSO):<br>δ = 8.9280(1.6); 8.9163(1.6); 8.8603(7.4); 8.8500(0.4); 8.7614(3.1); 8.7406(3.8); 8.5367(3.7); 8.5159 (3.2); 5.7546(7.8); 4.5160(0.7); 4.0162(0.8); 3.9885(16.0); 3.8084(1.1); 3.7900(3.6); 3.7714(3.6); 3.7530 (1.1); 3.3203(47.9); 2.9552(0.5); 2.9461(0.6); 2.9362(1.0); 2.9257(1.0); 2.9193(0.7); 2.9076(0.5); 2.6751 (0.4); 2.6712(0.5); 2.5065(60.7); 2.5022(78.3); 2.4979(58.5); 2.3288(0.5); 1.9888(0.7); 1.2889(0.4); 1.2310(4.4); 1.2124(8.4); 1.1939(3.9); 1.1754(0.5); 0.7483(0.5); 0.7294(2.4); 0.7155(1.7); 0.7103(2.1); 0.7008(1.1); 0.6936(0.5); 0.6832(0.4); 0.6692(1.3); 0.6594(3.0); 0.6495(2.4); 0.6305(0.5); −0.0002(1.6) |
| I-04 | I-04: $^1$H NMR(400.0 MHz, $d_6$-DMSO):<br>δ = 9.0616(0.6); 9.0470(1.3); 9.0320(0.6); 8.8707(6.7); 8.7689(3.0); 8.7482(3.7); 8.5462(3.6); 8.5255 (3.1); 4.0562(0.4); 4.0384(1.3); 4.0195(16.0); 4.0028(0.6); 3.8182(1.0); 3.7998(3.3); 3.7813(3.4); 3.7628 (1.0); 3.3771(0.5); 3.3596(1.9); 3.3425(2.8); 3.3236(46.0); 3.3089(1.0); 2.6713(0.4); 2.5067(52.0); 2.5022(68.3); 2.4978(50.9); 2.3287(0.4); 1.9889(5.3); 1.3977(0.3); 1.2379(3.7); 1.2195(7.8); 1.2009(3.5); 1.1933(1.6); 1.1755(2.7); 1.1577(1.4); 1.1353(3.8); 1.1174(8.2); 1.0995(3.7); −0.0002(1.0) |
| I-05 | I-05: $^1$H NMR(400.0 MHz, $d_6$-DMSO):<br>δ = 8.8324(6.6); 8.7100(3.1); 8.6893(3.4); 8.1695(3.4); 8.1488(3.2); 4.0566(0.4); 4.0387(1.1); 4.0209 (1.2); 3.9924(15.3); 3.7969(1.1); 3.7783(3.5); 3.7598(3.5); 3.7412(1.1); 3.3212(26.2); 3.0442(15.0); 2.9989(16.0); 2.6718(0.5); 2.5067(62.3); 2.5026(76.2); 2.4985(55.4); 2.3331(0.4); 2.3290(0.5); 1.9892 (4.6); 1.2590(0.3); 1.2475(3.8); 1.2290(8.0); 1.2105(3.6); 1.1934(1.3); 1.1756(2.4); 1.1578(1.2) |
| I-06 | I-06: $^1$H NMR(400.0 MHz, $d_6$-DMSO):<br>δ = 8.9997(1.0); 8.9878(1.0); 8.8816(6.3); 8.8072(3.2); 8.7865(3.8); 8.5518(3.8); 8.5311(3.3); 7.6269 (0.4); 7.6149(0.3); 7.5973(0.4); 4.0319(16.0); 4.0202(0.6); 3.6495(14.4); 3.3203(19.8); 2.8502(7.1); |

TABLE 2-continued

NMR data of selected compounds

| Ex. | |
|---|---|
| | 2.8381(7.1); 2.6749(0.4); 2.6706(0.5); 2.6663(0.4); 2.5239(1.1); 2.5104(30.3); 2.5060(63.0); 2.5016(83.9); 2.4971(59.7); 2.4927(28.2); 2.3325(0.3); 2.3283(0.5); 2.3239(0.3); 1.9888(1.5); 1.1924(0.4); 1.1746 (0.8); 1.1568(0.4); 0.0080(0.6); −0.0002(21.9); −0.0085(0.8) |
| I-07 | I-07: $^1$H NMR(400.0 MHz, $d_6$-DMSO): <br> δ = 8.9291(1.4); 8.9175(1.4); 8.8693(7.1); 8.7974(3.2); 8.7766(3.8); 8.5440(3.8); 8.5231(3.3); 7.6276 (0.3); 4.0556(0.5); 4.0378(1.6); 4.0199(1.7); 3.9966(16.0); 3.6339(14.7); 3.3208(47.9); 2.9596(0.4); 2.9512(0.6); 2.9405(0.9); 2.9304(0.9); 2.9244(0.6); 2.9122(0.4); 2.6751(0.5); 2.6706(0.6); 2.6659(0.5); 2.5235(1.8); 2.5099(44.3); 2.5059(88.6); 2.5014(115.7); 2.4970(82.6); 2.4929(39.4); 2.3325(0.5); 2.3282 (0.6); 2.3237(0.5); 1.9888(6.9); 1.3974(0.4); 1.1923(1.8); 1.1745(3.5); 1.1567(1.7); 0.9612(0.4); 0.7495 (0.5); 0.7305(2.3); 0.7167(1.6); 0.7110(2.0); 0.7019(1.1); 0.6965(0.6); 0.6849(0.4); 0.6736(1.1); 0.6635 (2.9); 0.6539(2.1); 0.6345(0.5); −0.0002(16.8); −0.0083(0.7) |
| I-08 | I-08: $^1$H NMR(400.0 MHz, $d_6$-DMSO): <br> δ = 10.1290(2.7); 8.8120(6.9); 8.3799(2.9); 8.3572(3.4); 8.0855(2.2); 8.0628(1.9); 7.1345(1.0); 7.1228 (1.0); 3.9414(16.0); 3.9078(0.5); 3.6262(1.0); 3.6081(3.5); 3.5895(3.5); 3.5712(1.0); 3.3227(167.9); 2.7101 (6.9); 2.6987(7.0); 2.6711(1.3); 2.5062(166.4); 2.5020(213.5); 2.4980(155.3); 2.3285(1.2); 1.1952 (3.7); 1.1767(8.1); 1.1582(3.6); 1.1468(0.4); 0.1459(0.4); 0.0077(3.3); −0.0002(87.8); −0.1491(0.4) |
| I-09 | I-09: $^1$H NMR(400.0 MHz, $d_6$-DMSO): <br> δ = 8.8090(7.0); 8.3548(3.2); 8.3319(3.8); 8.0521(3.3); 8.0292(3.0); 7.9842(1.2); 7.9734(1.2); 3.9779 (16.0); 3.7002(0.9); 3.6817(3.3); 3.6633(3.4); 3.6448(1.0); 3.3965(15.6); 3.3226(38.6); 2.7423(7.4); 2.7313 (7.4); 2.6755(0.4); 2.6714(0.5); 2.6669(0.4); 2.5244(1.3); 2.5108(32.7); 2.5067(67.0); 2.5022(88.6); 2.4978(63.6); 2.4935(30.4); 2.3336(0.4); 2.3288(0.5); 2.3244(0.4); 1.6480(0.4); 1.2195(3.5); 1.2011 (7.9); 1.1826(3.4); −0.0002(8.6); −0.0082(0.3) |
| I-10 | I-10: $^1$H NMR(601.6 MHz, $d_6$-DMSO): <br> δ = 9.9316(2.2); 8.8172(6.7); 8.3878(2.8); 8.3727(3.4); 8.2283(3.6); 8.2131(3.2); 5.7520(7.5); 3.9610 (16.0); 3.5877(1.0); 3.5754(3.3); 3.5631(3.4); 3.5508(1.0); 3.3051(61.1); 2.9784(15.4); 2.6150(0.4); 2.6120 (0.6); 2.6090(0.4); 2.5212(1.0); 2.5182(1.3); 2.5151(1.3); 2.5062(33.1); 2.5032(69.9); 2.5002(96.9); 2.4972(72.0); 2.4943(35.3); 2.3874(0.4); 2.3844(0.6); 2.3814(0.4); 1.9876(0.3); 1.1868(3.6); 1.1745 (8.1); 1.1622(3.6); 0.0052(1.1); −0.0002(35.2); −0.0057(1.3) |
| I-11 | I-11: $^1$H NMR(400.0 MHz, $d_6$-DMSO): <br> δ = 10.1134(2.6); 8.8188(6.3); 8.7722(0.6); 8.4169(2.8); 8.3942(3.3); 8.0794(2.2); 8.0566(2.0); 7.1434 (1.0); 7.1313(1.0); 5.7570(1.9); 4.3578(0.6); 3.9500(16.0); 3.9171(1.0); 3.8516(0.7); 3.4749(14.3); 3.3494 (0.8); 3.3426(0.9); 3.3200(45.0); 3.0091(0.6); 2.7405(0.3); 2.7325(0.4); 2.7114(6.8); 2.7000(6.9); 2.6702(0.9); 2.6660(0.7); 2.5057(113.2); 2.5013(151.0); 2.4970(111.8); 2.3321(0.6); 2.3281(0.8); 0.1458(0.5); 0.0077(4.2); −0.0003(115.2); −0.0083(5.4); −0.1502(0.5) |
| I-12 | I-12: $^1$H NMR(400.0 MHz, $d_6$-DMSO): <br> δ = 9.9295(2.3); 8.8307(4.4); 8.4298(2.0); 8.4070(2.4); 8.2301(2.8); 8.2073(2.4); 7.6454(0.3); 7.6272 (0.6); 7.6154(0.4); 7.5978(0.5); 7.5743(0.4); 7.5661(0.4); 7.5483(0.4); 3.9731(12.0); 3.4592(10.5); 3.3219 (20.6); 2.9804(16.0); 2.5241(0.6); 2.5104(18.0); 2.5062(36.9); 2.5018(48.8); 2.4973(34.9); 2.4932(16.8); 2.0749(1.0); 0.0078(1.3); −0.0002(37.4); −0.0084(1.4) |
| I-13 | I-13: $^1$H NMR(400.0 MHz, $d_6$-DMSO): <br> δ = 10.0107(3.0); 8.8175(6.1); 8.3838(2.7); 8.3612(3.4); 8.1622(2.7); 8.1394(2.2); 7.1459(0.7); 7.1319 (1.2); 7.1184(0.7); 3.9485(16.0); 3.8478(0.5); 3.6316(1.0); 3.6322(3.4); 3.5948(3.4); 3.5766(1.1); 3.3228 (72.7); 3.2049(0.6); 3.1872(1.9); 3.1716(2.2); 3.1549(1.9); 3.1369(0.6); 2.6753(0.5); 2.6710(0.6); 2.5065(87.4); 2.5022(113.4); 2.4980(81.7); 2.3334(0.5); 2.3286(0.6); 1.1965(3.7); 1.1780(8.1); 1.1596 (3.6); 1.0905(0.3); 1.0737(4.3); 1.0558(8.9); 1.0379(4.1); 0.1462(0.4); 0.0078(3.3); −0.0002(87.3); −0.1495(0.4) |
| I-14 | I-14: $^1$H NMR(400.0 MHz, $d_6$-DMSO): <br> δ = 9.0611(0.7); 9.0459(1.3); 9.0314(0.7); 8.8799(6.2); 8.8058(3.2); 8.7850(3.8); 8.5535(3.8); 8.5327 (3.3); 5.7572(1.0); 4.0288(16.0); 3.6425(14.5); 3.3781(0.5); 3.3606(1.8); 3.3436(2.4); 3.3199(17.5); 2.6751(0.4); 2.6706(0.6); 2.5060(79.4); 2.5016(105.2); 2.4972(77.5); 2.3329(0.4); 2.3284(0.6); 2.3241 (0.5); 1.1379(3.9); 1.1200(8.4); 1.1020(3.8); 0.0077(0.4); −0.0001(11.0) |
| I-15 | I-15: $^1$H NMR(400.0 MHz, $d_6$-DMSO): <br> δ = 8.7951(3.2); 8.2607(1.6); 8.2379(1.8); 8.2126(0.4); 7.2709(1.7); 7.2481(1.7); 3.9907(8.4); 3.6810(0.5); 3.6626(1.8); 3.6440(1.8); 3.6256(0.5); 3.3254(11.0); 3.2183(8.2); 2.9474(16.0); 2.6713(0.4); 2.5245(0.9); 2.5108(23.2); 2.5066(47.0); 2.5022(61.7); 2.4977(44.5); 2.4936 (21.9); 2.3288(0.4); 1.2156(1.9); 1.1972(4.2); 1.1787(1.8); 0.0077(2.3); −0.0002(63.2); −0.0082(2.6) |

USE EXAMPLES

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 µl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm$^2$, given homogeneous distribution, an area-based dose of 5 µg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm$^2$. 100% efficacy means that all the fleas were dead or moribund. 0% efficacy means that no fleas were harmed.

In this test, for example, the following compounds from the preparation examples show an efficacy of 100% at an application rate of 5 µg/cm² (=500 g/ha): I-09, I-10, I-11, I-12, I-13

*Ctenocephalides felis*—Oral Test

Solvent: dimethyl sulfoxide

To produce a suitable active ingredient formulation, 10 mg of active ingredient are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient formulation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-08, I-09, I-10, I-11, I-12, I-13

*Lucilia cuprina* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active ingredient formulation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: I-01, I-02, I-03, I-04, I-05, I-08, I-09, II-10, I-11, I-12, II-13

In this test, for example, the following compound from the preparation examples shows an efficacy of 95% at an application rate of 100 ppm: I-06

In this test, for example, the following compound from the preparation examples shows an efficacy of 90% at an application rate of 100 ppm: I-14

*Musca domestica* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the kill in % is determined. 100% means that all of the flies have been killed; 0% means that none of the flies have been killed.

In this test, for example, the following compound from the preparation examples shows an efficacy of 100% at an application rate of 100 ppm: I-01

In this test, for example, the following compound from the preparation examples shows an efficacy of 90% at an application rate of 100 ppm: I-10

In this test, for example, the following compounds from the preparation examples show an efficacy of 80% at an application rate of 100 ppm: I-04, I-13

*Meloidogyne incognita* Test

| Solvent: | 125.0 parts by weight of acetone |
|---|---|

To produce a suitable active ingredient formulation, 1 part by weight of active ingredient is mixed with the stated amount of solvent and the concentrate is diluted to the desired concentration with water.

Vessels are filled with sand, active ingredient solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples show an efficacy of 100% at an application rate of 20 ppm: I-08, I-09, I-10, I-12, I-13

In this test, for example, the following compounds from the preparation examples show an efficacy of 90% at an application rate of 20 ppm: I-01, I-02, I-15

*Myzus persicae*—Oral Test

| Solvent: | 100 parts by weight of acetone |
|---|---|

To produce a suitable active ingredient formulation, 1 part by weight of active ingredient is dissolved with the stated parts by weight of solvent and made up to the desired concentration with water.

50 µl of the active ingredient preparation are transferred into microtitre plates and made up to a final volume of 200 µl with 150 µl of IPL41 insect medium (33%+15% sugar). Subsequently, the plates are sealed with parafilm, which a mixed population of green peach aphids (*Myzus persicae*) within a second microtitre plate is able to puncture and imbibe the solution.

After 5 days, the efficacy in % is determined. 100% means that all the aphids have been killed; 0% means that no aphids have been killed.

In this test, for example, the following compounds from the preparation examples show an efficacy of 100% at an application rate of 0.8 ppm: I-01, I-02, I-03, I-04, I-05, I-06, I-10, I-11, I-12, I-13, I-15, In this test, for example, the following compounds from the preparation examples show an efficacy of 90% at an application rate of 0.8 ppm: I-07, I-08, I-09, I-14

*Myzus persicae*—Spray Test

| Solvent: | 78 parts by weight of acetone |
|---|---|
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 5 days, the efficacy in % is determined. 100% means that all the aphids have been killed; 0% means that no aphids have been killed.

In this test, for example, the following compounds from the preparation examples show an efficacy of 100% at an application rate of 100 g/ha: I-02, I-03, I-04, I-15

In this test, for example, the following compounds from the preparation examples show an efficacy of 90% at an application rate of 100 g/ha: I-01, I-05, I-06, I-08, I-12

In this test, for example, the following compounds from the preparation examples show an efficacy of 100% at an application rate of 20 g/ha: I-08, I-09, I-10

In this test, for example, the following compounds from the preparation examples show an efficacy of 90% at an application rate of 20 g/ha: I-03, I-05, I-12, I-13, I-15

*Phaedon cochleariae*—Spray Test

| Solvent: | 78.0 parts by weight of acetone |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 100 g/ha: I-01, I-02, I-03, I-04, I-05, I-07, I-08. I-09, I-10, I-11, I-12, I-13, I-14, II-15

*Spodoptera frugiperda*—Spray Test

| Solvent: | 78.0 parts by weight of acetone |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 6 days, the efficacy in % is determined. 100% means that all the caterpillars have been killed; 0% means that no caterpillar has been killed.

In this test, for example, the following compound from the preparation examples shows an efficacy of 83% at an application rate of 100 g/ha: I-13

*Tetranychus urticae*—Spray Test, OP-Resistant

| Solvent: | 78.0 parts by weight of acetone |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active ingredient formulation of the desired concentration.

After 6 days, the efficacy in % is determined. 100% means that all the spider mites have been killed; 0% means that no spider mites have been killed.

In this test, for example, the following compound from the preparation examples shows an efficacy of 90% at an application rate of 4 g/ha: I-08

CONTRASTIVE EXAMPLES

*Phaedon cochleariae*—Spray Test (PHAECO)

| Solvent: | 78.0 parts by weight of acetone |
| | 1.5 parts by weight of dimethylformamide |
| Emulsifier: | alkylaryl polyglycol ether |

To produce an appropriate active ingredient formulation, 1 part by weight of active ingredient is dissolved with the stated parts by weight of solvent and made up with water containing an emulsifier concentration of 1000 ppm until the desired concentration is attained. For production of further test concentrations, the mixture is diluted with emulsifier-containing water.

Discs of chinese cabbage leaves (*Brassica pekinensis*) are sprayed with an active ingredient formulation of the desired concentration and, after drying, populated with larvae of the mustard beetle (*Phaedon cochleariae*).

After the desired time, the efficacy in % is determined. 100% means that all beetle larvae have been killed; 0% means that no beetle larvae have been killed.

In this test, for example, the following compounds from the preparation examples show superior efficacy compared to the prior art: see table.

*Myzus persicae*—Spray Test (MYZUPE)

| Solvent: | 78.0 parts by weight of acetone |
| | 1.5 parts by weight of dimethylformamide |
| Emulsifier: | alkylaryl polyglycol ether |

To produce an appropriate active ingredient formulation, 1 part by weight of active ingredient is dissolved with the stated parts by weight of solvent and made up with water containing an emulsifier concentration of 1000 ppm until the desired concentration is attained. For production of further test concentrations, the mixture is diluted with emulsifier-containing water.

Discs of chinese cabbage leaves (*Brassica pekinensis*) infested by all stages of the green peach aphid (*Myzus persicae*) are sprayed with an active ingredient formulation of the desired concentration.

After the desired time, the efficacy in % is determined. 100% means that all aphids have been killed; 0% means that no aphids have been killed.

In this test, for example, the following compounds from the preparation examples show superior efficacy compared to the prior art: see table.

*Meloidogyne incognita* Test (MELGIN)

| Solvent: | 125.0 parts by weight of acetone |
|---|---|

To produce an appropriate active ingredient formulation, 1 part by weight of active ingredient is mixed with the specified amount of solvent and the concentrate is diluted to the desired concentration with water.

Vessels are filled with sand, active ingredient solution, an egg/larvae suspension of the southern root-knot nematode (*Meloidogyne incognita*) and lettuce seeds. The lettuce seeds germinate and the plants develop. The root-knots develop on the roots.

After the desired time, the nematicidal effect is determined from the formation of root-knots in %. 100% means that no root-knots were found; 0% means that the number of root-knots on the treated plants corresponds to that on the untreated control.

In this test, for example, the following compounds from the preparation examples show superior efficacy compared to the prior art: see table.

*Aphis Gossypii*—Spray Test (APHIGO)

| Solvent: | 14 parts by weight of dimethylformamide |
|---|---|
| Emulsifier: | alkylaryl polyglycol ether |

To produce an appropriate active ingredient formulation, 1 part by weight of active ingredient is dissolved with the specified parts by weight of solvent and made up with water containing an emulsifier concentration of 1000 ppm until the desired concentration is attained. To produce further test concentrations, the mixture is diluted with emulsifier-containing water. If addition of ammonium salts or/and penetrants is required, these are each added to the preparation solution in a concentration of 1000 ppm.

Cotton plants (*Gossypium hirsutum*) severely infested by the cotton aphid (*Aphis gossypii*) are sprayed with an active ingredient formulation of the desired concentration.

After the desired time, the kill in % is determined. 100% means that all aphids have been killed; 0% means that no aphids have been killed.

In this test, for example, the following compounds from the preparation examples show superior efficacy compared to the prior art: see table.

*Myzus persicae*—Spray Test (MYZUPE S)

| Solvent: | 14 parts by weight of dimethylformamide |
|---|---|
| Emulsifier: | alkylaryl polyglycol ether |

To produce an appropriate active ingredient formulation, 1 part by weight of active ingredient is dissolved with the specified parts by weight of solvent and made up with water containing an emulsifier concentration of 1000 ppm until the desired concentration is attained. To produce further test concentrations, the mixture is diluted with emulsifier-containing water. If addition of ammonium salts or/and penetrants is required, these are each added to the preparation solution in a concentration of 1000 ppm.

Bell pepper plants (*Capsicum annuum*) severely infested by the green peach aphid (*Myzus persicae*) are treated by spraying with the active ingredient formulation in the desired concentration.

After the desired time, the kill in % is determined. 100% means that all the animals have been killed; 0% means that no animals have been killed.

In this test, for example, the following compounds from the preparation examples show superior efficacy compared to the prior art: see table.

*Myzus persicae*—Drench Test (MYZUPE D)

| Solvent: | 7 parts by weight of dimethylformamide |
|---|---|
| Emulsifier: | 2 parts by weight of alkylaryl polyglycol ether |

To produce an appropriate active ingredient formulation, 1 part by weight of active ingredient is mixed with the specified amounts of solvent and emulsifier and the concentrate is diluted to the desired concentration with water, it being necessary to take into account the volume of soil into which drenching is effected. It should be ensured that a concentration of 40 ppm of emulsifier in the soil is not exceeded. For production of further test concentrations, the mixture is diluted with water.

Savoy cabbage plants (*Brassica oleracea*) in soil pots, infested by all stages of the green peach aphid (*Myzus persicae*), are drenched with an active ingredient formulation of the desired concentration.

After the desired time, the efficacy in % is determined. 100% means that all the aphids have been killed; 0% means that no aphids have been killed.

In this test, for example, the following compounds from the preparation examples show superior efficacy compared to the prior art: see table.

*Phaedon cochleariae*—Spray Test (PHAECO S)

| Solvent: | 14 parts by weight of dimethylformamide |
|---|---|
| Emulsifier: | alkylaryl polyglycol ether |

To produce an appropriate active ingredient formulation, 1 part by weight of active ingredient is dissolved with the specified parts by weight of solvent and made up with water containing an emulsifier concentration of 1000 ppm until the desired concentration is attained. To produce further test concentrations, the mixture is diluted with emulsifier-containing water. If addition of ammonium salts or/and penetrants is required, these are each added to the preparation solution in a concentration of 1000 ppm.

Cabbage leaves (*Brassica oleracea*) are sprayed with an active ingredient formulation of the desired concentration and populated with larvae of the mustard beetle (*Phaedon cochleariae*).

After the desired time, the kill in % is determined. 100% means that all beetle larvae have been killed; 0% means that no beetle larvae have been killed.

In this test, for example, the following compound from the preparation examples shows superior efficacy compared to the prior art: see table.

Diabrotica balteata—Drench Test (DIABBA)

| Solvent: | 7 parts by weight of dimethylformamide |
|---|---|
| Emulsifier: | 2 parts by weight of alkylaryl polyglycol ether |

To produce an appropriate active ingredient formulation, 1 part by weight of active ingredient is mixed with the specified amounts of solvent and emulsifier and the concentrate is diluted to the desired concentration with water, it being necessary to take into account the volume of soil into which drenching is effected. It should be ensured that a concentration of 40 ppm of emulsifier in the soil is not exceeded. For production of further test concentrations, the mixture is diluted with water.

5 maize kernels in each case are sown into soil-filled pots (*Zea mays*) and, the next day, drenched with the active ingredient formulation of the desired concentration. After one day, about 25 L2 larvae of the banded cucumber beetle (*Diabrotica balteata*) were added.

After 8 days, the efficacy in % is determined. 100% means that all 5 plants have germinated and grown; 0% means that no plant has emerged.

In this test, for example, the following compounds from the preparation examples show superior efficacy compared to the prior art: see table.

Meloidogyne Incognita Test (MELGIN D)

| Solvent: | 7 parts by weight of dimethylformamide |
|---|---|
| Emulsifier: | 2.5 parts by weight of alkylaryl polyglycol ether |

To produce an appropriate active ingredient formulation, 1 part by weight of active ingredient is mixed with the specified amounts of solvent and emulsifier and the concentrate is diluted to the desired concentration with water, it being necessary to take into account the volume of soil into which drenching is effected. It should be ensured that a concentration of 20 ppm of emulsifier in the soil is not exceeded. For production of further test concentrations, the mixture is diluted with water.

Pots filled with soil (loamy sand) are drenched with the active ingredient solution. An egg/larvae suspension of the southern root-knot nematode (*Meloidogyne incognita*) is added, and lettuce seeds are scattered over the soil surface and covered with quartz sand. The lettuce seeds germinate and the seedlings develop. The root-knots develop on the roots.

After the desired time, the nematicidal effect is determined with reference to the root-knot formation in %. 100% means that no root-knots were found; 0% means that the number of root-knots on the treated plants corresponds to that on the untreated control.

In this test, for example, the following compounds from the preparation examples show superior efficacy compared to the prior art: see table.

Nilaparvata lugens—Spray Test (NILALU)

| Solvent: | 52.5 parts by weight of acetone |
|---|---|
| | 7 parts by weight of dimethylformamide |
| Emulsifier: | alkylaryl polyglycol ether |

To produce an appropriate active ingredient formulation, 1 part by weight of active ingredient is dissolved with the specified parts by weight of solvent and made up with water containing an emulsifier concentration of 1000 ppm until the desired concentration is attained. To produce further test concentrations, the mixture is diluted with emulsifier-containing water. If addition of ammonium salts or/and penetrants is required, these are each added to the preparation solution in a concentration of 1000 ppm.

Rice plants (*Oryza sativa*) are sprayed with an active ingredient formulation of the desired concentration and then populated with larvae of the brown planthopper (*Nilaparvata lugens*).

After the desired time, the efficacy in % is determined. 100% means that all planthoppers have been killed; 0% means that no planthoppers have been killed.

In this test, for example, the following compounds from the preparation examples show superior efficacy compared to the prior art: see table.

Nezara viridula—Spray Test (NEZARA)

| Solvent: | 52.5 parts by weight of acetone |
|---|---|
| | 7 parts by weight of dimethylformamide |
| Emulsifier: | alkylaryl polyglycol ether |

To produce an appropriate active ingredient formulation, 1 part by weight of active ingredient is dissolved with the specified parts by weight of solvent and made up with water containing an emulsifier concentration of 1000 ppm until the desired concentration is attained. To produce further test concentrations, the mixture is diluted with emulsifier-containing water. If addition of ammonium salts or/and penetrants is required, these are each added to the preparation solution in a concentration of 1000 ppm.

Barley plants (*Hordeum vulgare*) infected with larvae of the southern green shield bug (*Nezara viridula*) are sprayed with an active ingredient formulation of the desired concentration.

After the desired time, the efficacy in % is determined. 100% means that all bugs have been killed; 0% means that no bugs have been killed.

In this test, for example, the following compounds from the preparation examples show superior efficacy compared to the prior art: see table.

| Substance | Structure | Object | Concentration | | % efficacy | dat |
|---|---|---|---|---|---|---|
| Example No. I-01 inventive | 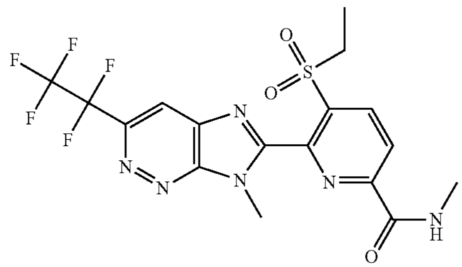 [SMILES: CCS(=O)(=O)c1ccc(C(=O)NC)nc1-c1nc2cc(C(F)(F)C(F)(F)F)nnc2n1C] | PHAECO | 100 | g/ha | 100 | 7 dat |
| | | | 20 | g/ha | 67 | 7 dat |
| | | MYZUPE | 4 | g/ha | 90 | 5 dat |
| | | MELGIN | 20 | ppm | 90 | 14 dat |
| | | APHIGO | 4 | ppm | 100 | 6 dat |
| | | | 0.8 | ppm | 70 | 6 dat |
| | | NILALU | 4 | g/ha | 100 | 4 dat |
| Prior art Ex. I-39 from WO2017/025419 | 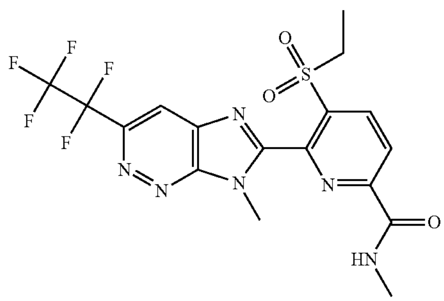 [SMILES: CCS(=O)(=O)c1ccc(C(=O)NC)nc1-c1nc2cc(C(F)(F)C(F)(F)F)nnc2n1C] | PHAECO | 100 | g/ha | 0 | 7 dat |
| | | | 20 | g/ha | 0 | 7 dat |
| | | MYZUPE | 4 | g/ha | 0 | 5 dat |
| | | MELGIN | 20 | ppm | 0 | 14 dat |
| | | APHIGO | 4 | ppm | 55 | 6 dat |
| | | | 0.8 | ppm | 0 | 6 dat |
| | | NILALU | 4 | g/ha | 0 | 4 dat |
| Example No. I-02 inventive | 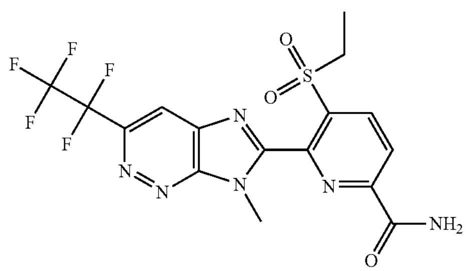 [SMILES: CCS(=O)(=O)c1ccc(C(N)=O)nc1-c1nc2cc(C(F)(F)C(F)(F)F)nnc2n1C] | PHAECO | 4 | g/ha | 100 | 7 dat |
| | | | 0.8 | g/ha | 83 | 7 dat |
| | | MELGIN | 20 | ppm | 90 | 14 dat |
| | | PHAECO S | 20 | ppm | 100 | 7 dat |
| | | NILALU | 20 | ppm | 90 | 4 dat |
| | | NEZAVI | 500 | g/ha | 90 | 4 dat |
| Prior art according to WO2017/025419 | 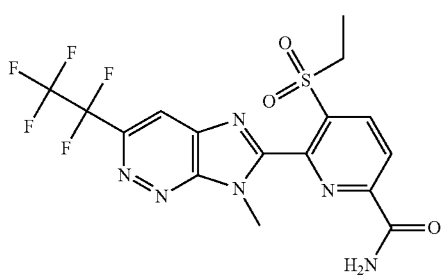 [SMILES: CCS(=O)(=O)c1ccc(C(N)=O)nc1-c1nc2cc(C(F)(F)C(F)(F)F)nnc2n1C] | PHAECO | 4 | g/ha | 33 | 7 dat |
| | | | 0.8 | g/ha | 0 | 7 dat |
| | | MELGIN | 20 | ppm | 0 | 7 dat |
| | | PHAECO S | 20 | ppm | 0 | 14 dat |
| | | NILALU | 20 | g/ha | 50 | 4 dat |
| | | NEZAVI | 500 | g/ha | 0 | 4 dat |
| Example No. I-03 inventive | 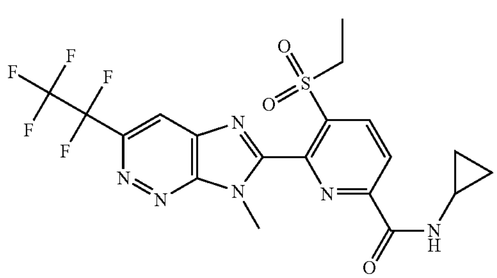 [SMILES: CCS(=O)(=O)c1ccc(C(=O)NC2CC2)nc1-c1nc2cc(C(F)(F)C(F)(F)F)nnc2n1C] | PHAECO | 100 | g/ha | 100 | 7 dat |
| | | | 20 | g/ha | 100 | 7 dat |
| | | MYZUPE | 20 | g/ha | 90 | 5 dat |
| | | NILALU | 100 | g/ha | 100 | 4 dat |
| | | | 20 | g/ha | 80 | 4 dat |
| | | MYZUPE S | 4 | ppm | 100 | 6 dat |
| | | APHIGO | 4 | ppm | 95 | 6 dat |

-continued

| Substance | Structure | Object | Concentration | | % efficacy | dat |
|---|---|---|---|---|---|---|
| Prior art according to WO2017/025419 | 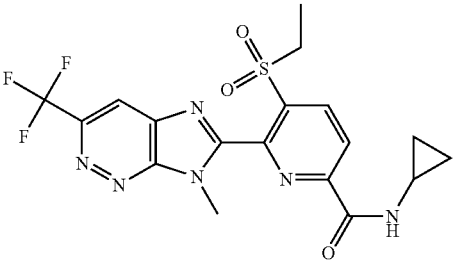 [SMILES: CCS(=O)(=O)c1ccc(C(=O)NC2CC2)nc1-c1nc2cc(C(F)(F)F)nnc2n1C] | PHAECO<br>MYZUPE<br>NILALU<br><br>MYZUPE S<br>APHIGO | 100<br>20<br>20<br>100<br>20<br>4<br>4 | g/ha<br>g/ha<br>g/ha<br>g/ha<br>g/ha<br>ppm<br>ppm | 33<br>33<br>0<br>0<br>0<br>0<br>0 | 7 dat<br>7 dat<br>5 dat<br>4 dat<br>4 dat<br>6 dat<br>6 dat |
| Example No. I-05 inventive | 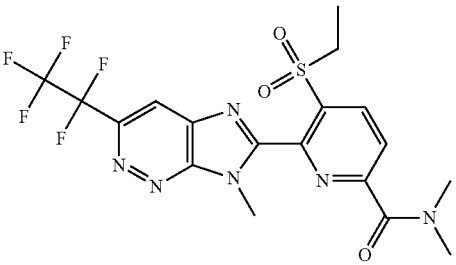 [SMILES: CCS(=O)(=O)c1ccc(C(=O)N(C)C)nc1-c1nc2cc(C(F)(F)C(F)(F)F)nnc2n1C] | PHAECO<br>MYZUPE S<br>APHIGO | 100<br>0.8<br>0.8 | g/ha<br>ppm<br>ppm | 100<br>95<br>65 | 7 dat<br>6 dat<br>6 dat |
| Prior art according to WO2017/025419 | 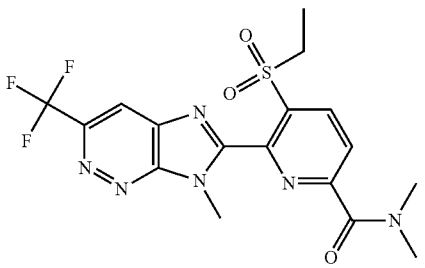 [SMILES: CCS(=O)(=O)c1ccc(C(=O)N(C)C)nc1-c1nc2cc(C(F)(F)F)nnc2n1C] | PHAECO<br>MYZUPE S<br>APHIGO | 100<br>0.8<br>0.8 | g/ha<br>ppm<br>ppm | 33<br>50<br>0 | 7 dat<br>6 dat<br>6 dat |
| Example No. I-06 inventive | 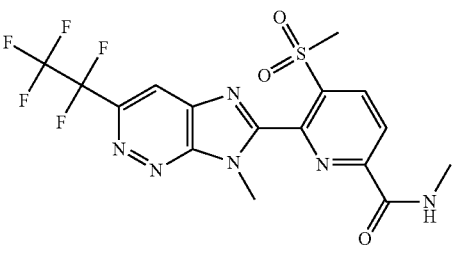 [SMILES: CNC(=O)c1ccc(S(C)(=O)=O)c(-c2nc3cc(C(F)(F)C(F)(F)F)nnc3n2C)n1] | PHAECO<br>MYZUPE | 100<br>100<br>20 | g/ha<br>g/ha<br>g/ha | 67<br>90<br>70 | 7 dat<br>5 dat<br>5 dat |
| Prior art according to WO2017/025419 | 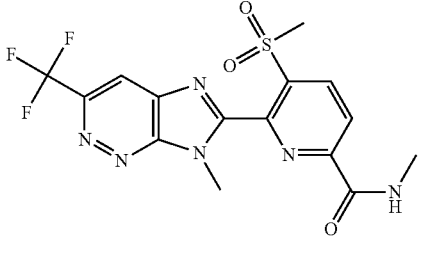 [SMILES: CNC(=O)c1ccc(S(C)(=O)=O)c(-c2nc3cc(C(F)(F)F)nnc3n2C)n1] | PHAECO<br>MYZUPE | 100<br>100<br>20 | g/ha<br>g/ha<br>g/ha | 0<br>0<br>0 | 7 dat<br>5 dat<br>5 dat |
| Example No. I-07 inventive | 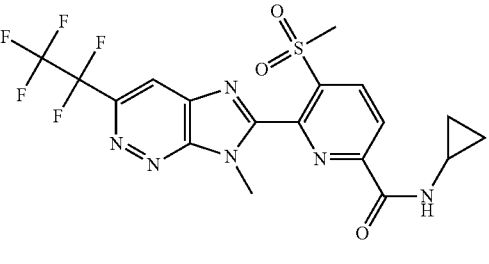 [SMILES: Cn1c(-c2nc(C(=O)NC3CC3)ccc2S(C)(=O)=O)nc2cc(C(F)(F)C(F)(F)F)nnc21] | PHAECO | 100<br>20 | g/ha<br>g/ha | 100<br>100<br>REP | 7 dat<br>7 dat |

-continued

| Substance | Structure | Object | Concentration | | % efficacy | dat |
|---|---|---|---|---|---|---|
| Prior art according to WO2017/025419 | 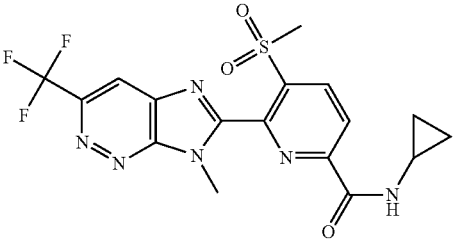 [SMILES: Cn1c(-c2nc(C(=O)NC3CC3)ccc2S(C)(=O)=O)nc2cc(C(F)(F)F)nnc21] | PHAECO | 100<br>20 | g/ha<br>g/ha | 50<br>0 | 7 dat<br>7 dat |
| Example No. I-08 inventive | 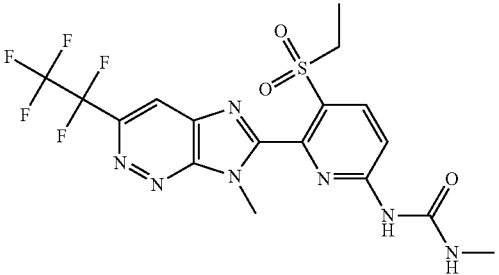 [SMILES: CCS(=O)(=O)c1ccc(NC(=O)NC)nc1-c1nc2cc(C(F)(F)C(F)(F)F)nnc2n1C] | TETRUR<br><br>PHAECO S<br><br>APHIGO<br>DIABBA<br>MELGIN D<br><br>NEZAVI | 100<br>20<br>20<br>4<br>4<br>20<br>2<br>1<br>4 | g/ha<br>g/ha<br>ppm<br>ppm<br>ppm<br>ppm<br>ppm<br>ppm<br>g/ha | 70<br>70<br>90<br>70<br>95<br>100<br>100<br>100<br>90 | 6 dat<br>6 dat<br>7 dat<br>7 dat<br>6 dat<br>8 dat<br>21 dat<br>21 dat<br>4 dat |
| Prior art according to WO2017/025419 | 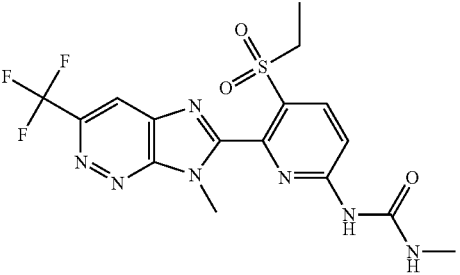 [SMILES: CCS(=O)(=O)c1ccc(NC(=O)NC)nc1-c1nc2cc(C(F)(F)F)nnc2n1C] | TETRUR<br><br>PHAECO S<br><br>APHIGO<br>DIABBA<br>MELGIN D<br><br>NEZAVI | 100<br>20<br>20<br>4<br>4<br>20<br>2<br>1<br>4 | g/ha<br>g/ha<br>ppm<br>ppm<br>ppm<br>ppm<br>ppm<br>ppm<br>g/ha | 0<br>0<br>0<br>0<br>25<br>0<br>50<br>0<br>0 | 6 dat<br>6 dat<br>7 dat<br>7 dat<br>6 dat<br>8 dat<br>21 dat<br>21 dat<br>4 dat |
| Example No. I-09 inventive | 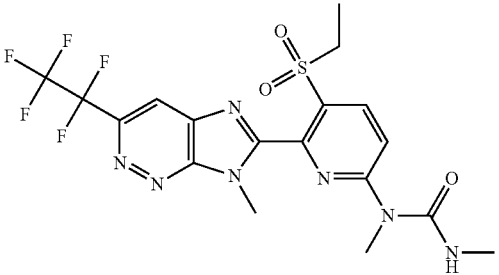 [SMILES: CCS(=O)(=O)c1ccc(N(C)C(=O)NC)nc1-c1nc2cc(C(F)(F)C(F)(F)F)nnc2n1C] | PHAECO<br><br>MYZUPE<br>TETRUR<br>MYZUPE S<br><br>MYZUPE D<br>NEZAVI | 20<br>4<br>4<br>100<br>0.8<br>0.16<br>0.16<br>4 | g/ha<br>g/ha<br>g/ha<br>g/ha<br>ppm<br>ppm<br>ppm<br>g/ha | 100<br>83<br>70<br>70<br>100<br>80<br>99<br>70 | 7 dat<br>7 dat<br>5 dat<br>6 dat<br>6 dat<br>6 dat<br>10 dat<br>4 dat |
| Prior art according to WO2017/025419 | 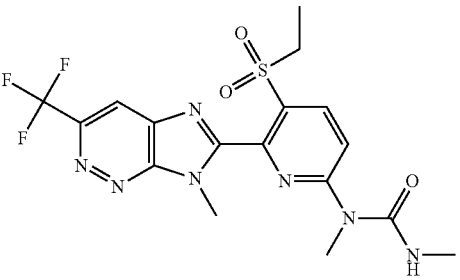 [SMILES: CCS(=O)(=O)c1ccc(N(C)C(=O)NC)nc1-c1nc2cc(C(F)(F)F)nnc2n1C] | PHAECO<br><br>MYZUPE<br>TETRUR<br>MYZUPE S<br><br>MYZUPE D<br>NEZAVI | 20<br>4<br>4<br>100<br>0.8<br>0.16<br>0.16<br>4 | g/ha<br>g/ha<br>g/ha<br>g/ha<br>ppm<br>ppm<br>ppm<br>g/ha | 33<br>0<br>0<br>0<br>65<br>20<br>0<br>0 | 7 dat<br>7 dat<br>5 dat<br>6 dat<br>6 dat<br>6 dat<br>10 dat<br>4 dat |

-continued

| Substance | Structure | Object | Concentration | | % efficacy | dat |
|---|---|---|---|---|---|---|
| Example No. I-10 inventive | 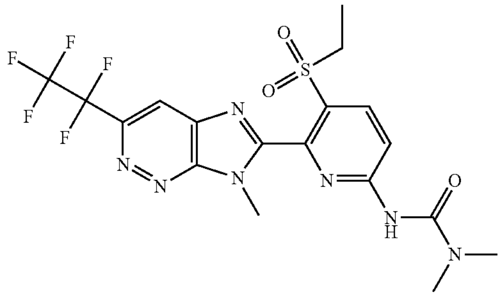 | MYZUPE | 4 | g/ha | 70 | 5 dat |
| | | TETRUR | 100 | g/ha | 70 | 6 dat |
| | | NILALU | 4 | g/ha | 90 | 4 dat |
| | | NEZAVI | 4 | g/ha | 80 | 4 dat |
| | | PHAECO S | 20 | ppm | 80 | 7 dat |
| | | APHIGO | 4 | ppm | 75 | 6 dat |
| Prior art according to WO2017/025419 | | MYZUPE | 4 | g/ha | 0 | 5 dat |
| | | TETRUR | 100 | g/ha | 0 | 6 dat |
| | | NILALU | 4 | g/ha | 0 | 4 dat |
| | | NEZAVI | 4 | g/ha | 0 | 4 dat |
| | | PHAECO S | 20 | ppm | 20 | 7 dat |
| | | APHIGO | 4 | ppm | 15 | 6 dat |
| Example No. I-11 inventive | 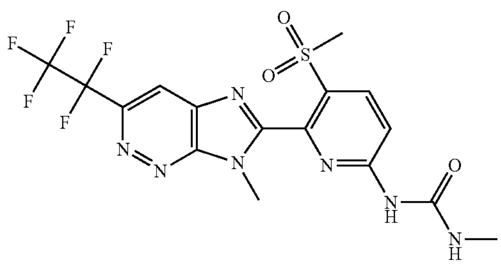 [SMILES: CNC(=O)Nc1ccc(S(C)(=O)=O)c(-c2nc3cc(C(F)(F)C(F)(F)F)nnc3n2C)n1] | PHAECO | 100 | g/ha | 100 | 7 dat |
| | | | 20 | g/ha | 83 | 7 dat |
| | | MYZUPE D | 4 | ppm | 98 | 10 dat |
| | | | 0.8 | ppm | 95 | 10 dat |
| | | APHIGO | 20 | ppm | 95 | 6 dat |
| | | NEZAVI | 20 | g/ha | 100 | 4 dat |
| Prior art according to WO2017/025419 | | PHAECO | 100 | g/ha | 33 | 7 dat |
| | | | 20 | g/ha | 0 | 7 dat |
| | | MYZUPE D | 4 | ppm | 0 | 10 dat |
| | | | 0.8 | ppm | 0 | 10 dat |
| | | APHIGO | 20 | ppm | 0 | 6 dat |
| | | NEZAVI | 20 | g/ha | 0 | 4 dat |
| Example No. I-12 inventive | 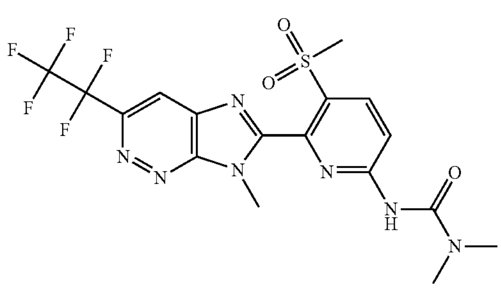 [SMILES: CN(C)C(=O)Nc1ccc(S(C)(=O)=O)c(-c2nc3cc(C(F)(F)C(F)(F)F)nnc3n2C)n1] | PHAECO | 100 | g/ha | 100 | 7 dat |
| | | | 20 | g/ha | 100 | 7 dat |
| | | MYZUPE | 100 | g/ha | 90 | 5 dat |
| | | | 20 | g/ha | 90 | 5 dat |
| | | MELGIN | 20 | ppm | 100 | 14 dat |

-continued

| Substance | Structure | Object | Concentration | | % efficacy | dat |
|---|---|---|---|---|---|---|
| Prior art according to WO2017/025419 | | PHAECO | 100 | g/ha | 0 | 7 dat |
| | | | 20 | g/ha | 0 | 7 dat |
| | | MYZUPE | 100 | g/ha | 0 | 5 dat |
| | | | 20 | g/ha | 0 | 5 dat |
| | | MELGIN | 20 | ppm | 0 | 14 dat |
| Example No. I-13 inventive | 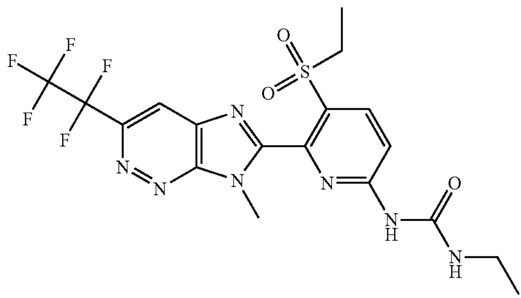 [SMILES: CCNC(=O)Nc1ccc(S(=O)(=O)CC)c(-c2nc3cc(C(F)(F)C(F)(F)F)nnc3n2C)n1] | PHAECO | 100 | g/ha | 100 | 7 dat |
| | | | 20 | g/ha | 100 | 7 dat |
| | | | 4 | g/ha | 100 | 7 dat |
| | | NEZAVI | 4 | g/ha | 80 | 4 dat |
| Prior art according to WO2017/025419 | | PHAECO | 100 | g/ha | 50 | 7 dat |
| | | | 20 | g/ha | 67 | 7 dat |
| | | | 4 | g/ha | 0 | 7 dat |
| | | NEZAVI | 4 | g/ha | 0 | 4 dat |
| Example No. I-14 inventive | 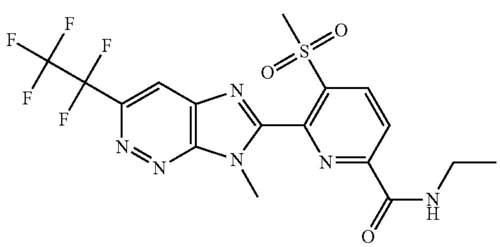 [SMILES: CCNC(=O)c1ccc(S(C)(=O)=O)c(-c2nc3cc(C(F)(F)C(F)(F)F)nnc3n2C)n1] | PHAECO | 100 | g/ha | 100 | 7 dat |
| | | | 20 | g/ha | 83 | 7 dat |
| Prior art according to WO2017/025419 | | PHAECO | 100 | g/ha | 0 | 7 dat |
| | | | 20 | g/ha | 0 | 7 dat |

| Substance | Structure | Object | Concentration | | % efficacy | dat |
|---|---|---|---|---|---|---|
| Example No. I-15 inventive | 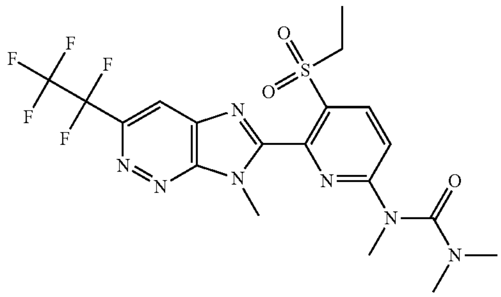 [SMILES: CCS(=O)(=O)c1ccc(N(C)C(=O)N(C)C)nc1-c1nc2cc(C(F)(F)C(F)(F)F)nnc2n1C] | PHAECO | 100 | g/ha | 100 | 7 dat |
| | | | 20 | g/ha | 83 | 7 dat |
| | | NEZAVI | 4 | g/ha | 100 | 4 dat |
| | | | 0.8 | g/ha | 80 | 4 dat |
| Prior art according to WO2017/025419 | 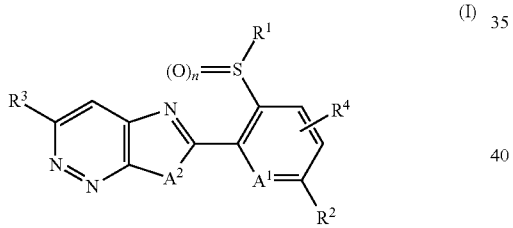 | PHAECO | 100 | g/ha | 0 | 7 dat |
| | | | 20 | g/ha | 0 | 7 dat |
| | | NEZAVI | 4 | g/ha | 50 | 4 dat |
| | | | 0.8 | g/ha | 0 | 4 dat |

REP = repellent effect

The invention claimed is:

1. Compound of formula (I)

(I)

in which $A^1$ is nitrogen, $=N^+(O^-)-$, or $=C(R^5)-$, $A^2$ is $-N(R^6)-$, $R^1$ is $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-haloalkoxy-$(C_1-C_6)$-alkyl, $(C_2-C_6)$-alkenyl, $(C_2-C_6)$-alkenyloxy-$(C_1-C_8)$-alkyl, $(C_2-C_6)$-haloalkenyloxy-$(C_1-C_6)$-alkyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_6)$-alkyl, $(C_2-C_8)$-haloalkynyloxy-$(C_1-C_6)$-alkyl, $(C_2-C_6)$-haloalkynyl, $(C_2-C_6)$-cyanoalkynyl, $(C_3-C_5)$-cycloalkyl, $(C_3-C_6)$-halocycloalkyl, $(C_3-C_6)$-cyanocycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, amino, $(C_1-C_6)$-alkylamino, di-$(C_1-C_6)$-alkyl-amino, $(C_3-C_8)$-cycloalkylamino, $(C_1-C_6)$-alkylcarbonylamino, $(C_1-C_8)$-alkylthio-$(C_1-C_6)$-alkyl, $(C_1-C_6)$-haloalkylthio-$(C_1-C_6)$-alkyl, $(C_1-C_6)$-alkylsulfinyl-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-alkyl, $(C_1-C_6)$-haloalkylsulfonyl-$(C_1-C_6)$-alkyl, $(C_1-C_6)$-alkoxy-$(C_1-C_6)$-alkylthio-$(C_1-C_6)$-alkyl, $(C_1-C_6)$-alkoxy-$(C_1-C_6)$-alkylsulfinyl-$(C_1-C_6)$-alkyl, $(C_1-C_6)$-alkoxy-$(C_1-C_6)$-alkylsulfonyl-$(C_1-C_6)$-alkyl, $(C_1-C_6)$-alkylcarbonyl-$(C_1-C_6)$-alkyl, $(C_1-C_6)$-haloalkylcarbonyl-$(C_1-C_6)$-alkyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkylsulfonylamino, aminosulfonyl)-$C_1-C_6)$-alkyl, $(C_1-C_6)$-alkylaminosulfonyl-$(C_1-C_6)$-alkyl, di-$(C_1-C_6)$-alkylaminosulfonyl-$(C_1-C_6)$-alkyl, or is in each case optionally identically or differently mono- or poly-aryl-, -hetaryl- or -heterocyclyl-substituted $(C_1-C_6)$-alkyl, $(C_1-C_6)$-alkoxy, $(C_2-C_6)$-alkenyl, $(C_2-C_6)$-alkynyl, $(C_3-C_8)$-cycloalkyl, where aryl, hetaryl or heterocyclyl may each optionally be mono- or polysubstituted identically or differently by halogen, cyano, nitro, hydroxyl, amino, carboxyl, carbamoyl, aminosulfonyl, $(C_1-C_6)$-alkyl, $(C_3-C_6)$-cycloalkyl, $(C_1-C_6)$-alkoxy, $(C_1-C_6)$-haloalkyl, $(C_1-C_6)$-haloalkoxy, $(C_1-C_6)$-alkylthio, $(C_1-C_6)$-alkylsulfinyl, $(C_1-C_6)$-alkylsulfonyl, $(C_1-C_6)$-alkylsulfimino, $(C_1-C_6)$-alkylsulfimino-$(C_1-C_6)$-alkyl, $(C_1-C_6)$-alkylsulfimino-$(C_2-C_6)$-alkylcarbonyl, $(C_1-C_6)$-alkylsulfoximino, $(C_1-C_6)$-alkylsulfoximino-$(C_1-C_6)$-alkyl, $(C_1-C_6)$-alkylsulfoximino-$(C_2-C_6)$-alkylcarbonyl, $(C_1-C_6)$-alkoxycarbonyl, $(C_1-C_6)$-alkylcarbonyl, $(C_3-C_6)$-trialkylsilyl or benzyl, $R^2$ is a group selected from $-C(=O)-NR^{11}R^{12}$, $-C(=S)-NR^{11}R^{12}$, $-NR^{11}R^{12}$, $NR^{11}-C(=O)-R^8$ and $-NR^{11}-C(=S)-R^8$, $R^3$ is $C_2$-haloalkyl, $R^4$ is hydrogen, cyano, halogen, nitro, acetyl, hydroxyl, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, cyano-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), is in each case optionally singly or multiply, identically or differently substituted aryl or hetaryl, where (in the case of hetaryl) at least one carbonyl group may optionally be present and where possible substituents in each case are as follows: cyano, carboxyl, halogen, nitro, acetyl, hydroxyl, amino, SCN, tri-($C_1$-$C_6$) alkylsilyl, ($C_3$-$C_8$)cycloalkyl, ($C_3$-$C_6$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di-($C_1$-$C_6$)alkylaminocarbonyl, ($C_2$-$C_6$)alkenylaminocarbonyl, di-($C_2$-$C_5$)-alkenylaminocarbonyl, ($C_3$-$C_8$)cycloalkylaminocarbonyl, ($C_1$-$C_6$)alkylsulfonylamino, ($C_1$-$C_6$)alkylamino, di-($C_1$-$C_6$)alkylamino, aminosulfonyl, ($C_1$-$C_6$)alkylaminosulfonyl, di-($C_1$-$C_6$)alkylaminosulfonyl, ($C_1$-$C_6$)alkylsulfoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, ($C_1$-$C_6$)alkylcarbonylamino, $R^5$ is hydrogen, cyano, halogen, nitro, acetyl, hydroxyl, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkyl-aminocarbonyl, di-($C_1$-$C_6$)-alkyl-aminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkyl-aminosulfonyl, ($C_1$-$C_6$)-alkylsulfoximino, aminothiocarbonyl, ($C_1$-$C_6$)-alkylaminothiocarbonyl, di-($C_1$-$C_6$)-alkyl-aminothiocarbonyl, ($C_3$-$C_8$)-cycloalkylamino or —NHCO—($C_1$-$C_6$)-alkyl (($C_1$-$C_6$)-alkylcarbonylamino), $R^6$ is ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)haloalkoxy-($C_1$-$C_6$)alkyl, ($C_2$-$C_6$)alkenyl, ($C_2$-$C_6$)alkenyloxy-($C_1$-$C_6$)alkyl, ($C_2$-$C_6$)haloalkenyloxy-($C_1$-$C_6$)alkyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_6$)alkyl, ($C_2$-$C_6$)haloalkynyloxy-($C_1$-$C_6$)alkyl, ($C_2$-$C_6$)haloalkynyl, ($C_2$-$C_6$)cyanoalkynyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkylthio-($C_1$-$C_6$)alkyl, ($C_1$-$C_6$)haloalkylthio-($C_1$-$C_6$)alkyl, ($C_1$-$C_6$)alkylsulfinyl-($C_1$-$C_6$)alkyl, ($C_1$-$C_6$)haloalkylsulfinyl-($C_1$-$C_6$)alkyl, ($C_1$-$C_6$)alkylsulfonyl-($C_1$-$C_6$)alkyl, ($C_1$-$C_6$)haloalkylsulfonyl-($C_1$-$C_6$)alkyl, ($C_1$-$C_6$)alkoxy-($C_1$-$C_6$)alkylthio-($C_1$-$C_6$)alkyl, ($C_1$-$C_6$)alkoxy-($C_1$-$C_6$)alkylsulfinyl-($C_1$-$C_6$)alkyl, ($C_1$-$C_6$)alkoxy-($C_1$-$C_6$)alkylsulfonyl-($C_1$-$C_6$)alkyl, ($C_1$-$C_6$)alkylcarbonyl-($C_1$-$C_6$)alkyl, ($C_1$-$C_6$)haloalkylcarbonyl-($C_1$-$C_6$)alkyl, ($C_1$-$C_6$)alkoxycarbonyl-($C_1$-$C_6$)alkyl, ($C_1$-$C_6$)haloalkoxycarbonyl-($C_1$-$C_6$)alkyl, aminocarbonyl-($C_1$-$C_6$)alkyl, ($C_1$-$C_6$)alkylamino-($C_1$-$C_6$)alkyl, di-($C_1$-$C_6$)alkylamino-($C_1$-$C_6$)alkyl or ($C_3$-$C_8$)cycloalkylamino-($C_1$-$C_6$)alkyl, R$^8$ is amino or in each case optionally singly or multiply, identically or differently substituted C$_1$-C$_4$-alkylamino, di-(C$_1$-C$_4$)-alkylamino, C$_2$-C$_6$-alkenylamino, C$_2$-C$_6$-alkynylamino, C$_3$-C$_{12}$-cycloalkylamino, C$_3$-C$_{12}$-cycloalkyl-(C$_1$-C$_6$)-alkylamino, C$_4$-C$_{12}$-bicycloalkylamino or hydrazino, where the substituents may independently be selected from halogen, cyano, nitro, hydroxyl, (C=O)OH, C$_1$-C$_6$-alkyl, C$_3$-C$_6$-cycloalkyl, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, C$_2$-C$_6$-alkoxycarbonyl, C$_2$-C$_6$-alkylcarbonyl, C$_1$-C$_6$-alkylthiocarbonyl, C$_1$-C$_6$-haloalkylcarbonyl, C$_1$-C$_6$-haloalkylthiocarbonyl, C$_1$-C$_6$-alkylcarbonylamino, aminocarbonyl, C$_1$-C$_6$-alkylaminocarbonyl, di-(C$_1$-C$_6$)-alkylaminocarbonyl, aminothiocarbonyl, C$_1$-C$_6$-alkylaminothiocarbonyl, di-(C$_1$-C$_6$)-alkylaminothiocarbonyl, C$_3$-C$_6$-trialkylsilyl, amino, C$_1$-C$_4$-alkylamino, di-(C$_1$-C$_4$-alkyl)amino, C$_3$-C$_6$-cycloalkylamino, aminosulfonyl, C$_1$-C$_6$-alkylaminosulfonyl, di-(C$_1$-C$_6$)-alkylaminosulfonyl, sulfonylamino, C$_1$-C$_6$-alkylsulfonylamino and di-(C$_1$-C$_6$)-alkylsulfonylamino, R$^{11}$, R$^{12}$ are independently hydrogen or in each case optionally singly or multiply, identically or differently substituted C$_1$-C$_6$-alkyl, C$_2$-C$_6$-alkenyl, C$_2$-C$_6$-alkynyl, C$_3$-C$_{12}$-cycloalkyl, C$_3$-C$_{12}$-cycloalkyl-C$_1$-C$_6$-alkyl or C$_4$-C$_{12}$-bicycloalkyl, where the substituents may independently be selected from halogen, cyano, nitro, hydroxyl, C$_1$-C$_6$-alkyl, C$_3$-C$_6$-cycloalkyl, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-alkylsulfimino, C$_1$-C$_4$-alkylsulfimino-C$_1$-C$_4$-alkyl, C$_1$-C$_4$-alkylsulfimino-C$_2$-C$_5$-alkylcarbonyl, C$_1$-C$_4$-alkylsulfoximino, C$_1$-C$_4$-alkylsulfoximino-C$_1$-C$_4$-alkyl, C$_1$-C$_4$-alkylsulfoximino-C$_2$-C$_5$-alkylcarbonyl, C$_2$-C$_6$-alkoxycarbonyl, C$_2$-C$_6$-alkylcarbonyl, C$_3$-C$_6$-trialkylsilyl, amino, C$_1$-C$_4$-alkylamino, di-(C$_1$-C$_4$-alkyl)amino, C$_3$-C$_6$-cycloalkylamino, a phenyl ring and a 3- or 6-membered aromatic partly saturated or saturated heterocycle, where the phenyl ring or heterocycle may in each case optionally be mono- or polysubstituted identically or differently, and where the substituents may independently be selected from C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, cyano, (C=O)OH, CONH$_2$, NO$_2$, OH, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, C$_1$-C$_4$-alkylamino, di-(C$_1$-C$_4$-alkyl)amino, C$_3$-C$_6$-cycloalkylamino, (C$_1$-C$_6$-alkyl)carbonyl, (C$_1$-C$_6$-alkoxy)carbonyl, (C$_1$-C$_6$-alkyl)aminocarbonyl, di-(C$_1$-C$_4$-alkyl)aminocarbonyl, tri-(C$_1$-C$_2$)alkylsilyl, (C$_1$-C$_4$-alkyl)(C$_1$-C$_4$-alkoxy)imino or R$^{11}$, R$^{12}$ are independently a phenyl ring or a 3- to 6-membered aromatic partly saturated or saturated heterocycle, where the heteroatoms are selected from the group of N, S and O, where the phenyl ring or heterocycle may in each case optionally be mono- or polysubstituted identically or differently, and where the substituents may independently be selected from C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, cyano, (C=O)OH, CONH$_2$, NO$_2$, OH, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, C$_1$-C$_4$-alkylamino, di-(C$_1$-C$_4$-alkyl)amino, C$_3$-C$_6$-cycloalkylamino, (C$_1$-C$_6$-alkyl)carbonyl, (C$_1$-C$_6$-alkoxy)carbonyl, (C$_1$-C$_6$-alkyl)aminocarbonyl, di-(C$_1$-C$_4$-alkyl)aminocarbonyl, tri-(C$_1$-C$_2$)alkylsilyl and (C$_1$-C$_4$-alkyl)(C$_1$-C$_4$-alkoxy)imino, and n is 0, 1 or 2.

2. Compound of formula (I) according to claim 1 wherein
A$^1$ is nitrogen, =N$^+$(O$^-$)— or =C(R$^5$)—,
A$^2$ is —N(R$^6$)—,
R$^1$ is (C$_1$-C$_4$)alkyl, (C$_1$-C$_4$)hydroxyalkyl, (C$_1$-C$_4$)haloalkyl, (C$_1$-C$_4$)cyanoalkyl, (C$_1$-C$_4$)alkoxy-(C$_1$-C$_4$)alkyl, (C$_1$-C$_4$)haloalkoxy-(C$_1$-C$_4$)alkyl, (C$_2$-C$_4$)alkenyl, (C$_2$-C$_4$)alkenyloxy-(C$_1$-C$_4$)alkyl, (C$_2$-C$_4$)haloalkenyloxy-(C$_1$-C$_4$)alkyl, (C$_2$-C$_4$)haloalkenyl, (C$_2$-C$_4$)cyanoalkenyl, (C$_2$-C$_4$)alkynyl, (C$_2$-C$_4$)alkynyloxy-(C$_1$-C$_4$)alkyl, (C$_2$-C$_4$)haloalkynyloxy-(C$_1$-C$_4$)alkyl, (C$_2$-C$_4$)haloalkynyl, (C$_2$-C$_4$)cyanoalkynyl, (C$_3$-C$_6$)cycloalkyl, (C$_3$-C$_6$)-halocycloalkyl, (C$_3$-C$_6$)-cyanocycloalkyl, (C$_3$-C$_6$)cycloalkyl(C$_3$-C$_6$)cycloalkyl, (C$_1$-C$_4$)alkyl-(C$_3$-C$_6$)cycloalkyl, halo(C$_3$-C$_6$)cycloalkyl, (C$_1$-C$_4$)alkylamino, di-(C$_1$-C$_4$)alkyl-amino, (C$_3$-C$_6$)cycloalkylamino, (C$_1$-C$_4$)alkylcarbonyl-amino, (C$_1$-C$_4$)alkylthio-(C$_1$-C$_4$)alkyl, (C$_1$-C$_4$)haloalkylthio-(C$_1$-C$_4$)alkyl, (C$_1$-C$_4$)alkylsulfinyl-(C$_1$-C$_4$)alkyl, (C$_1$-C$_4$)haloalkylsulfinyl-(C$_1$-C$_4$)alkyl, (C$_1$-C$_4$)alkylsulfonyl-(C$_1$-C$_4$)alkyl, (C$_1$-C$_4$)alkylcarbonyl-(C$_1$-C$_4$)alkyl, (C$_1$-C$_4$)haloalkylcarbonyl-(C$_1$-C$_4$)alkyl, (C$_1$-C$_4$)alkylsulfonylamino, or is in each case optionally identically or differently mono- or di-aryl-, -hetaryl- or -heterocyclyl-substituted (C$_1$-C$_4$)alkyl, (C$_1$-C$_4$)alkoxy, (C$_2$-C$_4$)alkenyl, (C$_2$-C$_4$)alkynyl or (C$_3$-C$_6$)cycloalkyl, where aryl, hetaryl or heterocyclyl are each optionally identically or differently mono- or disubstituted by halogen, cyano, carbamoyl, aminosulfonyl, (C$_1$-C$_4$)alkyl, (C$_3$-C$_4$)cycloalkyl, (C$_1$-C$_4$)alkoxy, C$_1$-C$_4$)haloalkyl, (C$_1$-C$_4$)haloalkoxy, (C$_1$-C$_4$)alkylthio, (C$_1$-C$_4$)alkylsulfinyl, (C$_1$-C$_4$)alkylsulfonyl, (C$_1$-C$_4$)alkylsulfimino, R$^2$ is —C(=O)—NR$^{11}$R$^{12}$, —C(=S)—NR$^{11}$R$^{12}$, —NR$^{11}$R$^{12}$, —NR$^{11}$—C(=O)—R$^8$ or —NR$^{11}$—C(=S)—R$^8$, R$^3$ is C$_2$-haloalkyl, R$^4$ is hydrogen, cyano, halogen, nitro, acetyl, hydroxyl, amino, SCN, tri-(C$_1$-C$_4$)alkylsilyl, (C$_3$-C$_6$)cycloalkyl, (C$_3$-C$_6$)cycloalkyl-(C$_3$-C$_6$)cycloalkyl, (C$_1$-C$_4$)alkyl-(C$_3$-C$_6$)cycloalkyl, halo(C$_3$-C$_6$)cycloalkyl, cyano(C$_3$-C$_8$)-cycloalkyl, (C$_1$-C$_4$)alkyl, (C$_1$-C$_4$)haloalkyl, (C$_1$-C$_4$)cyanoalkyl, (C$_1$-C$_4$)hydroxyalkyl, (C$_1$-C$_4$)alkoxy-(C$_1$-C$_4$)alkyl, (C$_2$-C$_4$)alkenyl, (C$_2$-C$_4$)haloalkenyl, (C$_2$-C$_4$)cyanoalkenyl, (C$_2$-C$_4$)alkynyl, (C$_2$-C$_4$)haloalkynyl, (C$_2$-C$_4$)cyanoalkynyl, (C$_1$-C$_4$)alkoxy, (C$_1$-C$_4$)haloalkoxy, (C$_1$-C$_4$)cyanoalkoxy, (C$_1$-C$_4$)alkoxy-(C$_1$-C$_4$)alkoxy, (C$_1$-C$_4$)alkylhydroxyimino, (C$_1$-C$_4$)alkoxyimino, (C$_1$-C$_4$)alkyl-(C$_1$-C$_4$)alkoxyimino, (C$_1$-C$_4$)haloalkyl-(C$_1$-C$_4$)alkoxyimino, (C$_1$-C$_4$)alkylthio, (C$_1$-C$_4$)haloalkylthio, (C$_1$-C$_4$)alkylthio-(C$_1$-C$_4$)alkyl, (C$_1$-C$_4$)alkylsulfinyl, (C$_1$-C$_4$)haloalkylsulfinyl, (C$_1$-C$_4$)alkylsulfinyl-(C$_1$-C$_4$)alkyl, (C$_1$-C$_4$)alkylsulfonyl, (C$_1$-C$_4$)haloalkylsulfonyl, (C$_1$-C$_4$)alkylsulfonyl-(C$_1$-C$_4$)alkyl, (C$_1$-C$_4$)alkylsulfonyloxy, (C$_1$-C$_4$)alkylcarbonyl, (C$_1$-C$_4$)haloalkylcarbonyl, aminocarbonyl, aminothiocarbonyl, (C$_1$-C$_4$)alkylaminocarbonyl, di-(C$_1$-C$_4$)alkylaminocarbonyl, (C$_1$-C$_4$)alkylsulfonylamino, (C$_1$-C$_4$)

alkylamino, di-($C_1$-$C_4$)alkylamino, aminosulfonyl, ($C_1$-$C_4$)alkylaminosulfonyl, di-($C_1$-$C_4$)alkylaminosulfonyl, aminothiocarbonyl, NHCO—($C_1$-$C_4$)alkyl (($C_1$-$C_4$)alkylcarbonylamino), and also is phenyl or hetaryl, each of which is optionally mono- or disubstituted identically or differently, where (in the case of hetaryl) at least one carbonyl group may optionally be present and where possible substituents are in each case as follows: cyano, halogen, nitro, acetyl, amino, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkylaminosulfonyl, NHCO—($C_1$-$C_4$)alkyl (($C_1$-$C_4$)alkylcarbonylamino), $R^5$ is hydrogen, cyano, halogen, nitro, acetyl, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl)-$C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di-($C_1$-$C_4$)alkylaminocarbonyl, ($C_1$-$C_4$)alkylsulfonylamino, ($C_1$-$C_4$)alkylamino, di-($C_1$-$C_4$)alkylamino, aminosulfonyl, ($C_1$-$C_4$)alkylaminosulfonyl, di-($C_1$-$C_4$)alkylaminosulfonyl, aminothiocarbonyl or NHCO—($C_1$-$C_4$)alkyl (($C_1$-$C_4$)alkylcarbonylamino), $R^6$ is ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulfinyl-($C_1$-$C_4$)alkyl, ($C_1$-$C_4$)haloalkylsulfinyl-($C_1$-$C_4$)alkyl, ($C_1$-$C_4$)alkylsulfonyl-($C_1$-$C_4$)alkyl, ($C_1$-$C_4$)haloalkylsulfonyl-($C_1$-$C_4$)alkyl, ($C_1$-$C_4$) alkoxy-($C_1$-$C_4$)alkylthio-($C_1$-$C_4$)alkyl or ($C_1$-$C_4$)alkylcarbonyl-($C_1$-$C_4$)alkyl, $R^8$ is amino, in each case optionally singly or multiply, identically or differently substituted $C_1$-$C_4$-alkylamino, di-($C_1$-$C_4$)-alkylamino, $C_2$-$C_6$-alkenylamino, $C_2$-$C_6$-alkynylamino, $C_3$-$C_{12}$-cycloalkylamino, $C_3$-$C_{12}$-cycloalkyl-($C_1$-$C_6$)-alkylamino, $C_4$-$C_{12}$-bicycloalkylamino or hydrazino, where the substituents may independently be selected from halogen, cyano, amino, $C_1$-$C_6$-alkyl, $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, a phenyl ring and a 3- to 6-membered aromatic partly saturated or saturated heterocycle, where the phenyl ring or heterocycle may in each case optionally be mono- or polysubstituted identically or differently, and where the substituents may independently be selected from $C_1$-$C_4$-alkyl, $C_1$-$C_4$-haloalkyl, halogen, cyano, $NO_2$, $C_1$-$C_4$-alkoxy or $C_1$-$C_4$-haloalkoxy, or $R^{11}$, $R^{12}$ are independently hydrogen, in each case optionally singly or multiply, identically or differently substituted $C_1$-$C_4$-alkyl or $C_3$-$C_6$-cycloalkyl, where the substituents may independently be selected from halogen, cyano, a phenyl ring and a 3- to 6-membered aromatic partly saturated or saturated heterocycle, where the phenyl ring or heterocycle may in each case optionally be mono- or polysubstituted identically or differently, and where the substituents may independently be selected from $C_1$-$C_4$-alkyl, $C_1$-$C_4$-haloalkyl, halogen, cyano, $NO_2$, $C_1$-$C_4$-alkoxy or $C_1$-$C_4$-haloalkoxy, or $R^{11}$, $R^{12}$ are independently a phenyl ring or a 3- to 6-membered aromatic partly saturated or saturated heterocycle, where the heteroatoms are selected from the group of N, S, O, where the phenyl ring or heterocycle may in each case optionally be mono- or polysubstituted identically or differently, and where the substituents may independently be selected from $C_1$-$C_4$-alkyl, $C_1$-$C_4$-haloalkyl, halogen or cyano, and n is 0, 1 or 2.

3. Compound of formula (I) according to claim 1 wherein $A^1$ is nitrogen or =C($R^5$)—, $A^2$ is —N($R^6$)—, $R^1$ is ($C_1$-$C_4$)-alkyl, ($C_1$-$C_4$)-hydroxyalkyl, ($C_1$-$C_4$)-haloalkyl, ($C_2$-$C_4$)-alkenyl, ($C_2$-$C_4$)-haloalkenyl, ($C_2$-$C_4$)-alkynyl, ($C_2$-$C_4$)-haloalkynyl, ($C_3$-$C_6$)-cycloalkyl, ($C_1$-$C_4$)-alkylthio-($C_1$-$C_4$)-alkyl, ($C_1$-$C_4$)-alkylsulfinyl-($C_1$-$C_4$)-alkyl or ($C_1$-$C_4$)-alkylsulfonyl-($C_1$-$C_4$)-alkyl, $R^2$ is —C(=O)—$NR^{11}R^{12}$, —C(=S)—$NR^{11}R^{12}$, —$NR^{11}R^{12}$, —$NR^{11}$—C(=O)—$R^8$ or —$NR^{11}$—C(=S)—$R^8$, $R^3$ is $C_2$-haloalkyl, $R^4$ is hydrogen, cyano, halogen, nitro, hydroxyl, amino, ($C_3$-$C_6$)cycloalkyl, cyano($C_3$-$C_8$)-cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkylthio, ($C_1$-

$C_4$)haloalkylthio, $(C_1-C_4)$alkylsulfinyl, $(C_1-C_4)$haloalkylsulfinyl, $(C_1-C_4)$alkylsulfonyl or $(C_1-C_4)$haloalkylsulfonyl, $R^5$ is hydrogen, halogen, cyano or $(C_1-C_4)$alkyl, $R^6$ is $(C_1-C_4)$alkyl or $(C_1-C_4)$alkoxy-$(C_1-C_4)$alkyl, $R^8$ is amino, in each case optionally mono-halogen-, -cyano-, —$C_1$-$C_4$-alkoxy-, —$C_1$-$C_4$-alkylthio-, —$C_1$-$C_4$-alkylsulfinyl-, —$C_1$-$C_4$-alkylsulfonyl-, -phenyl- or -pyridyl-substituted $(C_1-C_4)$alkylamino, di-$(C_1-C_4)$-alkylamino, $(C_2-C_6)$-alkenylamino, $(C_2-C_4)$-alkynylamino, $(C_3-C_6)$-cycloalkylamino or hydrazino, $R^{11}$, $R^{12}$ are independently hydrogen, in each case optionally mono-halogen-, -cyano-, -phenyl- or -pyridyl-substituted $(C_1-C_4)$alkyl or $(C_3-C_6)$cycloalkyl and n is 0, 1 or 2.

4. Compound of formula (I) according to claim 1, wherein $A^1$ is nitrogen or =C($R^5$)—, $A^2$ is —N($R^6$)—, $R^1$ is $(C_1-C_4)$alkyl, $(C_1-C_4)$haloalkyl or $(C_3-C_6)$cycloalkyl, $R^2$ is —C(=O)—$NR^{11}R^{12}$ where $R^{11}$, $R^{12}$ are each independently hydrogen, $(C_1-C_4)$alkyl or $(C_3-C_6)$cycloalkyl or $R^2$ is —$NR^{11}$—C(=O)—$R^8$ where $R^8$ is $(C_2-C_6)$-alkenylamino, $(C_2-C_4)$-alkynylamino, $(C_3-C_6)$-cycloalkylamino, $(C_1-C_4)$-alkylamino, or hydrazino and $R^{11}$ is hydrogen, $(C_3-C_6)$cycloalkyl or $(C_1-C_4)$alkyl, $R^3$ is fluoroethyl, difluoroethyl, trifluoroethyl, tetrafluoroethyl or pentafluoroethyl, $R^4$ is hydrogen, cyano, halogen, $(C_1-C_4)$alkyl, $(C_1-C_4)$haloalkyl, $(C_1-C_4)$haloalkoxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl, $(C_1-C_4)$haloalkylsulfonyl or $(C_1-C_4)$alkylcarbonylamino, $R^5$ is hydrogen, fluorine, chlorine, bromine or cyano, $R^6$ is methyl, ethyl, i-propyl, methoxymethyl or methoxyethyl and n is 0, 1 or 2.

5. Compound of formula (I) according to claim 1, wherein $A^1$ is nitrogen, $A^2$ is —NMe, $R^1$ is methyl, ethyl, n-propyl, i-propyl or cyclopropyl, $R^2$ is —C(=O)—$NR^{11}R^{12}$ where $R^{11}$ is hydrogen or $(C_1-C_4)$alkyl and $R^{12}$ is hydrogen, $(C_1-C_4)$alkyl or $(C_3-C_6)$cycloalkyl, or $R^2$ is —$NR^{11}$—C(=O)—$R^8$ where $R^8$ is $(C_1-C_4)$alkylamino or di-$(C_1-C_4)$alkylamino and $R^{11}$ is hydrogen or $(C_1-C_4)$alkyl and $R^3$ is pentafluoroethyl or tetrafluoroethyl (—$CF_2CF_2H$ or $CFHCF_3$), $R^4$ is hydrogen and n is 0 or 2.

6. Compound of formula (I) according to claim 1, wherein $A^1$ is nitrogen, $A^2$ is —NMe, $R^1$ is ethyl or methyl, $R^2$ is —C(=O)—$NR^{11}R^{12}$ where $R^{11}$ is hydrogen or methyl and $R^{12}$ is hydrogen, methyl, cyclopropyl or ethyl or $R^2$ is —$NR^{11}$—C(=O)—$R^8$ where $R^8$ is methylamino (—NHMe), ethylamino (—NHEt) or dimethylamino (—N(Me)$_2$) and $R^{11}$ is hydrogen or methyl and $R^3$ is pentafluoroethyl, $R^4$ is hydrogen and n is 2.

7. Compound of formula (I-1)

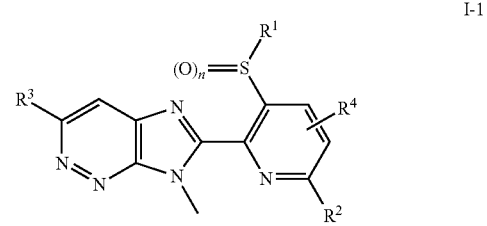

where $R^1$ is $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-haloalkoxy-$(C_1-C_6)$-alkyl, $(C_2-C_6)$-alkenyl, $(C_2-C_6)$-alkenyloxy-$(C_1-C_6)$-alkyl, $(C_2-C_6)$-haloalkenyloxy-$(C_1-C_6)$-alkyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_6)$-alkyl, $(C_2-C_6)$-haloalkynyloxy-$(C_1-C_6)$-alkyl, $(C_2-C_6)$-haloalkynyl, $(C_2-C_6)$-cyanoalkynyl, $(C_3-C_8)$-cycloalkyl, $(C_3-C_6)$-halocycloalkyl, $(C_3-C_6)$-cyanocycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, amino, $(C_1-C_6)$-alkylamino, di-$(C_1-C_6)$-alkyl-amino, $(C_3-C_8)$-cycloalkylamino, $(C_1-C_6)$-alkylcarbonylamino, $(C_1-C_6)$-alkylthio-$(C_1-C_6)$-alkyl, $(C_1-C_6)$-haloalkylthio-$(C_1-C_6)$-alkyl, $(C_1-C_6)$-alkylsulfinyl-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-alkyl, $(C_1-C_6)$-haloalkylsulfonyl-$(C_1-C_6)$-alkyl, $(C_1-C_6)$-alkoxy-$(C_1-C_6)$-alkylthio-$(C_1-C_6)$-alkyl, $(C_1-C_6)$-alkoxy-$(C_1-C_6)$-alkylsulfinyl-$(C_1-C_6)$-alkyl, $(C_1-C_6)$-alkoxy-$(C_1-C_6)$-alkylsulfonyl-$(C_1-C_6)$-alkyl, $(C_1-C_6)$-alkylcarbonyl-$(C_1-C_6)$-alkyl, $(C_1-C_6)$-haloalkylcarbonyl-$(C_1-C_6)$-alkyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkylsulfonylamino, aminosulfonyl)-$C_1-C_6$)-alkyl, $(C_1-C_6)$-alkylaminosulfonyl-$(C_1-C_6)$-alkyl, di-$(C_1-C_6)$-alkylaminosulfonyl-$(C_1-C_6)$-alkyl, or is in each case optionally identically or differently mono- or poly-aryl-, -hetaryl- or -heterocyclyl-substituted $(C_1-C_6)$-alkyl, $(C_1-C_6)$-alkoxy, $(C_2-C_6)$-alkenyl, $(C_2-C_6)$-alkynyl, $(C_3-C_8)$-cycloalkyl, where aryl, hetaryl or heterocyclyl may each optionally be mono- or polysubstituted identically or differently by halogen, cyano, nitro, hydroxyl, amino, carboxyl, carbamoyl, aminosulfonyl, $(C_1-C_6)$-alkyl, $(C_3-C_6)$-cycloalkyl, $(C_1-C_6)$-alkoxy, $(C_1-C_6)$-haloalkyl, $(C_1-C_6)$-haloalkoxy, $(C_1-C_6)$-alkylthio, $(C_1-C_6)$-alkylsulfinyl, $(C_1-C_6)$-alkylsulfonyl, $(C_1-C_6)$-alkylsulfimino, $(C_1-C_6)$-alkylsulfimino-$(C_1-C_6)$-alkyl, $(C_1-C_6)$-alkylsulfimino-$(C_2-C_6)$-alkylcarbonyl, $(C_1-C_6)$-alkylsulfoximino, $(C_1-C_6)$-alkylsulfoximino-$(C_1-C_6)$-alkyl, $(C_1-C_6)$-alkylsulfoximino-$(C_2-C_6)$-alkylcarbonyl, $(C_1-C_6)$-alkoxycarbonyl, $(C_1-C_6)$-alkylcarbonyl, $(C_3-C_6)$-trialkylsilyl or benzyl, $R^2$ is a group selected from —C(=O)—$NR^{11}R^{12}$, —C(=S)— $NR^{11}R^{12}$, —$NR^{11}R^{12}$, $NR^{11}$—C(=O)—$R^8$ and —$NR^{11}$—C(=S)—$R^8$, R³ is C₂-haloalkyl, R⁴ is hydrogen, cyano, halogen, nitro, acetyl, hydroxyl, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, cyano($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), is in each case optionally singly or multiply, identically or differently substituted aryl or hetaryl, where (in the case of hetaryl) at least one carbonyl group may optionally be present and where possible substituents in each case are as follows: cyano, carboxyl, halogen, nitro, acetyl, hydroxyl, amino, SCN, tri-($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di-($C_1$-$C_6$)alkylaminocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulfonylamino, ($C_1$-$C_6$)alkylamino, di-($C_1$-$C_6$)alkylamino, aminosulfonyl, ($C_1$-$C_6$)alkylaminosulfonyl, di-($C_1$-$C_6$)alkylaminosulfonyl, ($C_1$-$C_6$)alkylsulfoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, ($C_1$-$C_6$)alkylcarbonylamino, R⁸ is amino or in each case optionally singly or multiply, identically or differently substituted $C_1$-$C_4$-alkylamino, di-($C_1$-$C_4$)-alkylamino, $C_2$-$C_6$-alkenylamino, $C_2$-$C_6$-alkynylamino, $C_3$-$C_{12}$-cycloalkylamino, $C_3$-$C_{12}$-cycloalkyl-($C_1$-$C_6$)-alkylamino, $C_4$-$C_{12}$-bicycloalkylamino or hydrazino, where the substituents may independently be selected from halogen, cyano, nitro, hydroxyl, (C=O)OH, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_2$-$C_6$-alkoxycarbonyl, $C_2$-$C_6$-alkylcarbonyl, $C_1$-$C_6$-alkylthiocarbonyl, $C_1$-$C_6$-haloalkylcarbonyl, $C_1$-$C_6$-haloalkylthiocarbonyl, $C_1$-$C_6$-alkylcarbonylamino, aminocarbonyl, $C_1$-$C_6$-alkylaminocarbonyl, di-($C_1$-$C_6$)-alkylaminocarbonyl, aminothiocarbonyl, $C_1$-$C_6$-alkylaminothiocarbonyl, di-($C_1$-$C_6$)-alkylaminothiocarbonyl, $C_3$-$C_6$-trialkylsilyl, amino, $C_1$-$C_4$-alkylamino, di-($C_1$-$C_4$-alkyl)amino, $C_3$-$C_6$-cycloalkylamino, aminosulfonyl, $C_1$-$C_6$-alkylaminosulfonyl, di-($C_1$-$C_6$)-alkylaminosulfonyl, sulfonylamino, $C_1$-$C_6$-alkylsulfonylamino and di-($C_1$-$C_6$)-alkylsulfonylamino, R¹¹, R¹² are independently hydrogen or in each case optionally singly or multiply, identically or differently substituted $C_1$-$C_6$-alkyl, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl or $C_4$-$C_{12}$-bicycloalkyl, where the substituents may independently be selected from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_1$-$C_4$-alkylsulfimino-$C_1$-$C_4$-alkyl, $C_1$-$C_4$-alkylsulfimino-$C_2$-$C_5$-alkylcarbonyl, $C_1$-$C_4$-alkylsulfoximino, $C_1$-$C_4$-alkylsulfoximino-$C_1$-$C_4$-alkyl, $C_1$-$C_4$-alkylsulfoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, amino, $C_1$-$C_4$-alkylamino, di-($C_1$-$C_4$-alkyl)amino, $C_3$-$C_6$-cycloalkylamino, a phenyl ring and a 3- or 6-membered aromatic partly saturated or saturated heterocycle, where the phenyl ring or heterocycle may in each case optionally be mono- or polysubstituted identically or differently, and where the substituents may independently be selected from $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$- alkoxy)carbonyl, ($C_1$-$C_6$-alkyl)aminocarbonyl, di-($C_1$-$C_4$-alkyl)aminocarbonyl, tri-($C_1$-$C_2$)alkylsilyl, ($C_1$-$C_4$-alkyl)($C_1$-$C_4$-alkoxy)imino or $R^{11}$, $R^{12}$ are independently a phenyl ring or a 3- to 6-membered aromatic partly saturated or saturated heterocycle, where the heteroatoms are selected from the group of N, S and O, where the phenyl ring or heterocycle may in each case optionally be mono- or polysubstituted identically or differently, and where the substituents may independently be selected from $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, (C=O)OH, $CONH_2$, $NO_2$, OH, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl and ($C_1$-$C_4$-alkyl)($C_1$-$C_4$-alkoxy)imino, and n is 0, 1 or 2.

8. Compound of formula (I-2)

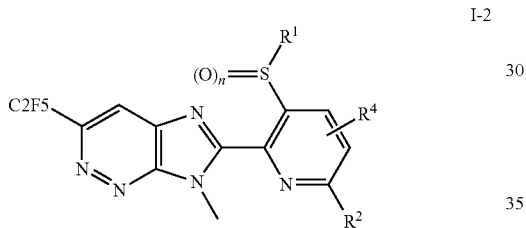

I-2 where $R^1$ is ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-haloalkoxy-($C_1$-$C_6$)-alkyl, ($C_2$-$C_6$)-alkenyl, ($C_2$-$C_6$)-alkenyloxy-($C_1$-$C_6$)-alkyl, ($C_2$-$C_5$)-haloalkenyloxy-($C_1$-$C_6$)-alkyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_6$)-alkyl, ($C_2$-$C_6$)-haloalkynyloxy-($C_1$-$C_6$)-alkyl, ($C_2$-$C_6$)-haloalkynyl, ($C_2$-$C_6$)-cyanoalkynyl, ($C_3$-$C_8$)-cycloalkyl, ($C_3$-$C_6$)-halocycloalkyl, ($C_3$-$C_6$)-cyanocycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, amino, ($C_1$-$C_6$)-alkylamino, di-($C_1$-$C_6$)-alkyl-amino, ($C_3$-$C_8$)-cycloalkylamino, ($C_1$-$C_6$)-alkylcarbonylamino, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylsulfinyl-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-alkyl, ($C_1$-$C_6$)-haloalkylsulfonyl-($C_1$-$C_6$)-alkyl, ($C_1$-$C_6$)-alkoxy-($C_1$-$C_6$)-alkylthio-($C_1$-$C_6$)-alkyl, ($C_1$-$C_6$)-alkoxy-($C_1$-$C_6$)-alkylsulfinyl-($C_1$-$C_6$)-alkyl, ($C_1$-$C_6$)-alkoxy-($C_1$-$C_6$)-alkylsulfonyl-($C_1$-$C_6$)-alkyl, ($C_1$-$C_6$)-alkylcarbonyl-($C_1$-$C_6$)-alkyl, ($C_1$-$C_6$)-haloalkylcarbonyl-($C_1$-$C_6$)-alkyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkylsulfonylamino, aminosulfonyl)-$C_1$-$C_6$)-alkyl, ($C_1$-$C_6$)-alkylaminosulfonyl-($C_1$-$C_6$)-alkyl, di-($C_1$-$C_6$)-alkylaminosulfonyl-($C_1$-$C_6$)-alkyl, or is in each case optionally identically or differently mono- or poly-aryl-, -hetaryl- or -heterocyclyl-substituted ($C_1$-$C_6$)-alkyl, ($C_1$-$C_6$)-alkoxy, ($C_2$-$C_6$)-alkenyl, ($C_2$-$C_6$)-alkynyl, ($C_3$-$C_8$)-cycloalkyl, where aryl, hetaryl or heterocyclyl may each optionally be mono- or polysubstituted identically or differently by halogen, cyano, nitro, hydroxyl, amino, carboxyl, carbamoyl, aminosulfonyl, ($C_1$-$C_6$)-alkyl, ($C_3$-$C_6$)-cycloalkyl, ($C_1$-$C_6$)-alkoxy, ($C_1$-$C_6$)-haloalkyl, ($C_1$-$C_6$)-haloalkoxy, ($C_1$-$C_6$)-alkylthio, ($C_1$-$C_6$)-alkylsulfinyl, ($C_1$-$C_6$)-alkylsulfonyl, ($C_1$-$C_6$)-alkylsulfimino, ($C_1$-$C_6$)-alkylsulfimino-($C_1$-$C_6$)-alkyl, ($C_1$-$C_6$)-alkylsulfimino-($C_2$-$C_6$)-alkylcarbonyl, ($C_1$-$C_6$)-alkylsulfoximino, ($C_1$-$C_6$)-alkylsulfoximino-($C_1$-$C_6$)-alkyl, ($C_1$-$C_6$)-alkylsulfoximino-($C_2$-$C_6$)-alkylcarbonyl, ($C_1$-$C_6$)-alkoxycarbonyl, ($C_1$-$C_6$)-alkylcarbonyl, ($C_3$-$C_6$)-trialkylsilyl or benzyl, $R^2$ is a group selected from —C(=O)—$NR^{11}R^{12}$, —C(=S)— $NR^{11}R^{12}$, —$NR^{11}R^{12}$, $NR^{11}$—C(=O)—$R^8$ and —$NR^{11}$—C(=S)—$R^8$, $R^4$ is hydrogen, cyano, halogen, nitro, acetyl, hydroxyl, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, cyano($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), is in each case optionally singly or multiply, identically or differently substituted aryl or hetaryl, where (in the case of hetaryl) at least one carbonyl group may optionally be present and where possible substituents in each case are as follows: cyano, carboxyl, halogen, nitro, acetyl, hydroxyl, amino, SCN, tri-($C_1$-$C_6$) alkylsilyl, ($C_3$-$C_6$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-(C₁-C₆)-alkoxy, (C₁-C₆)alkoxycarbonyl-(C₁-C₆)alkyl, (C₁-C₆)alkoxy-(C₁-C₆)alkyl, (C₂-C₆)alkenyl, (C₂-C₆)haloalkenyl, (C₂-C₆)cyanoalkenyl, (C₂-C₆)alkynyl, (C₂-C₆)haloalkynyl, (C₂-C₆)cyanoalkynyl, (C₁-C₆)alkoxy, (C₁-C₆)haloalkoxy, (C₁-C₆)cyanoalkoxy, (C₁-C₆) alkoxycarbonyl-(C₁-C₆)alkoxy, (C₁-C₆)alkoxy-(C₁-C₆)alkoxy, (C₁-C₆)alkylhydroxyimino, (C₁-C₆) alkoxyimino, (C₁-C₆)alkyl-(C₁-C₆)alkoxyimino, (C₁-C₆)haloalkyl-(C₁-C₆)alkoxyimino, (C₁-C₆)alkylthio, (C₁-C₆)haloalkylthio, (C₁-C₆)alkoxy-(C₁-C₆)alkylthio, (C₁-C₆)alkylthio-(C₁-C₆)alkyl, (C₁-C₆)alkylsulfinyl, (C₁-C₆)haloalkylsulfinyl, (C₁-C₆) alkoxy-(C₁-C₆)alkylsulfinyl, (C₁-C₆)alkylsulfinyl-(C₁-C₆)alkyl, (C₁-C₆)alkylsulfonyl, (C₁-C₆) haloalkylsulfonyl, (C₁-C₆)alkoxy-(C₁-C₆)alkylsulfonyl, (C₁-C₆)alkylsulfonyl-(C₁-C₆)alkyl, (C₁-C₆)alkylsulfonyloxy, (C₁-C₆)alkylcarbonyl, (C₁-C₆)haloalkylcarbonyl, (C₁-C₆)alkylcarbonyloxy, (C₁-C₆)alkoxycarbonyl, (C₁-C₆)haloalkoxycarbonyl, aminocarbonyl, (C₁-C₆)alkylaminocarbonyl, di-(C₁-C₆)alkylaminocarbonyl, (C₂-C₆)alkenylaminocarbonyl, di-(C₂-C₆)-alkenylaminocarbonyl, (C₃-C₈)cycloalkylaminocarbonyl, (C₁-C₆)alkylsulfonylamino, (C₁-C₆)alkylamino, di-(C₁-C₆)alkylamino, aminosulfonyl, (C₁-C₆)alkylaminosulfonyl, di-(C₁-C₆)alkylaminosulfonyl, (C₁-C₆) alkylsulfoximino, aminothiocarbonyl, (C₁-C₆) alkylaminothiocarbonyl, di-(C₁-C₆)alkylaminothiocarbonyl, (C₃-C₈)cycloalkylamino, (C₁-C₆)alkylcarbonylamino, $R^8$ is amino or in each case optionally singly or multiply, identically or differently substituted C₁-C₄-alkylamino, di-(C₁-C₄)-alkylamino, C₂-C₆-alkenylamino, C₂-C₆-alkynylamino, C₃-C₁₂-cycloalkylamino, C₃-C₁₂-cycloalkyl-(C₁-C₆)-alkylamino, C₄-C₁₂-bicycloalkylamino or hydrazino, where the substituents may independently be selected from halogen, cyano, nitro, hydroxyl, (C=O)OH, C₁-C₆-alkyl, C₃-C₆-cycloalkyl, C₁-C₄-alkoxy, C₁-C₄-haloalkoxy, C₁-C₄-alkylthio, C₁-C₄-alkylsulfinyl, C₁-C₄-alkylsulfonyl, C₁-C₄-haloalkylthio, C₁-C₄-haloalkylsulfinyl, C₁-C₄-haloalkylsulfonyl, C₂-C₆-alkoxycarbonyl, C₂-C₆-alkylcarbonyl, C₁-C₆-alkylthiocarbonyl, C₁-C₆-haloalkylcarbonyl, C₁-C₆-haloalkylthiocarbonyl, C₁-C₆-alkylcarbonylamino, aminocarbonyl, C₁-C₆-alkylaminocarbonyl, di-(C₁-C₆)-alkylaminocarbonyl, aminothiocarbonyl, C₁-C₆-alkylaminothiocarbonyl, di-(C₁-C₆)-alkylaminothiocarbonyl, C₃-C₆-trialkylsilyl, amino, C₁-C₄-alkylamino, di-(C₁-C₄-alkyl)amino, C₃-C₆-cycloalkylamino, aminosulfonyl, C₁-C₆-alkylaminosulfonyl, di-(C₁-C₆)-alkylaminosulfonyl, sulfonylamino, C₁-C₆-alkylsulfonylamino and di-(C₁-C₆)-alkylsulfonylamino, $R^{11}$, $R^{12}$ are independently hydrogen or in each case optionally singly or multiply, identically or differently substituted C₁-C₆-alkyl, C₂-C₆-alkenyl, C₂-C₆-alkynyl, C₃-C₁₂-cycloalkyl, C₃-C₁₂-cycloalkyl-C₁-C₆-alkyl or C₄-C₁₂-bicycloalkyl, where the substituents may independently be selected from halogen, cyano, nitro, hydroxyl, C₁-C₆-alkyl, C₃-C₆-cycloalkyl, C₁-C₄-alkoxy, C₁-C₄-haloalkoxy, C₁-C₄-alkylthio, C₁-C₄-alkylsulfinyl, C₁-C₄-alkylsulfonyl, C₁-C₄-alkylsulfimino, C₁-C₄-alkylsulfimino-C₁-C₄-alkyl, C₁-C₄-alkylsulfimino-C₂-C₅-alkylcarbonyl, C₁-C₄-alkylsulfoximino, C₁-C₄-alkylsulfoximino-C₁-C₄-alkyl, C₁-C₄-alkylsulfoximino-C₂-C₅-alkylcarbonyl, C₂-C₆-alkoxycarbonyl, C₂-C₆-alkylcarbonyl, C₃-C₆-trialkylsilyl, amino, C₁-C₄-alkylamino, di-(C₁-C₄-alkyl) amino, C₃-C₆-cycloalkylamino, a phenyl ring and a 3- or 6-membered aromatic partly saturated or saturated heterocycle, where the phenyl ring or heterocycle may in each case optionally be mono- or polysubstituted identically or differently, and where the substituents may independently be selected from C₁-C₆-alkyl, C₂-C₆-alkenyl, C₂-C₆-alkynyl, C₃-C₆-cycloalkyl, C₁-C₆-haloalkyl, C₂-C₆-haloalkenyl, C₂-C₆-haloalkynyl, C₃-C₆-halocycloalkyl, halogen, cyano, (C=O) OH, CONH₂, NO₂, OH, C₁-C₄-alkoxy, C₁-C₄-haloalkoxy, C₁-C₄-alkylthio, C₁-C₄-alkylsulfinyl, C₁-C₄-alkylsulfonyl, C₁-C₄-haloalkylthio, C₁-C₄-haloalkylsulfinyl, C₁-C₄-haloalkylsulfonyl, C₁-C₄-alkylamino, di-(C₁-C₄-alkyl)amino, C₃-C₆-cycloalkylamino, (C₁-C₆-alkyl)carbonyl, (C₁-C₆-alkoxy)carbonyl, (C₁-C₆-alkyl)aminocarbonyl, di-(C₁-C₄-alkyl)aminocarbonyl, tri-(C₁-C₂)alkylsilyl, (C₁-C₄-alkyl)(C₁-C₄-alkoxy)imino or $R^{11}$, $R^{12}$ are independently a phenyl ring or a 3- to 6-membered aromatic partly saturated or saturated heterocycle, where the heteroatoms are selected from the group of N, S and O, where the phenyl ring or heterocycle may in each case optionally be mono- or polysubstituted identically or differently, and where the substituents may independently be selected from C₁-C₆-alkyl, C₂-C₆-alkenyl, C₂-C₆-alkynyl, C₃-C₆-cycloalkyl, C₁-C₆-haloalkyl, C₂-C₆-haloalkenyl, C₂-C₆-haloalkynyl, C₃-C₆-halocycloalkyl, halogen, cyano, (C=O)OH, CONH₂, NO₂, OH, C₁-C₄-alkoxy, C₁-C₄-haloalkoxy, C₁-C₄-alkylthio, C₁-C₄-alkylsulfinyl, C₁-C₄-alkylsulfonyl, C₁-C₄-haloalkylthio, C₁-C₄-haloalkylsulfinyl, C₁-C₄-haloalkylsulfonyl, C₁-C₄-alkylamino, di-(C₁-C₄-alkyl)amino, C₃-C₆-cycloalkylamino, (C₁-C₆-alkyl)carbonyl, (C₁-C₆-alkoxy) carbonyl, (C₁-C₆-alkyl)aminocarbonyl, di-(C₁-C₄-alkyl)aminocarbonyl, tri-(C₁-C₂)alkylsilyl and (C₁-C₄-alkyl)(C₁-C₄-alkoxy)imino, and n is 0, 1 or 2.

9. Compound of formula (I) according to claim 1, wherein $R^3$ is pentafluoroethyl.

10. Compound of formulae (I-a) to (I-o)

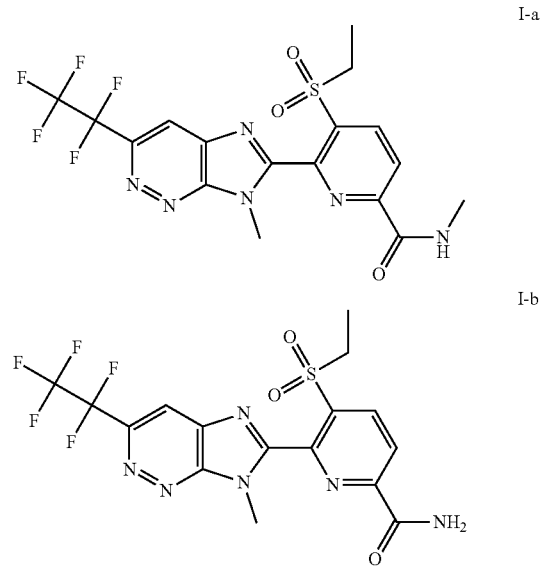

I-c
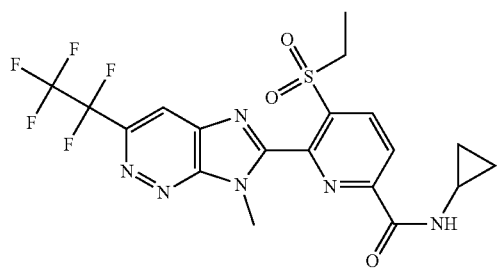
I-d
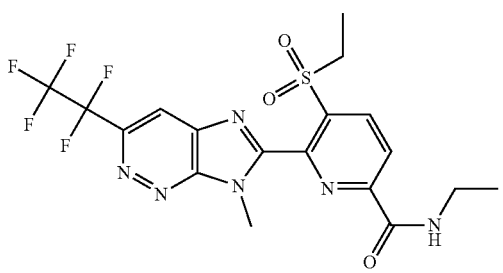
I-e
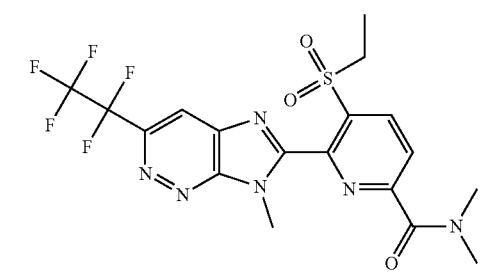
I-f
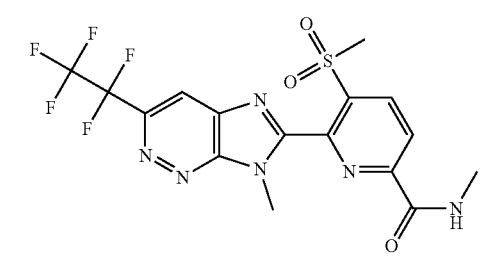
I-g
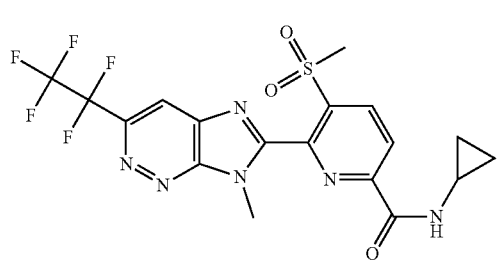
I-h
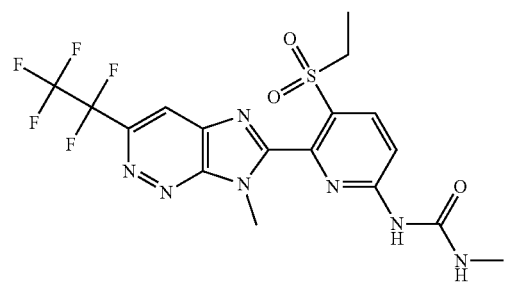
I-i
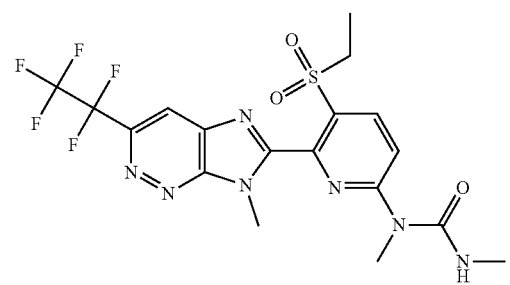
I-j
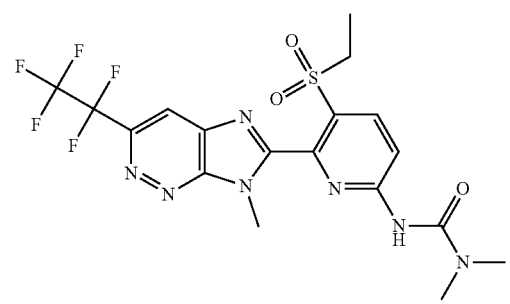
I-k
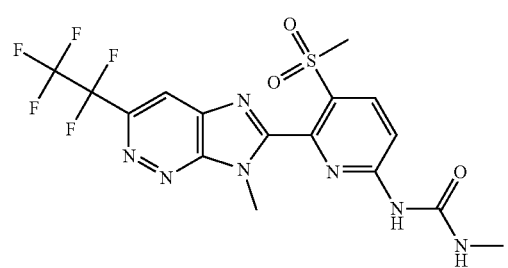
I-l
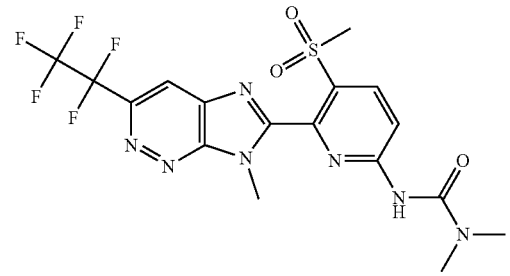

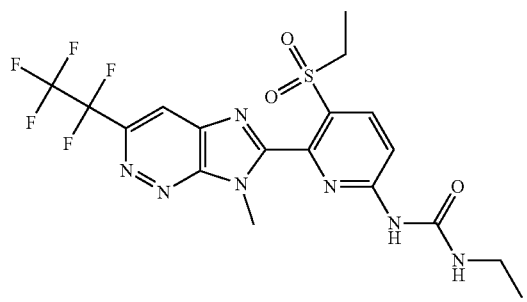

I-m

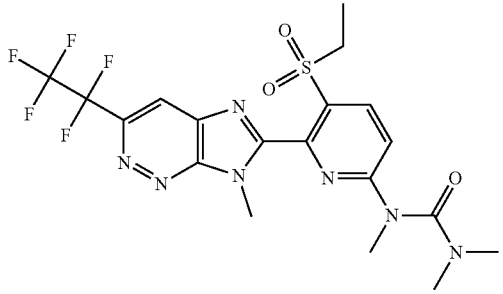

I-o

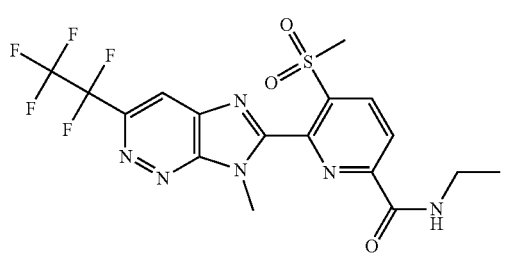

I-n

11. Agrochemical formulation comprising a Compound of formula (I) according to claim 1 and one or more extenders and/or surfactants.

12. Agrochemical formulation according to claim 11, additionally comprising a further agrochemically active ingredient.

13. Method for controlling one or more animal pests, comprising allowing a compound of formula (I) according to claim 1 or an agrochemical formulation thereof to act on the animal pests and/or a habitat thereof.

* * * * *